(12) United States Patent  (10) Patent No.: US 8,410,247 B2
Raines et al.  (45) Date of Patent: Apr. 2, 2013

(54) WATER-SOLUBLE PHOSPHINOTHIOL REAGENTS

(75) Inventors: Ronald T. Raines, Madison, WI (US); Annie Tam, New Brunswick, NJ (US); Matthew B. Soellner, Dexter, MI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 567 days.

(21) Appl. No.: 12/546,249

(22) Filed: Aug. 24, 2009

(65) Prior Publication Data

US 2010/0048866 A1  Feb. 25, 2010

Related U.S. Application Data

(60) Provisional application No. 61/091,298, filed on Aug. 22, 2008.

(51) Int. Cl.
*C07C 231/10* (2006.01)
*C07F 9/50* (2006.01)
*C07K 1/02* (2006.01)
*C07K 1/04* (2006.01)

(52) U.S. Cl. ............ 530/340; 530/334; 564/15; 564/123

(58) Field of Classification Search ........................ None
See application file for complete search history.

(56) References Cited

U.S. PATENT DOCUMENTS

| | | | |
|---|---|---|---|
| 6,972,320 B2 | 12/2005 | Raines et al. | |
| 6,974,884 B2 | 12/2005 | Raines et al. | |
| 7,256,259 B2 | 8/2007 | Raines et al. | |
| 7,317,129 B2 | 1/2008 | Raines et al. | |
| 2008/0020942 A1 | 1/2008 | Raines et al. | |

OTHER PUBLICATIONS

Agard et al. (Web Release Oct. 20, 2006) "A Comparative Study of Bioorthogonal Reactions with Azides," *ACS Chem. Biol.* 1(10):644-648.
Bräse et al (Aug. 2005) "Organic Azides: An Exploding Diversity of a Unique Class of Compounds," *Angew. Chem. Int. Ed.* 44(33):5188-5240.
Houk et al. (Oct. 1987) "Structure-Reactivity Relations for Thiol-Disulphide Interchange," *J. Am. Chem. Soc.* 109(22):6825-6836.
Köhn et al. (Jun. 2004) "The Staudinger Ligation—A Gift to Chemical Biology," *Angew. Chem. Int. Ed.* 43(24):3106-3116.
Nilsson et al. (Web Release Dec. 19, 2000) "High-Yielding Staudinger Ligation of a Phosphinothioester and Azide to Form a Peptide," *Org. Lett.* 3(1):9-12.
Nilsson et al. (Web Release Jun. 9, 2000) "Staudinger Ligation: A Peptide from a Thioester and Azide," *Org. Lett.* 2(13):1939-1941.

(Continued)

*Primary Examiner* — Jeffrey E Russel
(74) *Attorney, Agent, or Firm* — Lathrop & Gage LLP

(57) ABSTRACT

Water soluble reagents and methods for the formation of an amide bond between a phosphinothioester and an azide in an aqueous medium. The phosphinothioester is generated using a water-soluble phosphinothiol reagent. This reaction allows formation of an amide bond between a wide variety of chemical species including amino acids, peptides or protein fragments in an aqueous solution. Of particular interest, this reaction allows for the formation of an amide bond in a physiological setting. In a specific embodiment, this invention provides reagents and methods for peptide ligation in an aqueous medium. The reaction eliminates the need for a cysteine residue and is traceless leaving no residual atoms in the ligated peptide product.

21 Claims, 4 Drawing Sheets

OTHER PUBLICATIONS

Nilsson et al. (2003) "Protein Assembly to Mine the Human Genome," In; *Chemical Probes in Biology* (*NATO ASI Series*), Schneider, M.P. Ed., Kluwer Academic: Boston, MA pp. 359-369.

Nilsson et al. (Web release Jan. 2005) "Chemical Synthesis of Proteins," *Ann. Rev. Biophys. Biomol. Struct.* 34:91-118.

Nilsson et al. (Web Release Apr. 9, 2003) "Protein Assembly by Orthogonal Chemical Ligation Methods," *J. Am. Chem. Soc.* 125(18):5268-5269.

Offer et al. (Web Release Dec. 14, 1999) "$N^\alpha$-2-Mercaptobenzylamine-Assisted Chemical Ligation," *Org. Lett.* 2(1):23-26.

Saxon et al. (Mar. 2000) "Cell Surface Engineering by a Modified Staudinger Reaction," *Science* 287:2007-2010.

Saxon et al. (Web Release Jun. 20, 2000) "A 'Traceless' Staudinger Ligation for the Chemoselective Synthesis of Amide Bonds," *Org. Lett.* 2(14):2141-2143.

Soellner et al. (Web Release Dec. 1, 2006) "Staudinger Ligation of Peptides at Non-Glycyl Residues," *J. Org. Chem.* 71(26):9824-9840.

Soellner et al. (Web Release Jun. 20, 2006) "Reaction Mechanism and Kinetics of the Traceless Staudinger Ligation," *J. Am. Chem. Soc.* 128(27):8820-8828.

Soellner et al. (Web Release Jun. 14, 2002) "Staudinger Ligation of $\alpha$-Azido Acids Retains Stereochemistry," *J. Org. Chem.* 67(14):4993-4996.

Soellner et al. (Web Release Sep. 4, 2003) "Site-Specific Protein Immobilization by Staudinger Ligation," *J. Am. Chem. Soc.* 125(39):11790-11791.

Tam et al. (Web Release Aug. 22, 2007) "Water-soluble Phosphinothiols for Traceless Staudinger Ligation and Integration with Expressed Protein Ligation," *J. Am. Chem. Soc.* 129(37):11421-11430.

Tam et al. (Feb. 1, 2009) "Coulombic Effects on the Traceless Staudinger Ligation in Water," *Biorg. Med. Chem.* 17(3):1055-1063.

Tam et al. (2009) "Protein Engineering with the Traceless Staudinger Ligation," *Meth. Enzymol.* 462, Chapter 2, 25-44, Muir and Ableson (Eds), Academic Press.

Tam et al. (Web release Mar. 3, 2008) "Electronic and Steric Effects on the Rate of the Traceless Staudinger Ligation," *Org. Biomol. Chem.* 6(7):1173-1175.

WATER-SOLUBLE PHOSPHINOTHIOL REAGENTS

CROSS-REFERENCE TO RELATED APPLICATIONS

This application claims the benefit of U.S. provisional application 61/091,298, filed Aug. 22, 2008 which is incorporated by reference herein in its entirety.

STATEMENT REGARDING GOVERNMENT SUPPORT

This invention was made with government support under GM044783 awarded by the National Institutes of Health. The government has certain rights in this invention.

BACKGROUND OF THE INVENTION

This invention is in the field of peptide chemistry, in particular relating to methods for forming amide bonds in water useful in the synthesis of peptides and proteins in biological systems and also in the synthesis of derivatized peptides or proteins in aqueous solutions.

New methods are facilitating the total chemical synthesis of proteins. For historical references, see: Merrifield, R. B. Science 1984, 232, 341-347; Kent, S. B. Annu., Rev. Biochem. 1988, 57, 957-989; Kaiser, E. T. Acc. Chem. Res. 1989, 22, 47-54. In particular, Kent and others have developed a means to stitch together two unprotected peptides in aqueous solution called "native chemical ligation." Dawson, P. E.; Muir, T. W.; Clark-Lewis, I.; Kent, S. B. Science 1994, 266, 776-779. For important precedents, see: Wieland, T.; Bikelmann, E.; Bauer, L.; Lang, H. U.; Lau, H. Liebigs Ann. Chem. 1953, 583, 129-149; Kemp, D. S.; Galakatos, N. G. J. Org. Chem. 1986, 51, 1821-1829.

In native chemical ligation the thiolate of an N-terminal cystein residue in one peptide attacks the carbon of a C-terminal thioester in another peptide to produce, ultimately, an amide bond between the two peptides. This ligation method was discovered when the reaction of ValSPh and CysOH in aqueous buffer was shown to yield the dipeptide: ValCysOh (Wieland, T.; Bikelmann, E.; Bauer, L.; Lang, H. U.; Lau, H. Liebigs Ann. Chem. 1953, 583, 129-149).

Recently, Muir and others have expanded the utility of native chemical ligation by demonstrating that the thioester fragment can be produced readily with recombinant DNA (rDNA) techniques. Muir, T. W.; Sondhi, D.; Cole, P. A. Proc. Natl. Acad. Sci. U.S.A.; 1998, 9, 6705-6710; Evans, Jr., T. C.; Benner, J.; Xu, M.-Q. Protein Sci. 1998, 7, 2256-2264; Ayers, B.; Blaschke, U. K.; Camarero, J. A.; Cotton, G. J.; Holford, M.; Muir, T. W. Biopolymers 2000, 51, 343-354. For reviews, see: Holford, M.; Muir, T. W. Structure 1998, 15, 951-956; Cotton, G. J.; Muir, T. W. Chem. Biol. 1999, 6, R247-R256. Evans, Jr.; T. C.; Xu, M.-Q. Biopolymers 2000, 51, 333-342. This type of "native chemical ligation" has been designated "protein ligation"

Although native chemical ligation is useful in some systems, it has severe limitations. The method relies on the formation of a peptide bond to a cysteine residue. Creating this type of linkage is not always possible, as cystein comprises only 1.7% of the residues in globular proteins. Hence, most proteins cannot be prepared by a method that requires peptides to be coupled only at a cysteine residue.

Offer and Dawson have recently described a peptide ligation method that does not require the presence of cysteine. (Offer, J.; Dawson, P. E. Org. Lett. 2000, 2, 23-26). In their method, a peptide bond is formed from a thioester and mercaptobenzylamine. Though effective, this method necessarily leaves o-mercaptobenzylamine in the ligation product.

In the well-known Staudinger reaction a phosphine is used to reduce an azide to an amine:

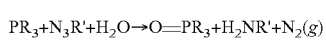

(Staudinger, H.; Meyer, J. Helv. Chim. Acta. 1919, 2, 635-646. For reviews, see: Gololobob, Yu. G.; Zhmurova, I. N.; Kasukhin, L. F. Tetrahedron 1981, 37, 437-472; Gololobov, Yu. G.; Kasukhin, L. F. Tetrahedron 1992, 48, 1353-1406). The intermediate in the reaction is an iminophosphorane $(R''_3P^+\text{---}^-NR)$, which has a nucleophilic nitrogen.

Recently, Saxon et al. have reported a modification of the Staudinger ligation to form an amide from an azide using a phosphine reagent. (Saxon, E.; Armstrong, J. I.; Bertozzi, C. R.; Org. Lett. 2000, 2, 2141-2143). The phosphine reagents:

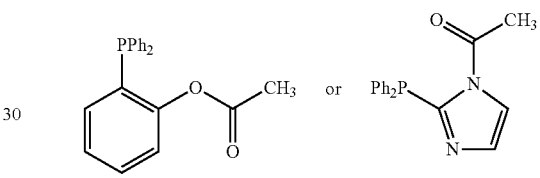

when reacted with an azido nucleosides are reported to result in the formation of an amide by acryl group transfer. The ligation is called traceless because no portion of the phosphine reagent other that the acyl group remains in the product. The authors also report that the reaction of a phosphinothioester:

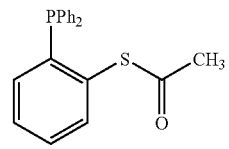

with the same azido nucleoside results initially in aza-ylide hydrolysis rather that acyl transfer. The observation of amide products after several days in characterized as the probably result of reaction of amine hydrolysis products with the thioester. The authors indicate that the phosphinothioester employed is not "amenable" to the reaction.

Recently, a strategy has been developed for protein assembly utilizing the Staudinger reaction. Nilsson, B. L; Kiessling, L. L.; Raines, R. T.; Org. Lett. 2000, 2, 1939-1941; Nilsson, B. L.; Kiessling, L. L.; Raines, R. T.; Org. Lett. 2001, 3, 9-12; Kohn, M.; Breinbauer, R.; Angew. Chem. Int. Ed. 2004, 43, 3106-3116. This traceless Staudinger ligation proceeds through an azide reduction by a phosphine via an iminophosphorane intermediate. This reaction is extremely useful as it can mediate the nonengrammic ligation of peptides at virtually any residue. Soellner, M. B.; Tam, A.; Raines, R. T. J. Org. Chem. 2006, 71, 9824-9830. The iminophosphorane can be acylated to yield an amine. The proposed mechanism is shown in Scheme 1.

Scheme 1

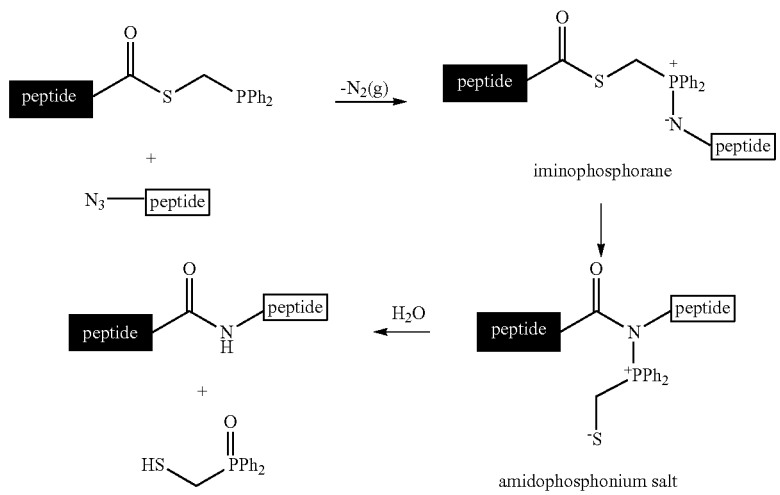

Although this reaction is extremely useful, it requires the use of organic solvents and therefore has limited use in biological environments. U.S. Pat. Nos. 6,972,320; 6,974,884; 7,256,259 and 7,317,129 relate to this "traceless" method for formation of an amide bond between a phosphinothioester and an azide as well as to reagents useful in such methods. More specifically U.S. Pat. No. 7,256,259 relates to a method for covalent ligation of molecules to surfaces via amide bond formation. U.S. Pat. Nos. 6,974,884 and 7,317,129 relate to methods for synthesis of phosphinothiol reagents and reagents useful in the formation of amide bonds and for peptide ligation. The patent also relates to phosphine-borane complexes useful as reagents in such methods.

SUMMARY OF THE INVENTION

This invention in general provides for reagents and methods for the formation of an amide bond between a phosphinothioester and an azide in an aqueous medium. The phosphinothioester is generated using a water-soluble phosphinothiol reagent. This reaction allows formation of an amide bond between a wide variety of chemical species including amino acids, peptides or protein fragments in an aqueous solution. Of particular interest, this reaction allows for the formation of an amide bond in a physiological setting. In a specific embodiment, this invention provides reagents and methods for peptide ligation in an aqueous medium. The reaction eliminates the need for a cysteine residue and leaves no residual atoms in the ligated peptide product (i.e. the ligation is traceless).

In one embodiment, the invention relates to water soluble phosphinothiols for peptide ligation in an aqueous solution having the following formula I:

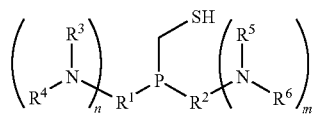

as well as protonated and quaternary ammonium ions and salts thereof wherein:
$R^1$ and $R^2$ are linkers that are organic biradicals which can be selected from optionally substituted arylene (e.g., —$C_6H_4$—), optionally substituted heteroarylene, optionally substituted alkylene chains, e.g., —$(CH_2)_p$— where p is an integer indicating the length of the chain, or combinations thereof and wherein the alkylene may be a cycloalkylene;
n and m are 0, 1, or 2 and n+m is at least 1; and
$R^3$-$R^6$, independently, are selected from guanidine, alkyl, alkenyl, alkynyl, aryl, or heteroaryl groups all of which are optionally substituted, wherein $R^3$ and $R^4$ can be linked to form a 5-8 member ring which contains N and optionally contains one or more additional heteroatoms, $R^5$ and $R^6$ can be linked to form a 5-8 member ring which contains N and optionally contains one or more additional heteroatoms or both $R^3$ and $R^4$ and both of $R^5$ and $R^6$ can be linked to form such a ring.

In the $R^1$ and $R^2$ linkers, one or more non-neighboring —$CH_2$— groups, if present, can be replaced with O, S, CO, an ester (—CO—O— or —O—CO—), an amide (—NR"—CO— or —CO—NR"—), or an —N(R")— group, where R" is hydrogen or an optionally substituted alkyl, alkenyl, alkynyl, heterocyclic, aryl or heterocyclic group. In specific embodiments, R" is hydrogen or an alkyl group having 1-6 carbons or 1-3 carbons.

Optional substitution, herein, includes substitution with one or more groups selected from halogens, alkyl, alkenyl, alkynyl, heterocyclic, aryl, heteroaryl, —OH, —OR, —COH, —COR, —COOH, —CO—OR, —O—COR, —O—CO—O—R, —CO—NR—, —NR—CO—R, or —N(R)$_2$ groups, where each R is independently selected from hydrogen or an optionally substituted alkyl, alkenyl, alkynyl, heterocyclic, aryl or heteroaryl group. In specific embodiments, each R is selected from hydrogen or an alkyl group having 1-6 carbons or 1-3 carbons.

In a more specific embodiment, $R^3$ and $R^4$ or $R^5$ and $R^6$, or both combinations of groups, are linked together to form a heterocyclic 6-member ring, such as:

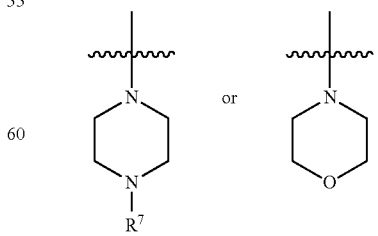

where $R^7$ is hydrogen or an optionally substituted alkyl, alkenyl, alkynyl, heterocyclic, aryl or heteroaryl group. In specific embodiments, $R^7$ is an unsubstituted alkyl having 1-6 carbon atoms or 1-3 carbon atoms. In specific embodiments, $R^7$ is an optionally substituted phenyl group In specific embodiments, n and m are 0, 1, or 2, where n+m=2, 3 or 4. In specific embodiments, n and m are both non-zero. In another specific embodiment, the compound has the following formula II:

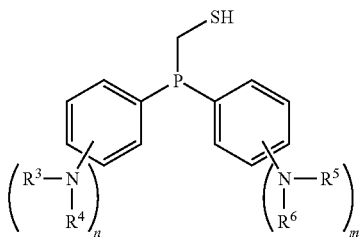

a protonated or quaternary ion or a salt thereof where variables are as defined above. In specific embodiments, n and m are 0, 1 or 2 where n+m=2, 3 or 4. In specific embodiments, n and m are both non-zero. in specific embodiments, the —$NR^3R^4$ and —$NR^5R_6$ groups are substituted at meta, para or both positions on the indicated ring.

In specific embodiments of formula II, $R^3$-$R^6$, are selected from alkyl, cycloalkyl, or aryl, groups which are optionally substituted, for example, with one or more alkyl, cycloalkyl or aryl groups or one or more halides, —OR, —COR, —COOR or —$N(R)_2$ groups, where each R is independently selected from hydrogen or an optionally substituted alkyl, alkenyl, alkynyl, heterocyclic, aryl or heteroaryl group. In specific embodiments, R is an unsubstituted alkyl having 1-6 carbon atoms or 1-3 carbon atoms. In specific embodiments, R is an optionally substituted phenyl group.

In another specific embodiment, $R^3$ and $R^4$, or $R^5$ and $R^6$, or both combinations of groups are linked to form a 6-8-membered ring which can be a carbocylic or heterocyclic ring. In more specific embodiments, each of $R^3$-$R^6$ is an alkyl group. In more specific embodiments, each of $R^3$-$R^6$ is an alkyl group having 1-6 carbon atoms. In specific embodiments, each of $R^3$-$R^6$ is the same alkyl group.

In a specific embodiment, the —$NR^3R^4$ and —$NR^5R^6$ groups are substituted at the meta or para positions or at both positions on the indicated phenyl group.

In another specific embodiment, the phosphinothiol has the following formula III:

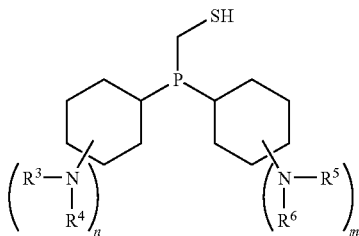

or a protonated or quaternary ion or a salt thereof where variables are as defined above, where n and m are integers ranging from 0 to 6, where n+m is 1 or more. In specific embodiments, n and m are 0, 1 or 2 where n+m=2, 3 or 4. In specific embodiments, n and m are both non-zero.

In a specific embodiment, the —$NR^3R^4$ and —$NR^5R^6$ groups are substituted in trans-positions with respect to the —P— on the indicated cyclohexyl rings. In a specific embodiment, the —$NR^3R^4$ and —$NR^5R^6$ groups are substituted in cis-positions with respect to the —P— on the indicated cyclohexyl rings.

In specific embodiments of formula III, $R^3$-$R^6$ are selected from alkyl, cycloalkyl, or aryl groups which are optionally substituted, for example, with one or more halides, —OR, —COR, —COOR or —$N(R)_2$ groups, where each R is independently selected from hydrogen or an optionally substituted alkyl, alkenyl, alkynyl, heterocyclic, aryl or heteroaryl group. In specific embodiments, R is an unsubstituted alkyl having 1-6 carbon atoms or 1-3 carbon atoms. In specific embodiments, R is an optionally substituted phenyl group.

In another specific embodiment, $R^3$ and $R^4$, or $R^5$ and $R^6$, or both combinations of groups are linked to form a 6-8-membered ring. In more specific embodiments, each of $R^3$-$R^6$ is an alkyl group. In more specific embodiments, each of $R^3$-$R^6$ is an alkyl group having 1-6 carbon atoms or 1-3 carbon atoms. In specific embodiments, each of $R^3$-$R^6$ is the same alkyl group.

In a specific embodiment, $R^1$ and $R^2$ are alkylene groups —$(CH_2)_p$— where p is an integer ranging from 1-6. When $R^1$ or $R^2$ is an alkylene group, one or more non-neighboring —$CH_2$— of the alkylene can be replaced with O, an amide (—CO—NR"), or an (NR") group, where R" is hydrogen or an optionally substituted alkyl, or aryl group. When $R^1$ or $R^2$ is an alkylene group, one or more carbons of the alkylene can be substituted with one or more substituents selected from halogen, OH, OR, COH, COR, COOH, COOR or $N(R)_2$ groups where each R is independently selected from a hydrogen or an optionally substituted alkyl, alkenyl, alkynyl, heterocyclic, aryl or heterocyclic group. In specific embodiments, R is hydrogen or an unsubstituted alkyl group having 1-6 carbons or 1-3 carbons.

In another specific embodiment, the phosphinothiol has the following formula IV:

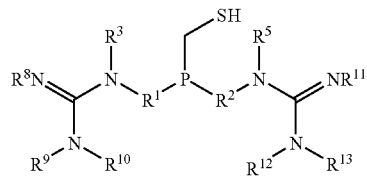

or protonated ions or salts thereof where:
$R^1$ and $R^2$ are linkers as described above;
$R^3$ and $R^5$ are as defined above; and
$R^8$-$R^{13}$, independently, are selected from hydrogen, alkyl, alkenyl, alkynyl, cycloalkyl, aryl, or heteroaryl groups which are optionally substituted, with one or more alkyl, alkenyl, aryl, halides, —OH, —OR, —COH, —COR, —COOH, —CO—OR, —O—COR, —O—CO—O—R, —CO—NR—, —NR—CO—R, or —$N(R)_2$ groups, where each R is independently selected from hydrogen or an optionally substituted alkyl, alkenyl, alkynyl, heterocyclic, aryl or heteroaryl group. In specific embodiments, R is hydrogen or an unsubstituted alkyl group having 1-6 carbons or 1-3 carbons. In specific embodiments, $R^8$-$R^{13}$ are optionally substituted with one or more with halides, —OR, —COR, —COOR or —$N(R)_2$ groups, where each R is independently selected from hydrogen or an optionally substituted alkyl, alkenyl, alkynyl, heterocyclic, aryl or heteroaryl group. In specific embodiments, R is an unsubstituted alkyl having 1-6 carbon atoms or 1-3 carbon atoms. In specific embodiments, R is an optionally substituted phenyl group.

In specific embodiments, $R^9$ and $R^{10}$, $R^{12}$ and $R^{13}$ or both combinations of groups are linked to form a 6-8-membered ring carbocyclic or heterocyclic ring. In specific embodiments, each of $R^3$, $R^5$, $R^8$, or $R^{11}$ is an alkyl group, particularly the same alkyl group and more particularly an alkyl group having 1-3 carbons and most particularly a methyl group. In specific embodiments, each of $R^3$, $R^5$, $R^{8-10}$, or $R^{11-13}$ is an alkyl group, particularly the same alkyl group and more particularly an alkyl group having 1-3 carbons, and most particularly a methyl group.

In another embodiment, this invention relates to a method for the formation of an amide bond in an aqueous solution comprising the steps of converting the desired water soluble phosphinothiol to the corresponding phosphinothioester and reacting the phosphinothioester with desired azide in a buffered aqueous solution of a given pH. In specific embodiments, the pH of the reaction solution is $\geq 7.5$. In specific embodiments, the pH of the reaction solution is between 6.5 and 8.5. In specific embodiments, the pH of the reaction solution is between 7.5 and 8.5. In specific embodiments, the pH of the reaction solution is between 7.2 and 8.2. In specific embodiments, the pH of the reaction solution is between 7.3 and 8.0.

In specific embodiments, the molar ratio of phosphinothioester to azide in the reaction ranges from 3:1 to 0.33:1. In specific embodiments, the molar ratio of phosphinothioester to azide in the reaction ranges from 2:1 to 0.5:1. In specific embodiments, the molar ratio of phosphinothioester to azide in the reaction ranges from 1.2:1 to 0.8 to 1. In specific embodiments, the reaction is carried out with equimolar amounts of phosphinothioester and azide.

In another embodiment, this invention relates to a method for the formation of an amide bond between a wide variety of chemical species such as amino acids, peptides, polypeptides, proteins or protein fragments. This involves the steps of converting the desired water soluble phosphinothiol to the corresponding phosphinothioester linked to the desired species (amino acid, peptide, etc.) and reacting this phosphinothioester with an azide linked to the desired species (amino acid, peptide, etc.) in a buffered aqueous solution of a given pH.

In a specific embodiment, this invention relates to a method of peptide ligation in an aqueous solution comprising the steps of converting the desired water soluble phosphinothiol to the corresponding phosphinothioester linked to the desired peptide and reacting the resulting phosphinothioester with an azide linked to the desired peptide in a buffered aqueous solution at a given pH. Preferably the pH is within the range of physiological pH.

In another embodiment, the invention relates to a method for immobilizing a molecule on a surface in an aqueous solution comprising the steps of converting the desired phosphinothiol to the corresponding phosphinothioester and reacting it with the desired azide in an aqueous solution of a given pH, wherein either the phosphinothioester or the azide is linked to a surface. In a specific embodiment, the reaction is carried out in a buffered aqueous solution at selected pH. Preferably the pH is within the range of physiological pH.

The invention further provides kits which provide components for carrying out the methods of the invention. In a specific embodiment, the invention provides a kit for forming an amide bond which comprises one or more of the water soluble phosphinothiol reagents of this invention. Kits may optionally include one or more azides or reagents for generating an azide, particularly an azide of an amino acid, peptide, protein, saccharide or nucleoside. In a specific embodiment, the invention provides a kit for synthesis of peptides or proteins which comprises one or more of the water soluble phosphinothiol reagents of this invention. The kit may optionally further contain one or more amino acid side chain protecting groups, one or more reagents for generating a thioester of an amino acid, peptide or protein or one or more reagents for generating an azide of an amino acid, peptide or protein. The kits optionally contain one or more azido amino acids for use in the method. The kits may also optionally include resin or other solid phase materials that are appropriate for conducting the ligation of this invention using solid phase method. The kit may also optionally include an aqueous solution and specific buffer solutions for carrying out the ligation, as well as instruction for carrying out the synthesis, and/or instructions for selection of a phosphinothiol reagent for a desired ligation. Kits are typically packaged to facilitate their use for carrying out the desired method. Kits comprise one or more reaction components individually packaged in separate containers. Kits may contain selected amounts of one or more reaction components for carrying out one or more reactions.

DETAILED DESCRIPTION OF THE INVENTION

Figure 1:
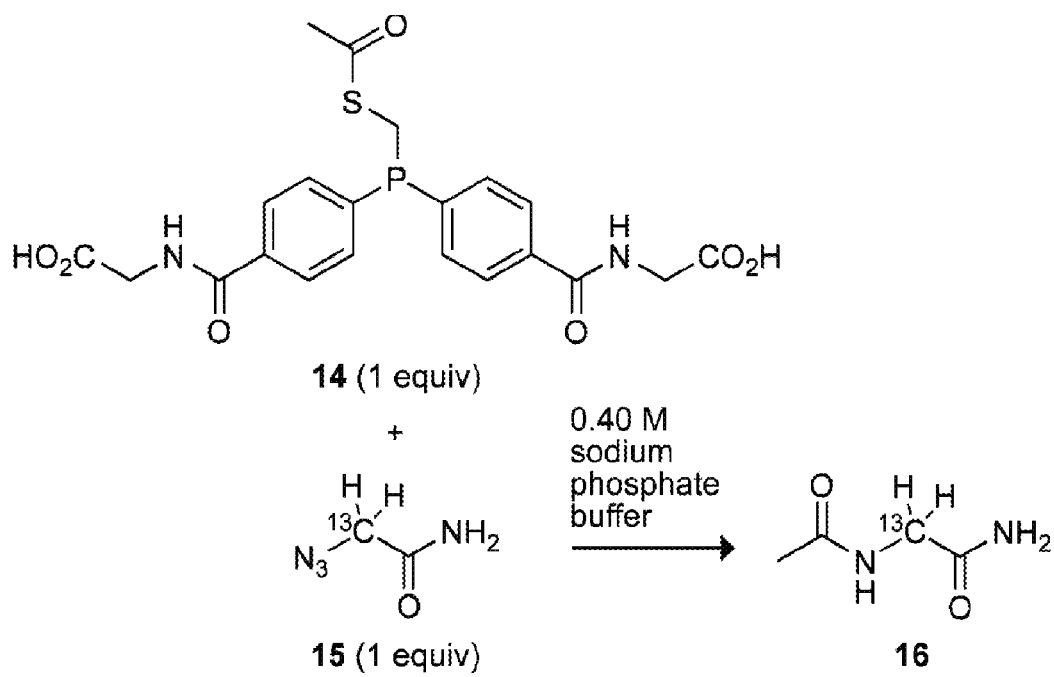
FIG. 1 illustrates dependence of the yield of amide 16 on the solution pH in a traceless Staudinger ligation mediated by an acidic phosphinothiol. Reactions were performed with equimolar amounts of 14 and 15 (0.16 M) in 0.40 M sodium phosphate buffers of varying pH. $^{13}$C-labeled glycinamide ([$^{13}$Cα]-GlyNH$_2$) is the major product of this reaction at each pH. Data are the mean values (SE) (2%) from two or three experiments.
Figure 1:
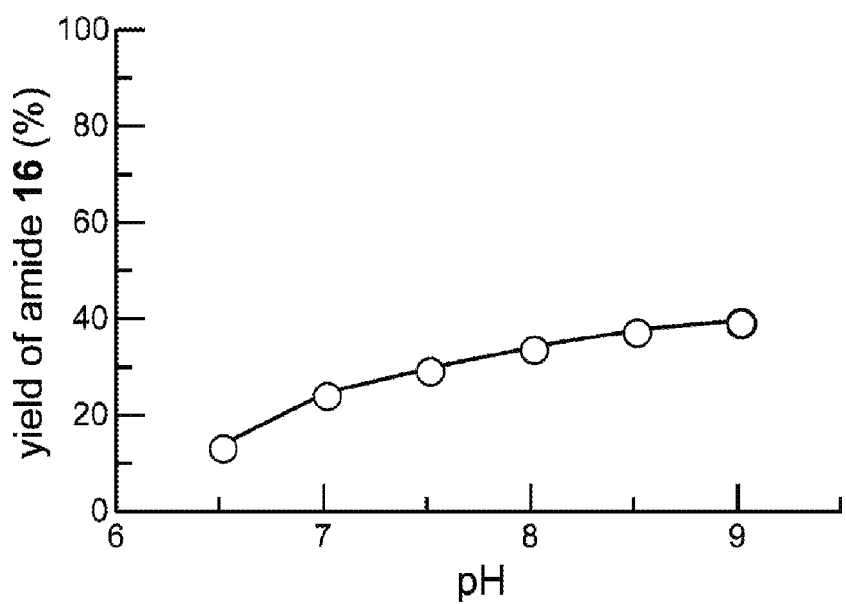

Most generally the invention relates to methods and reagents for the synthesis of an amide bond in an aqueous solution. This invention also relates to the formation of an amide bond between several key species including amino acids, peptides, and protein fragments in an aqueous solution. More specifically this invention relates to a peptide ligation in an aqueous solution.

Subject matter of the invention has been described at least in part in Tam, A. Soellner, M. B., Raines, R. T. (2007) "Water-Soluble Phosphinothiols for Traceless Staudinger Ligation and Integration with Expressed Protein Ligation," J. Amer. Chem. Soc., 129:11421-11430 and Tam, A., Raines, R.

(2009) "Coulombic effects on the traceless Staudinger ligation in water," *Bioorganic & Medicinal Chemistry* 17, 1055-1063. Additional information regarding the traceless Staudinger ligation is found in Tam, A. and "*Methods in Enzymology* 462, 25-44; and Tam, A, Soellner, M. B., and Raines, R. T. (2008) "Electronic and steric effects on the rate of the traceless Staudinger ligation," *Organic & Biomolecular Chemistry* 6, 1173-1175.)

Although not wishing to be bound by any particular mechanism, a likely mechanism for this reaction is illustrated in Scheme 2 (pathway A). The reaction begins by the formation of the phosphinothioester (VII). Most generally, the phosphinothioester can be formed by the reaction of a phosphinothiol reagent (V) with an activated carboxylic acid derivative (VI). An "activated" carboxylic acid derivative is activated for nucleophilic attack, as is understood in the art, and is exemplified by thioesters, acyl halides, acyl imidazoles, activated esters, and N-acylsulfonamides. In Scheme 2, the reaction is illustrated for ligation of two peptides, which generally may be two different peptides. The reaction may also be used, as discussed herein below, to form an amide bond between two amino acids or between an amino acid and a peptide (e.g., for synthesis of a peptide) or between an amino acid, peptide (including a protein) and a chemical species other than an amino acid or peptide (e.g., a sugar or other saccharide.) The phosphinothioester (VII) couples with the desired azide (VIII) leading to the formation of a reactive iminophosphorane (IX) and nitrogen gas. Attack of the iminophosphorane nitrogen on the thioester leads to an amidophosphonium salt (X). Hydrolysis of the amidophosphonium salt produces an amide (XI) and a phosphine oxide (XII). Path B which relates to the traceless Staudinger ligation in aqueous medium is discussed below.

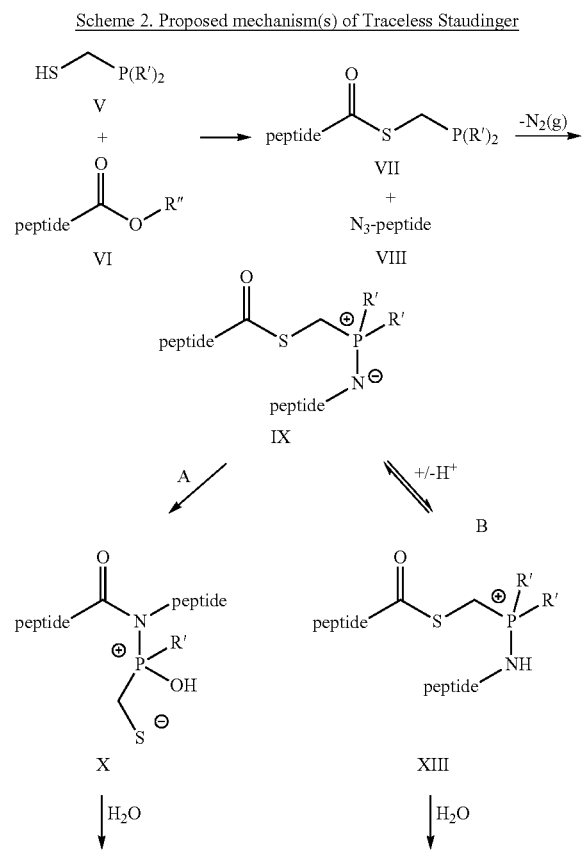

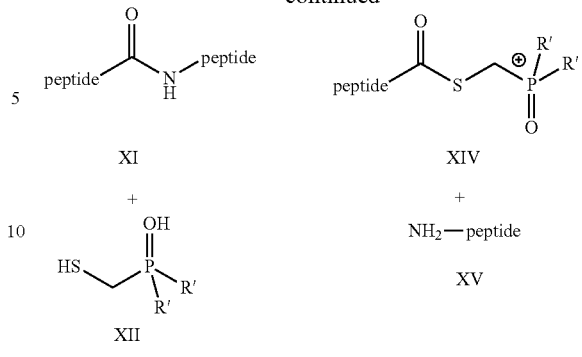

The ligation reactions of this invention are exemplified by the specific reaction of a water soluble phosphinothiol in an aqueous solution of a given pH. The term "water soluble" refers to a compound that has a practically useful level of solubility in an aqueous solution such that the concentration of the compound in solution is sufficient to carry out a given reaction on a useful scale. In specific embodiments, water-soluble phosphinothiol reagents include those that exhibit solubility of about 1 mM or more in water or in an aqueous buffer e.g., 0.4 M sodium phosphate buffer (pH 7.8). More preferably, water-soluble phosphinothiol reagents exhibit solubility of 10 mM in water or in an aqueous buffer, e.g., a 0.4 sodium phosphate buffer (pH 7.8).

The term "aqueous solution" refers to a solution where the solvent consists essentially of water. A small amount of organic solvent can be tolerated as long as the amount of such solvent does not interfere with the reaction or with the use of the reaction in a physiological environment. The term "buffer solution" relates to any buffer solution that is suitable to use for the reaction that keeps the pH in a desired range, preferably in a pH range useful for physiological environments and more specifically between 6.0-8.5. The reactions of this invention may also be carried out in miscible mixed aqueous-organic solvents, particularly where water is the predominant component of the solvent. Mixed aqueous-organic solvents include miscible mixtures of water and alcohol, where alcohols include, among others, methanol and ethanol. Miscible mixed aqueous-organic solvent systems preferably for use in this invention are those which can be used without significant detriment in a physiological environment. In specific embodiments, miscible mixed aqueous-organic solvent systems contain less than 10% by volume organic solvent. In specific embodiments, miscible mixed aqueous-organic solvent systems contain less than 5% by volume organic solvent. In specific embodiments, miscible mixed aqueous-organic solvent systems contain less than 1% by volume organic solvent.

Typically, the reaction is run at ambient pressure and temperature. The pressure may be increased or decreased as needed as long as it is not detrimental to the reaction, the starting materials, the products of the reaction or to the purpose(s) of carrying out the reaction. The temperature also can be increased or decreased to meet the needs of a specific reaction as long as the temperature used is not significantly detrimental to the reaction, the starting materials or products of reaction, or to the purpose(s) of carrying out the reaction.

The phosphinothiol reagents of this invention can be used in the form of salts. In general, any water soluble salts can be employed. In specific embodiments the salts are those that are compatible with use in a physiological environment. In specific embodiments the salts are pharmaceutically acceptable salts. Cationic phosphinothiol reagents can be used in the form of salts of any appropriate anion. Again it is preferred that salts employed in reactions herein are appropriate for use in physiological environments. In specific embodiments, the anions of such salts can include, among others, halides, carboxylates (e.g., acetate, trifluoroacetate).

Cationic phosphinothiol reagents of this invention can have one or more protonated amine groups (e.g., —$NR^3R^4H^+$ groups). Cationic phosphinothiol reagents can have one or more quaternized ammonium groups, e.g., —$NR^3R^4R_q^+$ or $NR^5R^6R_q^+$ where $R^3$, $R^4$, $R^5$ and $R^6$ have values as noted above, and $R_q$ is most generally an alkyl, alkenyl, alkynyl, heterocyclic, aryl, or heteroaryl and more specifically $R_q$ is an alkyl group. Yet more specifically, $R_q$ is an alkyl group having 1-6 carbons or 1-3 carbon atoms. $R_q$ can specifically be a methyl group. Phosphinothiol reagents of this invention can specifically contain groups —$NR^3R^4R_q^+$ or —$NR^5R^6R_q^+$ where all of $R^4$-$R^6$ and $R_q$ are alkyl groups, which may be the same or different alkyl groups. In specific embodiments, all of $R^3$-$R^6$ are alkyl groups having 1-6 carbon s or 1-3 carbons. In specific embodiments, all of $R^3$-$R^6$ are alkyl groups having 1-6 carbons or 1-3 carbons and $R_q$ is a methyl group.

The ligation herein involves the reaction of a derivatized phosphinothioester (such as VII in Scheme 2 which is shown derivatized with a peptide) and a derivatized azide (such as VIII in Scheme 2 which is shown derivatized with a peptide) to form an amide bond. The phosphinothioester can, for example, be prepared as described herein by reaction of a phosphinothiol reagent with a derivatized activated ester (such as VI in Scheme 2 which is shown derivatized with a peptide). The peptide groups of the exemplified phosphinothioesters and/or azide may be appropriately protected with art-known protecting groups. The ligation is also useful for formation of an amide bond between two amino acids by reaction of a phosphinothioester derivatized with an amino acid and an azido amino acid (each of which may be appropriately protected with art-known protecting groups). The ligation is also generally useful to ligate a peptide or a protein with an amino acid or peptide or to ligate two proteins. The ligation can also be employed to form an amide bond between an amino acid, peptide or protein group and a carbohydrate (which may be a mono-, di-, tri- or polysaccharide) or between an amino acid, peptide or protein group and a nucleoside. The ligation may also be employed to ligate an amino acid, a peptide or protein to a reporter group, tag or label (e.g., a group whose presence can be detected by optical or mass spectrometry or other instrumental method), including a fluorescent or phosphorescent group, an isotopic label or a radiolabel.

In general, the reaction functions for any ester or thioester which can be converted to the phosphinothioester and any azide. The phosphinothioester group may be formed, at the carboxy group of an amino acid or at the carboxy terminus of a peptide or protein or at an acid side group of an amino acid or one or more amino acids in a peptide or protein. The azido group may be formed, for example, at the amino group of an amino acid or at the amino terminus of a peptide or protein or at a basic side group of an amino acid or one or more amino acids in a peptide or protein.

In specific embodiments, the ligation reaction herein is employed to form an amide bond between a first amino acid, peptide or protein (or protein fragment) and a second amino acid, peptide or protein (or protein fragment). Peptides, proteins or protein fragments can be obtained by any art-known method including isolation from natural sources, expression via recombinant DNA technology or peptide synthesis (particularly solid phase peptide synthesis). Thus, the method can be used as part of a synthesis of a peptide or protein, e.g., to form an amide bond between two peptides or proteins (e.g., those formed by other methods) thus generating larger peptides or proteins. The method can also be used to generate a selected peptide by initial formation of a dipeptide followed by sequential addition of amino acids to the growing peptide. In this method, the growing peptide can be covalently attached to a solid phase (e.g., a resin) to provide for solid phase peptide synthesis.

Methods for preparation of azides for use in the methods herein are known in the art. For example, azido derivatives of amino acids can be prepared by known methods (Lundquist, J. T., and Pelletier, J. C. (2001) "Improved solid-state peptide synthesis method utilizing alpha-azide-protected aminoacids. Org. Lett. 3:781-783.) In specific embodiments, the invention can be practiced with azido derivatives of any of the proteinogenic (or standard) L-amino acids, including L-selenocysteine and L-pyrrolylysine. Methods for formation of azido derivatives of peptides and proteins are known in the art. (See Tam, A., and Raines, R. T. (2009) Methods Enzymol. 462:25-44, and references therein.) An azido peptide can, for example, be formed via solid phase peptide synthesis. Phosphinothioesters of amino acids, peptides and proteins can be prepared as described herein employing the phosphinothiol reagents of this invention. The phosphinothiol regents herein are particularly useful for the formation of phosphinothioesters in aqueous solution.

The ligation as exemplified herein can be used to produce a peptide or a protein. Peptides can be synthesized in aqueous solutions by repeated cycles of ligation to formamide bonds between amino acids. In a specific embodiment peptide synthesis can be implemented using solid phase methods in which one of the amino acids is covalently attached to a solid support or resin. A variety of resins are available in the art for use in combination with the ligation method of this invention. Solid support materials, e.g., resin, appropriate for use in aqueous solutions as are employed in the ligations of this invention are known in the art and one of ordinary skill in the art can readily select support materials that are compatible with the synthetic steps to be performed. It will be appreciated in the art of peptide synthesis that it may be necessary to protect functional groups on amino acids and peptides during the ligation reaction of this invention. Various protecting groups for amino acid and peptide side groups, carboxyl termini and amino termini are well-known in the art and one of ordinary skill in the art knows how to select appropriate protecting groups for a given amino acid or peptide functional group for the conditions herein without undue experimentation.

The term "alkyl" refers to a monoradical of a branched or unbranched saturated hydrocarbon and to cycloalkyl groups having one or more rings. Unless otherwise indicated preferred alkyl groups have 1 to 30 carbon atoms and more preferred are those that contain 1-22 carbon atoms. Short alkyl groups are those having 1 to 6 carbon atoms including methyl, ethyl, propyl, butyl pentyl and hexyl groups, including all isomers thereof. Long alkyl groups are those having 8-30 carbon atoms and preferably those having 12-22 carbon atoms as well as those having 12-20 and those having 16-18 carbon atoms. Alkyl groups herein include those having 1-3 carbons, those having 4-8 carbons, those having 4-10 carbons and individually those having 1, 2, 3, 4, 5, 6, 7, 8, 9 or 10 carbons. The term "cycloalkyl" refers to cyclic alkyl groups having preferably 3 to 30 carbon atoms having a single cyclic ring or multiple condensed rings. Cycloalkyl groups include, by way of example, single ring structures such as cyclopropyl, cyclobutyl, cyclohexyl and the like, or multiple ring structures such as adamantanyl, and the like. Cycloalkyl groups include those having a single 3-6-member ring, those having a single 5-8-member rings, those having two 3-8 member fused rings, and those having two 3-6-member fused rings. Cycloalkyl groups include those that are substituted with one or more alkyl groups (e.g., methylcyclohexyl groups) as well as alkyl groups substituted with cycloalkyl rings (e.g., methylenecyclohexyl).

The term "alkenyl" refers to a monoradical of a branched or unbranched unsaturated hydrocarbon group and to cycloalkenyl groups having one or more rings wherein at least one ring contains a double bond. Unless otherwise indicated preferred alkyl groups have 1 to 30 carbon atoms and more preferred are those that contain 1-22 carbon atoms. Alkenyl groups may contain one or more double bonds (C=C) which may be conjugated or unconjugated. Preferred alkenyl groups are those having 1 or 2 double bonds. Short alkenyl groups are those having 2 to 6 carbon atoms including, ethenyl, propenyl, butenyl pentenyl and hexenyl groups, including all isomers thereof. Long alkenyl groups are those having 8-30 carbon atoms and preferably those having 12-22 carbon atoms as well as those having 12-20 and those having 16-18 carbon atoms. Alkenyl groups herein include those having 2-3 carbons, those having 4-8 carbons, those having 4-10 carbons and individually those having 2, 3, 4, 5, 6, 7, 8, 9 or 10 carbons. The term "cycloalkenyl" refers to cyclic alkenyl groups of form 3 to 30 carbon atoms having a single cyclic ring or multiple condensed rings in which at least one ring contains a double bond (C=C). Cycloalkenyl groups include, by way of example, single ring structures such as cyclopropenyl, cyclobutenyl, and cyclopentenyl, cyclohexenyl and the like, or multiple ring structures such as adamantanenyl, and the like. Cycloalkenyl groups include those having a single 3-6-member ring, those having a single 5-8-member rings, those having two 3-8 member fused rings, and those having two 3-6-member fused rings. Cycloalkenyl groups include those that are substituted with one or more alkyl groups as well as alkyl groups substituted with cycloakenyl rings (e.g., methylenecyclohexenyl).

The term "alkynyl" refers to a monoradical of an unsaturated hydrocarbon having one or more triple bonds. Unless otherwise indicated preferred alkynyl groups have 2 to 30 carbon atoms and more preferred are those that contain 2-22 carbon atoms. Alkynyl groups include ethynyl, propargyl, and the like. Alkynyl groups herein include those having 2-3 carbons, those having 4-8 carbons, those having 4-10 carbons and individually those having 2, 3, 4, 5, 6, 7, 8, 9 or 10 carbons. Alkynyl groups preferably have 1 triple bond.

The term "aryl" refers to a group containing an unsaturated aromatic carbocyclic group having from 6 to 22 carbon atoms having a single aromatic ring, more than one carbon rings of which one ring is aromatic, or multiple condensed rings, wherein at least one ring is aromatic. Aryls include phenyl, naphthyl, biphenyl and the like. Aryl groups may contain portions that are alkyl, alkenyl, or alkynyl in addition to the unsaturated aromatic ring(s), e.g., alkyl substituted phenyls (e.g., benzyl) or aryl substituted alkyl groups (phenylmethyl). Preferred aryl groups are not charged groups.

The term "heteroaryl" refers to an aromatic group of from 2 to 22 carbon atoms having 1 to 4 heteroatoms in an aromatic ring wherein the heteroatom is preferably selected from oxygen, nitrogen, and sulfur within at least one ring. Heteroaryl groups include those having 2-5 carbon atoms, those having 2-10 carbon atoms and those having 2-15 carbon atoms along with one, two, three or four heteroatoms. In specific embodiments, heteroaryl groups include those having one, two or three nitrogens, those having one or two oxygens, those having one or two sulfurs, those having both oxygen and nitrogen. Heteroaryl groups include among others furanyl, pyridyl, pyrimidinyl, pyrrolyl, purinyl, imidazolyl, pyrazolyl, oxazolyl, thienyl, benzimidazolyl, or benzofuranyl. Heteroaryl groups include those have one 5- or 6-member ring with one or two heteroatoms, and those having two 5- or 6-member rings with at least one ring having one or two heteroatoms.

The term "heterocyclic" refers to a cyclic structure of from 2 to 22 carbons atoms having 1 to 4 heteroatoms selected from oxygen, nitrogen, and sulfur within at least one ring. Heterocyclic groups include those having 2-5 carbon atoms, those having 2-10 carbon atoms and those having 2-15 carbon atoms along with one, two, three or four heteroatoms. In specific embodiments, heterocyclic groups include those having one, two or three nitrogens, those having one or two oxygens, those having one or two sulfurs, and those having both oxygen and nitrogen. Heterocyclic groups include, among others, piperidyl, piperazinyl, morpholinyl, tetrahydropyranyl, pyranyl, and dioxanyl groups.

Alkyl, alkenyl, alkynyl, aryl, heteroaryl, and heterocyclic groups herein are optionally substituted with one or more chemical groups other than hydrogens. Substitution unless otherwise specified includes substitution with one or more halogens, haloalkyl, oxy (=O), alkyl, alkenyl, alkynyl, aryl, heteroaryl or heterocycyl, —OR, —COR, —COOR, —O—COR, —CON(R)$_2$, —O—CON(R)$_2$, —N(R)$_2$, —NRCOR, —NRCOOR, —SR, or —S—COR groups where each R is independently selected from a hydrogen or an alkyl, alkenyl, alkynyl, heterocyclic, aryl or heterocyclic group which in turn is optionally substituted with one or more halogens, oxy (=O), haloalkyl, alkyl, alkenyl, alkynyl, aryl, heteroaryl, heterocycyl, —OH, —COH, —COCH$_3$, —COOH, —COORs, —O—COH, —CON(H)$_2$, —CON—O—CON(H)$_2$, —CON(R$_S$)$_2$, —CON—O—CON(R$_S$)$_2$ or —N(R$_S$)$_2$ groups, where R$_S$ is and alkyl, alkenyl, alkynyl, aryl, heteroaryl or heterocycyl group. In specific embodiments, R is hydrogen, an unsubstituted alkyl group having 1-6 carbons or 1-3 carbons or a phenyl group. In specific embodiments, substituents include those having from 1-3 carbon atoms. In specific embodiments, groups herein carry 1, 2, 3, 4, 5 or 6 substituents.

The term "alkylene" refers to a biradical of a linear or branched saturated alkyl chain and may contain a cyclic alkyl group. This term is exemplified by groups such as methylene (—CH$_2$—), ethylene (—CH$_2$CH$_2$—), more generally —(CH$_2$)$_p$—, where n is an integer indicating the length of the chain. Mores specifically p is 1-10 or more preferably 1-6 or p is 2, 3 or 4. Alkylene groups may be branched. Alkylene groups may be optionally substituted. Alkylene groups may have up to two non-hydrogen substituents per carbon atoms. Preferred substituted alkylene groups have 1, 2, 3 or 4 non-hydrogen substituents. Cycloalkylene groups refers to a biradical derived from a cycloalkyl group or an alkyl substituted cycloalkyl group. Cycloalkylene groups include alkylene groups in which a CH$_2$ moiety of the alkylene chain is replaced with a cycloakyl group, e.g., a 1,2-cyclopropylene, a 1,3-cyclobutylene, a 1,3-cyclopentylene, a 1,2-cyclpentylene, a 1,3-cyclohexylene, or a 1,4-cyclohexylene group. For example, cycloalkylene groups include:

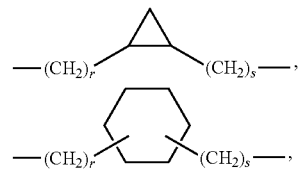

where r and s are 0 or integers ranging from 1-5,

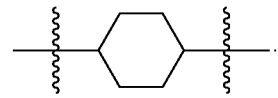

The term "heterocyclene" refers to a biradical derived from a heterocyclic group (such as piperidine, piperazine, pyrrolidene, tetrahydropyran, morpholine or the like) and an alkyl substituted heterocyclic group. Heterocylene groups include alkylene groups in which a $CH_2$ moiety of the alkylene chain is replaced with a heterocyclic group.

The term "arylene" refers to the biradical derived from an aryl group (including a substituted aryl group) as defined above and is exemplified by 1,2-phenylene, 1,3-phenylene, 1,4-phenylene, 1,2-naphthylene and the like as well as substituted derivatives thereof. The term "heteroarylene" similarly refers to the biradical derived from a heteroaryl group (including a substituted aryl group) as defined above.

Alkylene, cycloalkylene, arylene, heterocyclene, and heteroarylene groups herein are optionally substituted as described generally herein. In specific embodiments, alkylene groups and cycloalkylene groups can be substituted with one or more —OH, halogen atoms, alkyl groups or alkoxy groups, particularly alkyl or alkoxy groups having 1-3 carbon atoms. In specific embodiments, aryl, heterocyclene, and heteroaryl groups can be substituted on a ring with one or more halogens, alkyl groups, alkoxy groups or OH groups, particularly alkyl and alkoxy groups having 1-3 carbon atoms.

In the $R^1$ and $R^2$ linker groups herein one or more non-neighboring —$CH_2$— groups can be replaced with O, S, CO, an ester, an amide —NR"—CO—, or an N(R") group, where R" is hydrogen or an optionally substituted alkyl, alkenyl, alkynyl, heterocyclic, aryl or heterocyclic group. In specific embodiments, R" is hydrogen or an alkyl group having 1-6 carbons or 1-3 carbons.

Functional groups in the reagents of this invention can be protected with protecting groups appropriate for the functional group which is to be protected and for the reactions in which the reagent is to be employed. A variety of protecting groups are known in the art for various functional groups which may be reactive under a given set of reaction conditions. One of ordinary skill in the art in view of what is known in the art regarding protecting groups can select a protecting group appropriate for a given functional group under a given set of reaction conditions. Conditions for selective removal of a given protective group on a given reagent are known in the art and can be employed by one of ordinary skill in the art.

The reagents of this invention can be synthesized by one of ordinary skill in the art in view of descriptions provided herein and what is generally well known in the art without resort to undue experimentation.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure. Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art. Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term comprising is intended to encompass the narrower consisting essentially of and the even narrower consisting of: Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of." The invention illustratively described herein suitably may be practiced in the absence of any element or elements, limitation or limitations which is not specifically disclosed herein.

One of ordinary skill in the art will appreciate that starting materials, catalysts, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

THE EXAMPLES

Example 1

(Diphenylphosphino)methanethiol (1) is the most efficient known phosphinothiol for ligating peptides to form a junction at a glycine residue. (Nilsson, B. L.; Kiessling, L. L.; Raines, R. T. *Org. Lett.* 2001, 3, 9-12; Soellner, M. B.; Nilsson, B. L.; Raines, R. T. *J. Am. Chem. Soc.* 2006, 128, 8820-8828.) Recently, the p-methoxy-substituted phosphinothiol 2 was shown to afford high yields at non-glycyl residues. (Soellner, M. B.; Tam, A.; Raines, R. T. *J. Org. Chem.* 2006, 71, 9824-9830.)

Although they have desirable attributes, neither of these phosphinothiols is soluble in water. Indeed, all traceless Staudinger ligations have been performed in organic solvents or organic/aqueous mixtures. The ability to effect the traceless Staudinger ligation in water expands the utility of the Staudinger ligation. In particular, the possibility of carrying out transthioesterification with a water-soluble phosphinothiol would enable the generation of phosphinothioesters at the C terminus of proteins generated by expressed protein ligation. That ability would overcome the requirement for a cysteine residue at the ligation junction. (Liu, L.; Hong, Z. Y.; Wong, C. H. *Chem. Bio Chem.* 2006, 7, 429-432.)

This invention provides water-soluble phosphinothiol reagents that enable the first traceless Staudinger ligations in water. Additionally, it is demonstrated that water-soluble phosphinothiols can be integrated with expressed protein ligation to generate an intact protein with a C-terminal phosphinothioester, poised for Staudinger ligation.

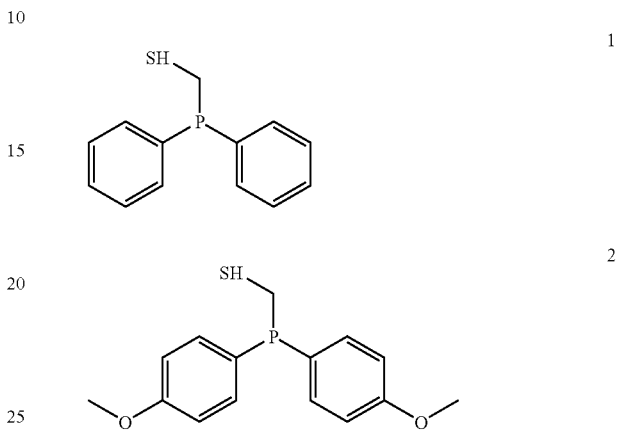

The bis(p-carboxyphenyl) phosphinomethanethiol 3 was first explored as a water-soluble phosphinothiol. The aryl groups of phosphinothiols 1 and 2, increase the yield of peptide ligations, (Nilsson, B. L.; Soellner, M. B.; Raines, R. T. In *Chemical Probes in Biology* (*NATO ASI Series*); Schneider, M. P., Ed.; Kluwer Academic: Boston, Mass., 2003; pp 359-369) while adding two hydrophilic carboxyl groups should increase water-solubility. The synthetic route to phosphinothiol 3 is shown in Scheme 3. Briefly, Grignard reagent 4 was added to (chloromethyl)-phosphonic dichloride to yield diester 5. Potassium thioacetate displacement of the chloro group gave thioester 6 in high yield. Its phosphine oxide group was reduced with excess trichlorosilane, and its two carboxyl groups were unmasked with trifluoroacetic acid. Finally, deprotection of the thiol group was achieved in basic MeOH to give phosphinothiol 3 in 23% overall yield.

Scheme 3. Route for the synthesis of Acidic Phosphinothiol 3

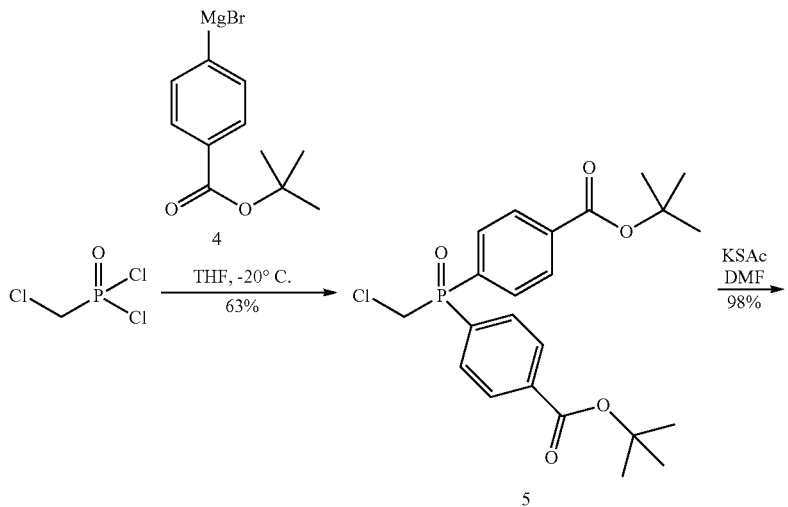

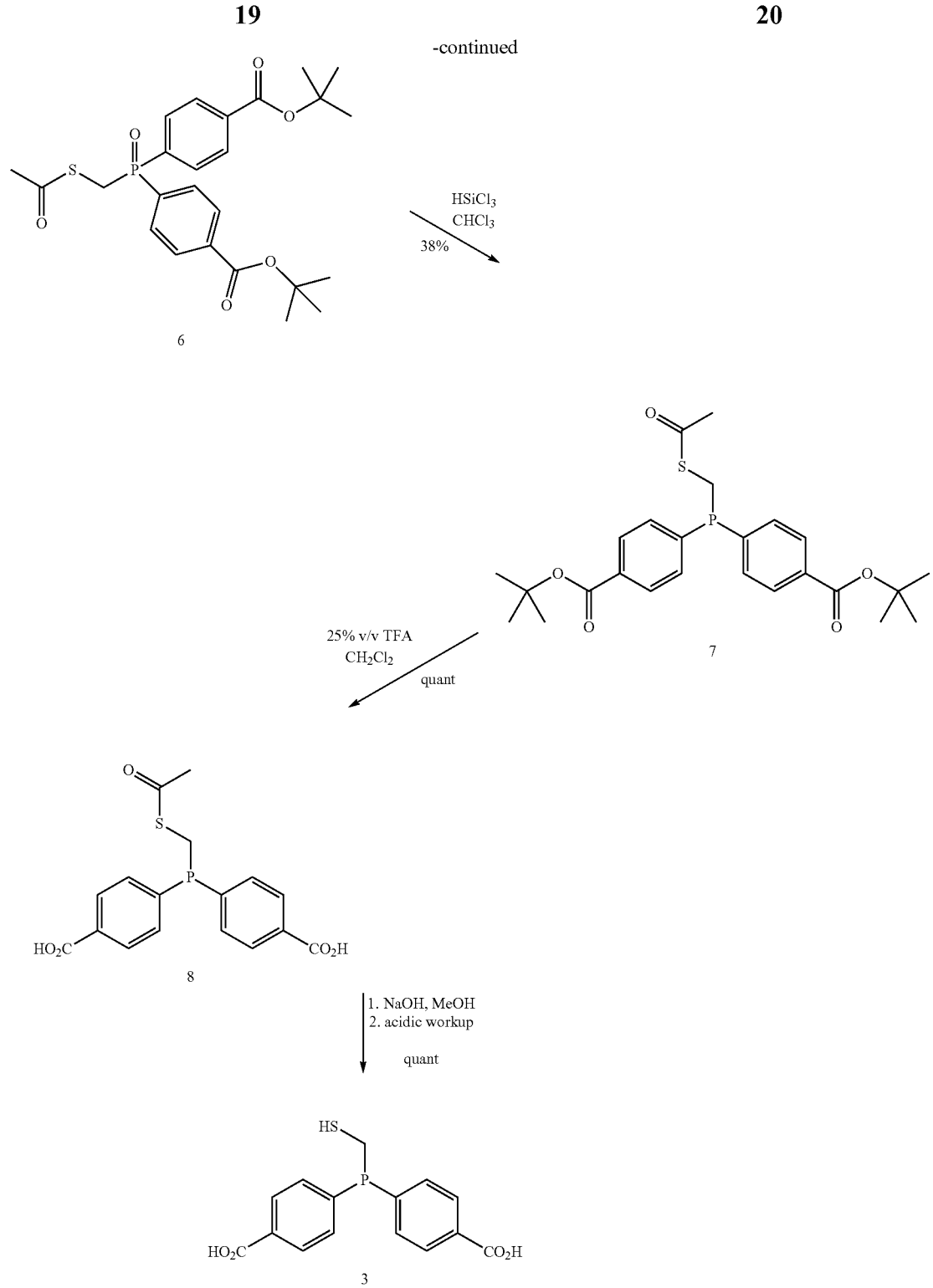

However, phosphinothiol 3 was found to be barely soluble in water, remaining as a viscous residue that was unable to mediate a traceless Staudinger ligation. Noting that hippuric acid is more soluble than benzoic acid, (Windholz, M., Budavari, S., Blumetti, R. F., Otterbein, E. S., Eds. *The Merck Index: An Encyclopedia of Chemicals, Drugs, and Biologicals*, 10th ed.; 1983; entry 4611), an attempt to increase the water solubility of phosphinothiol 3 was made by condensing it with glycine which has two carboxyl groups. The synthetic route to phosphinothiol 9 is shown in Scheme 4. Briefly, cleavage of the esters in diester 5, followed by treatment with excess thionyl chloride, generated the diacid chloride. Reaction with glycine t-butyl ester gave diamide 11, which was carried on as in Scheme 3 to give phosphinothiol 9 in 33% overall yield.

Scheme 4. Route for the synthesis of Acidic Phosphinothiol 9

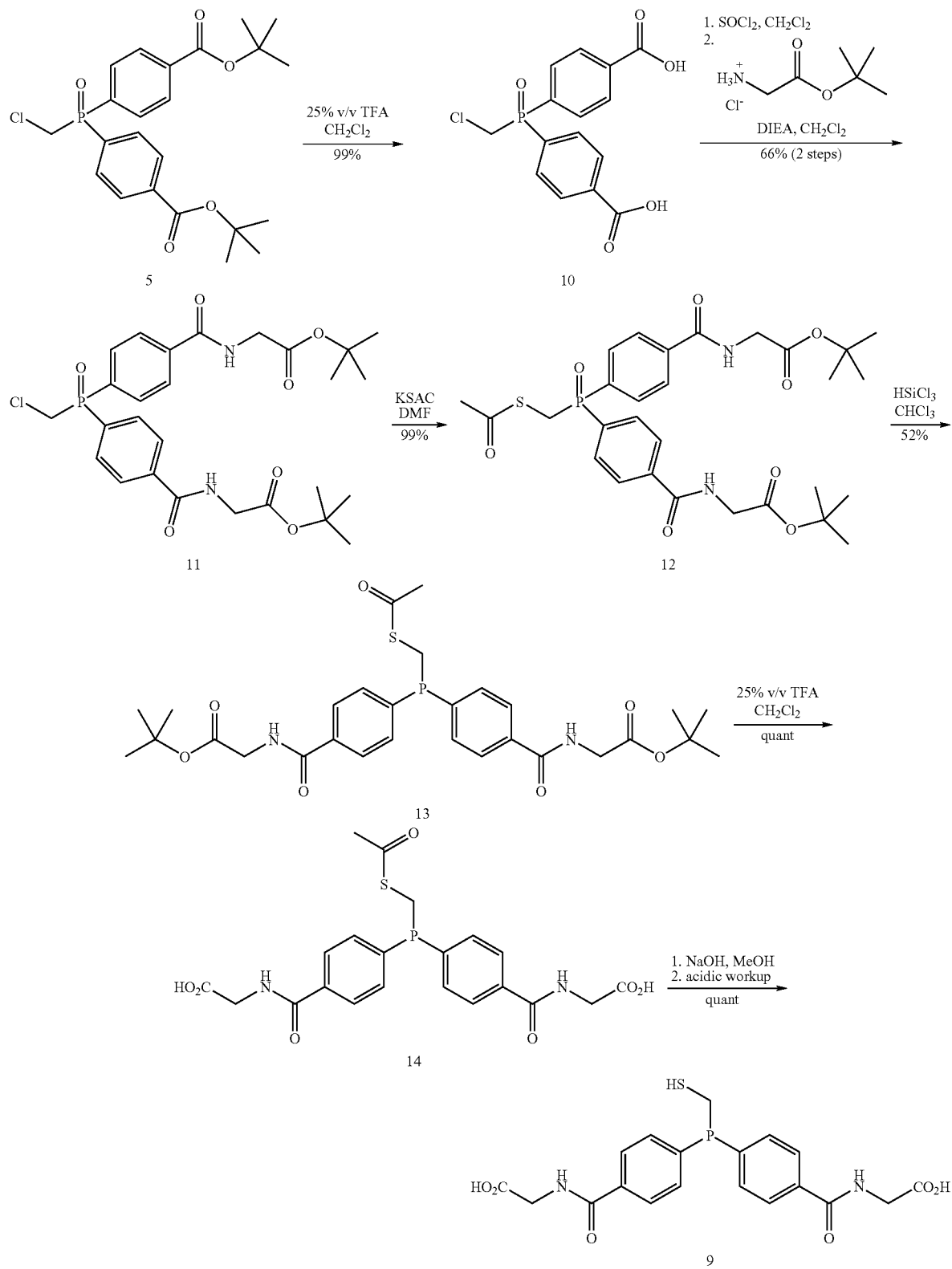

The solubility of phosphinothiol 9 was found to be greater than that of phosphinothiol 3, approaching 50 mM in 0.4 M sodium phosphate buffer (pH 7.8). The utility of phosphinothiol 9 was determined by monitoring its ability to mediate a traceless Staudinger ligation in water with a $^{13}$C NMR assay developed in our laboratory.

The major product of the reaction of phosphinothioester 14 with azide 15 (FIG. 1) was the amine byproduct, glycinamide, which is formed by the reduction of the azido group. The yield of the desired product, amide 16, was strongly dependent on the pH of the reaction mixture, increasing at high pH (FIG. 1). Accordingly, a means of achieving a high yield would be to perform reactions with phosphinothiol 9 at high pH. Unfortunately, the hydrolysis of thioesters is rapid at high pH. (Noda, L. H.; Kuby, S. A.; Lardy, H. A. *J. Am. Chem. Soc.* 1953, 75, 913-917.) In addition, it would be desirable to perform traceless Staudinger ligations near neutral pH, where proteins themselves tend to be most stable.

The pH dependence of amide formation in the reaction of phosphinothioester 14 with azide 15 suggested that a key atom must be unprotonated to effect the traceless Staudinger ligation in water. Without wishing to be bound by a particular theory, it is believed that to effect traceless Staudinger ligation in water that the nitrogen of the iminophosphorane must be protonated.

Path A in Scheme 2, above, shows the putative mechanism for a typical Staudinger ligation to form an amide product. In a protic solvent, the nitrogen of the iminophosphorane could become protonated, as in Path B. That protonation would prevent the desired S→N acyl transfer, as well as make the adjacent phosphorus more electrophilic. The attack of water on that phosphorus would ultimately lead to the amine byproduct XV (Path B). Like the iminophosphorane phosphorus, the thioester carbon becomes more electrophilic and hence susceptible to hydrolysis upon protonation of the iminophosphorane. Thioester hydrolysis would decrease the yield of the amide in a pH-dependent manner and is thus consistent with the data in FIG. 1.

These two possible mechanisms were further investigated using intramolecular Coulombic interactions to modulate the acidity of the iminophosphorane intermediate. (Kirkwood, J. G.; Westheimer, F. H. *J. Chem. Phys.* 1938, 6, 506-512. Kirkwood, J. G.; Westheimer, F. H. *J. Chem. Phys.* 1938, 6, 513-517.) Specifically, bis(p-dimethylaminoethyl) phosphinomethanethiol (17) was synthesized which has dimethyl amino groups that could not only impart water solubility, but also (when protonated) serve to discourage protonation of the iminophosphorane nitrogen. Tertiary amino groups, in contrast to primary or secondary amino groups, were selected to obviate intramolecular S→N acyl transfer in ensuing thioesters.

The synthetic route to phosphinothiol 17 is shown in Scheme 5. Briefly, 4-bromophenethyl alcohol was converted to mesylate 18, and then amine 19. Addition of its Grignard reagent to diethyl phosphite gave phosphine oxide 20 in moderate yields. Phosphine oxide 20 was reduced by treatment with diisobutyl aluminum hydride (DIBAl-H) (Busacca, C. A.; Lorenz, J. C.; Grinberg, N.; Haddad, N.; Hrapchak, M.; Latli, B.; Lee, H.; Sabila, P.; Saha, A.; Sarvestani, M.; Shen, S.; Varsolona, R.; Wei, X. D.; Senanayake, C. H. *Org. Lett.* 2005, 7, 4277-4280) and then reacted with borane to protect the phosphino group from oxidation. (Three equivalents of borane was required due to its high affinity for the two amino groups.) Complexation with borane was otherwise beneficial, making compounds 21-24 less polar and hence easier to purify. Phosphine-borane complex 21 was reacted with formaldehyde to generate alcohol 22, which was converted to mesylate 23 and then reacted with potassium thioacetate to yield protected phosphinothioester 24. 1,4-Diazabicyclo [2.2.2]-octane (DABCO; 3 equiv) was used to remove the borane groups. Deprotection of the thiol group was achieved in basic MeOH, followed by acidification in 4 N HCl/dioxanes to give phosphinothiol 17 in 17% overall yield. As a chloride salt, phosphinothiol 17 was an easy-to-handle, odor-free white solid that was stable in air for several days and soluble at >1 M in 0.4 M sodium phosphate buffer (pH 7.8).

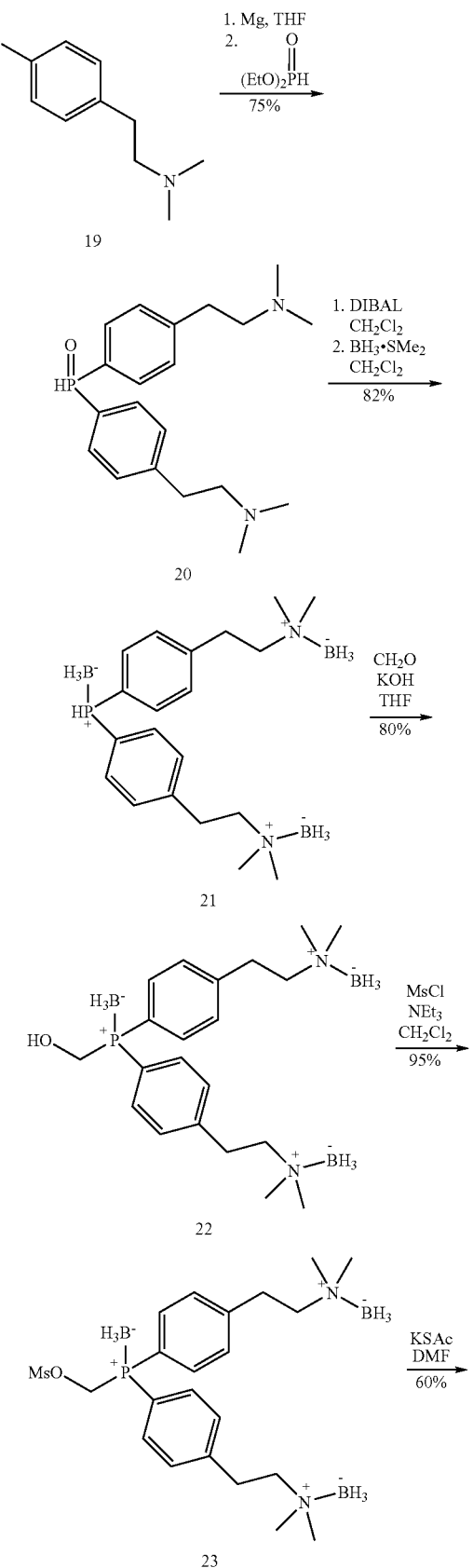

Scheme 5. Route for the Synthesis of Basic Phosphinothiol 17.

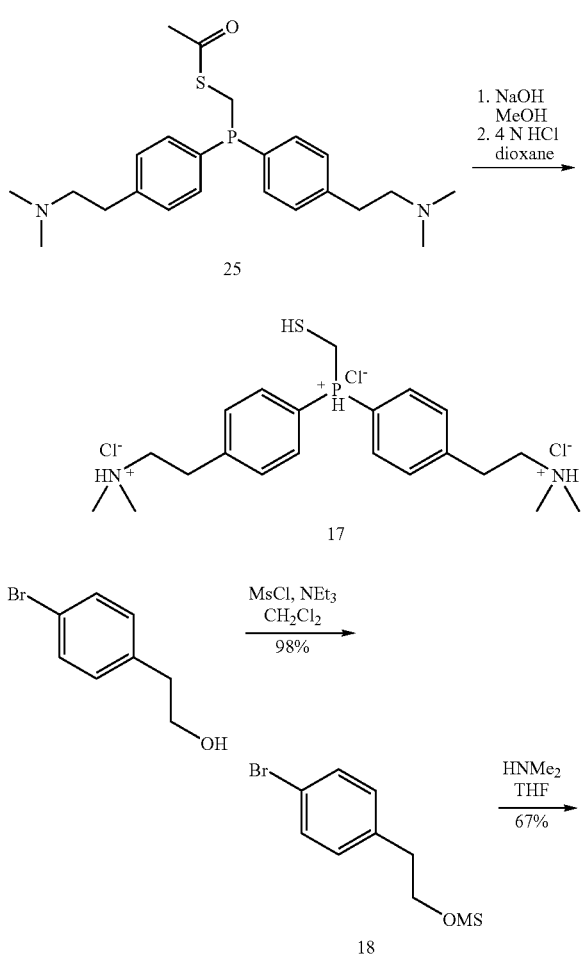

Figure 2:
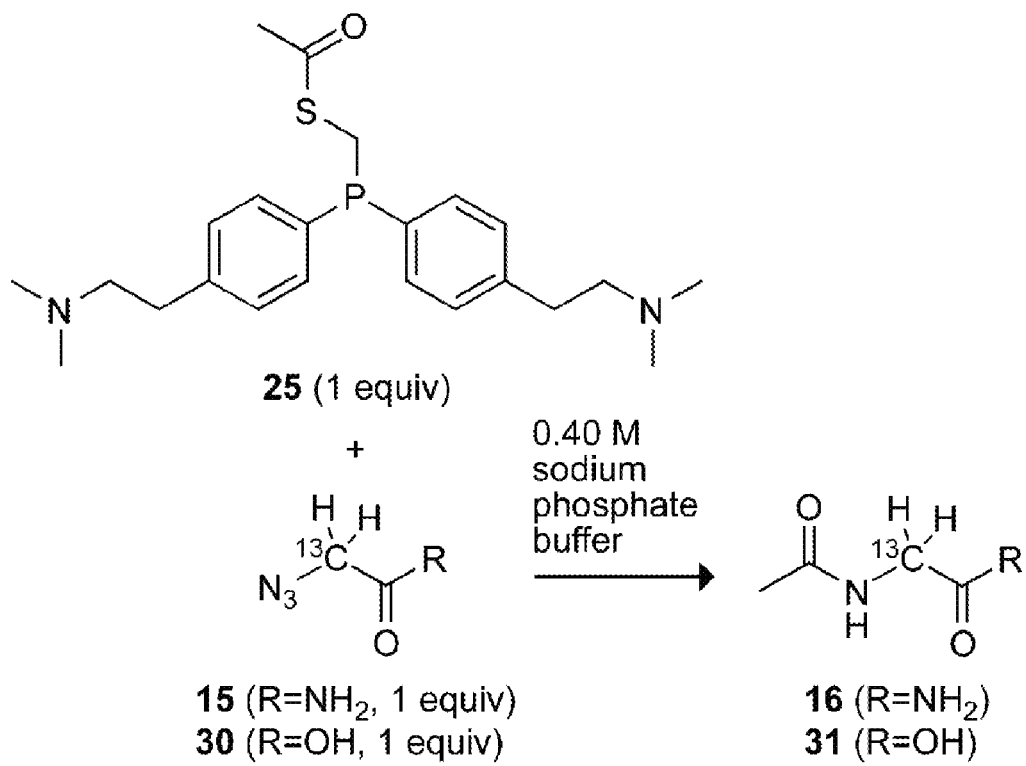
FIG. 2 illustrates the dependence of amide yield on the solution pH in a traceless Staudinger ligation mediated by a basic phosphinothiol. Reactions were performed with equimolar amounts of 25 and 15 (or 30) (0.16 M) in 0.40 M sodium phosphate buffers of varying pH. Data are the mean values (SE=±2%) from two or three experiments.
Figure 2:
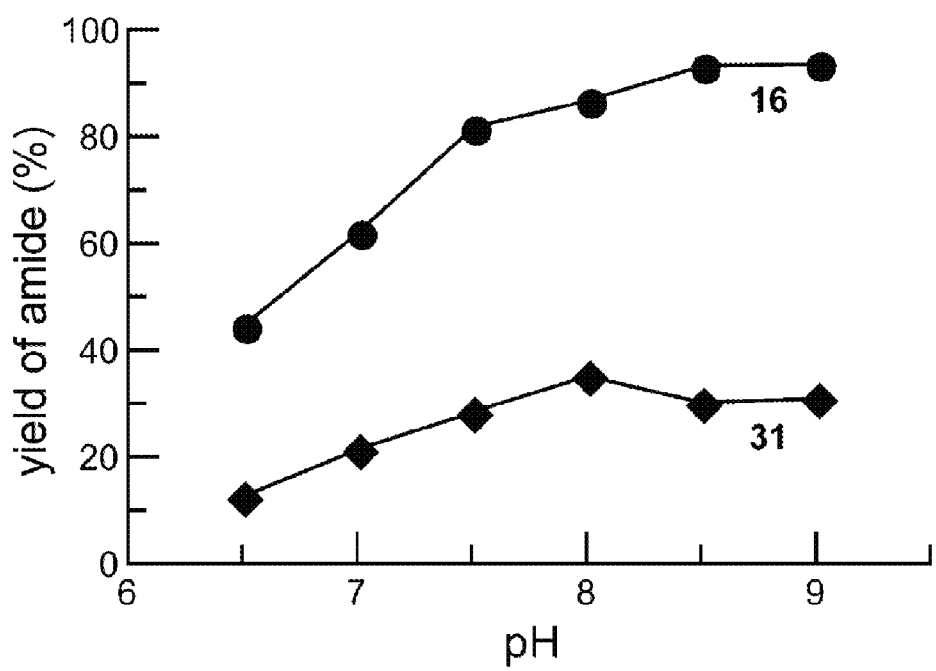

The ability of phosphinothiol 17 to mediate a traceless Staudinger ligation in water was evaluated. As with phosphinothiol 9, phosphinothiol 17 provided amide 16 with a yield that was dependent on the pH of the reaction mixture, increasing at high pH (FIG. 2). At each pH, however, the ligation yield with basic phosphinothiol 17 was much greater than that with acidic phosphinothiol 9, consistent with consideration of the relevant Coulombic interactions. It is noteworthy that the yields with phosphinothiol 17 reached 94% at high pH and exceeded 80% in all solutions with pH $\geqq 7.5$. Moreover, these yields are for reactions performed with equimolar reactants, which contrasts with the auspicious excess of nucleophile typically used in solid-phase peptide synthesis, native chemical ligation, and expressed protein ligation.

Phosphinothiol 17 is not only cationic rather than anionic, but also has a different type of substituent in the para position than does phosphinothiol 9. The Hammett constants for a secondary amide and a protonated dimethylaminoethyl group are $\sigma_p=0.36$ and 0.14, respectively. (Hammett, L. P. Chem. Rev. 1935, 17, 125-136. Hammett, L. P. Physical Organic Chemistry: Reaction Rates, Equilibria, and Mechanisms; McGraw-Hill: New York, 1940. Hansch, C.; Leo, A.; Taft, R. W. Chem. Rev. 1991, 91, 165-195.) A higher $\sigma_p$ value (like a positive charge) would serve to decrease the pKa of the iminophosphorane nitrogen. Despite this favorable attribute, phosphinothiol 9 is still an inferior reagent than is phosphinothiol 17, indicating that Coulombic effects are more important than inductive and resonance effects in the ability of phosphinothiols 9 and 17 to mediate the traceless Staudinger ligation in water.

Figure 3:
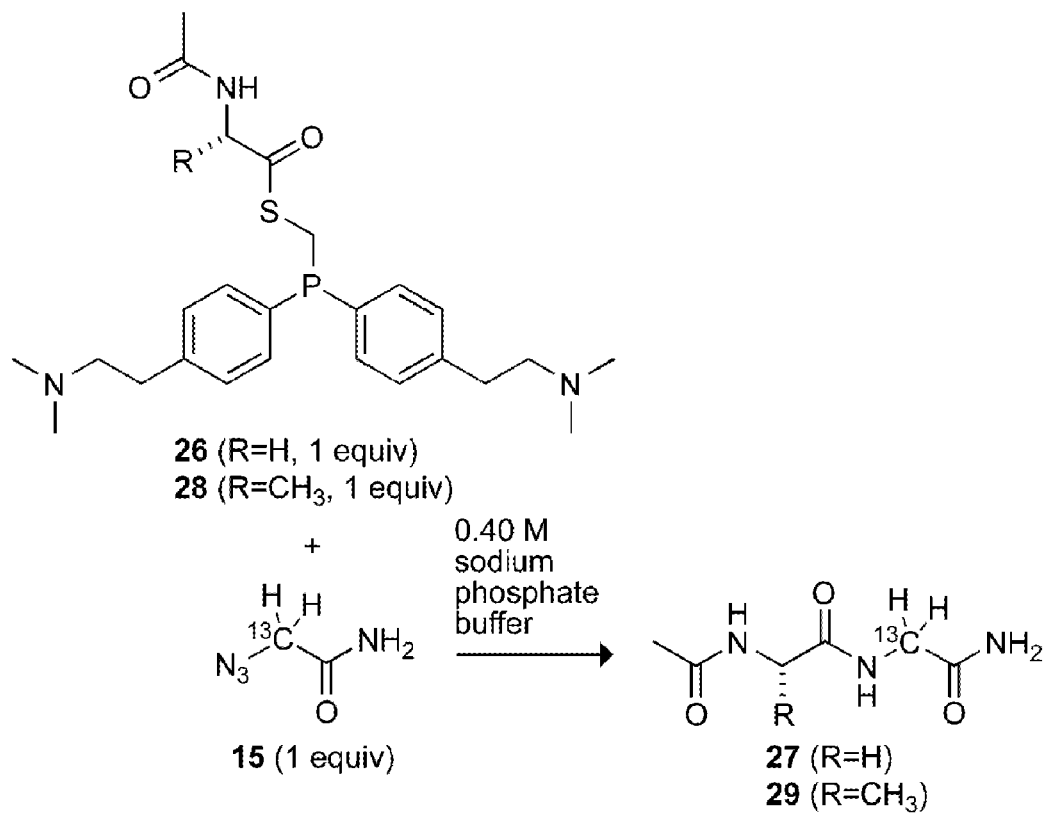
FIG. 3 illustrates the dependence of peptide yield on the solution pH in a traceless Staudinger ligation mediated by a basic phosphinothiol. Reactions were performed with equimolar amounts of 26 (or 28) and 15 (0.16 M) in 0.40 M sodium phosphate buffers of varying pH. Data are the mean values (SE=±2%) from two or three experiments.
Figure 3:
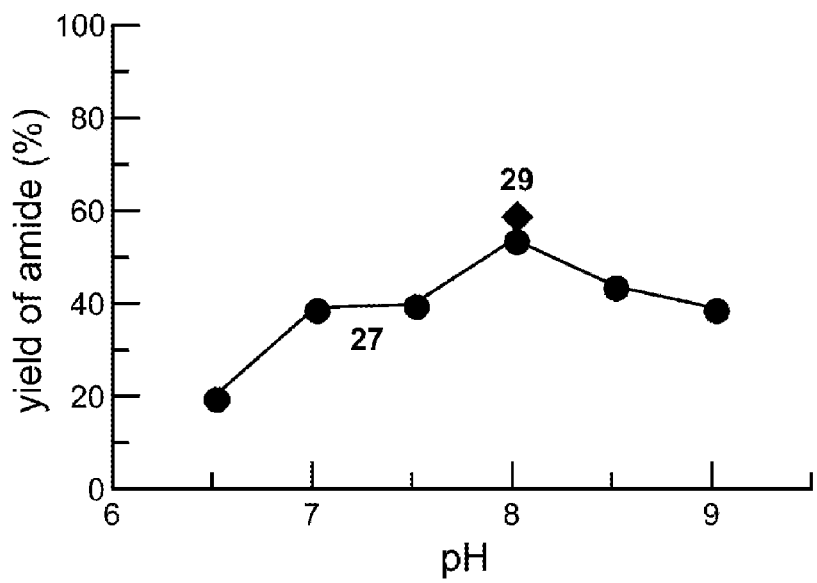

The efficacy of phosphinothiol 17 for Staudinger ligation to form peptides in water was determined. Phosphiniothiol 17 was condensed with N-acetyl glycine by standard methods using DIC and HOBt. Yields for the ligation of the resulting phosphinothioester 26 and azide 15 (FIG. 3) exceeded 50% at pH 8, but diminished somewhat at higher pH (FIG. 3). This decrease and the concomitant increase in the formation of the glycinamide byproduct could arise from hydrolysis of the thioester group of 26 to regenerate phosphinothiol 17, which could reduce azide 15.

The efficacy of the traceless Staudinger ligation in water using phosphinothiol 17 is not limited to the ligation of two glycyl residues. Phosphinothiol 17 was condensed with N-acetyl alanine by standard methods using DIC and HOBt to give phosphinothioester 28 and then reacted with azide 15 in 0.40 M sodium phosphate buffer at pH 8.0, which produced a high yield in the Gly+Gly coupling. The yield of amide 29 in this Ala+Gly coupling was 59%, which is similar to that observed in the Gly+Gly coupling (FIG. 3). Thus, the yield of the traceless Staudinger ligation in water was not diminished by the additional steric encumbrance imposed by a non-glycyl residue.

The traceless Staudinger ligation mediated by phosphinothiol 17 is expeditious in water. An NMR-based assay (Soellner, M. B.; Nilsson, B. L.; Raines, R. T. J. Am. Chem. Soc. 2006, 128, 8820-8828; Soellner, M. B.; Tam, A.; Raines, R. T. J. Org. Chem. 2006, 71, 9824-9830) was used to monitor the rate of the reaction of phosphinothioester 28 and azide 15. This Ala+Gly coupling was found to proceed with a second-order rate constant of k2) $7.4\times10^{-3}$ $M^{-1}$ $s^{-1}$ in water. This rate constant, which is similar to that reported previously for a Gly+Gly coupling mediated by phosphinothiol 1 in DMF/D2O (6:1) (k2) $7.7\times10^{-3}$ $M^{-1}$ $s^{-1}$), corresponds to $t_{1/2}=10$ min for a reaction with 0.16 M azide.

Having a proximal negative charge on the azide rather than the phosphinothioester also has deleterious consequences. We found that the Staudinger ligation with azide 30, which has a carboxyl group (rather than the carboxyamide group of azide 15), provides a low yield of amide 31 at each pH (FIG. 2). Again, these data are consistent with protonation of the iminophosphorane nitrogen being undesirable. We note that others have reported that couplings of azide 30 as well as 14 similar azido acids mediated by (diphenylphosphino)methanethiol proceed in "quantative yield." (Kim, H.; Cho, J. K.;

Aimoto, S.; Lee, Y.-S. *Org. Lett.* 2006, 8, 1149-1151). These results could not be reproduced in our laboratory.

Additionally, it was determined that the water-soluble phosphinothiol could be integrated with expressed protein ligation. This ability would highlight an intrinsic advantage of using a phosphinothiol (Lundquist, J. T.; Pelletier, J. C. *Org. Lett.* 2001, 3, 781-783) rather than a phosphinoalcohol (Saxon, E.; Bertozzi, C. R. *Science* 2000, 287, 2007-2010) to mediate the Staudinger ligation, as only a phosphinothiol can effect the requisite acyl transfer from a protein-intein thioester. (Nilsson, B. L.; Kiessling, L. L.; Raines, R. T. *Org. Lett.* 2000, 2, 1939-1941.) A model protein, bovine pancreatic ribonuclease (RNase A) was used. This protein has been the object of much seminal work in protein chemistry (Raines, R. T. *Chem. Rev.* 1998, 98, 1045-1066) and has been manipulated previously with expressed protein ligation. (Hondal, R. J.; Nilsson, B. L.; Raines, R. T. *J. Am. Chem. Soc.* 2001, 123, 5140-5141. Arnold, U.; Hinderaker, M. P.; Nilsson, B. L.; Huck, B. R.; Gellman, S. H.; Raines, R. T. *J. Am. Chem. Soc.* 2002, 124, 8522-8523. Arnold, U.; Hinderaker, M. P.; Koditz, J.; Golbik, R.; Ulbrich-Hoffmann, R.; Raines, R. T. *J. Am. Chem. Soc.* 2003, 125, 7500-7501; Muir, T. W. *Annu. Rev. Biochem.* 2003, 72, 249-289; Evans, T. C. et al. *Protein Science* 1998, 7, 2256-2264; Kalia, J.; Raines, R. T. *Chem Bio Chem* 2006, 7, 1375-1383.)

The C-terminal residue of RNase A is valine, which is known to diminish the cleavage efficiency of protein-intein thioesters. (Yee, C. S.; Seyedsayamdost, M. R.; Chang, M. C.; Nocera, D. G.; Stubbe, J. *Biochemistry* 2003, 42, 14541-14552. Lue, R. Y.; Chen, G. Y.; Hu, Y.; Zhu, Q.; Yao, S. Q. *J. Am. Chem. Soc.* 2004, 126, 1055-1062.) To avert this problem, recombinant DNA technology was used to insert a glycine residue between the C terminus of RNase A and the N terminus of the mxe intein. The resulting Met(−1)RNase A-Gly-mxe intein chitin-binding domain fusion protein was produced in *Escherichia coli*, and the cell lysate was loaded onto a chitin resin (Scheme 6), as described previously. (Kalia, J.; Raines, R. T. *ChemBioChem* 2006, 7, 1375-1383.) The chitin resin was then incubated with phosphinothiol 17 (40 mM). The column eluate contained the desired product, phosphinothioester 32, as verified by MALDI-TOF mass spectrometry (m/z 14 225, expected: 14 224). It is noteworthy that phosphinothiol 17 was able to perform the transthioesterification directly, without the need for a catalytic small-molecule thiol. (Raines, R. T. *Chem. Rev.* 1998, 98, 1045-1066.) The lowering of the thiol pKa of phosphinothiol 17 upon protonation of its two dimethylamino groups could enhance its reactivity.

Scheme 6: Route for the integration of the Traceless Staudinger Ligation and Expressed Protein Ligation.

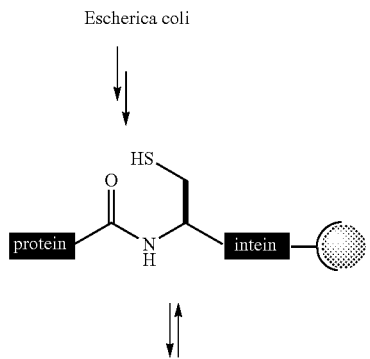

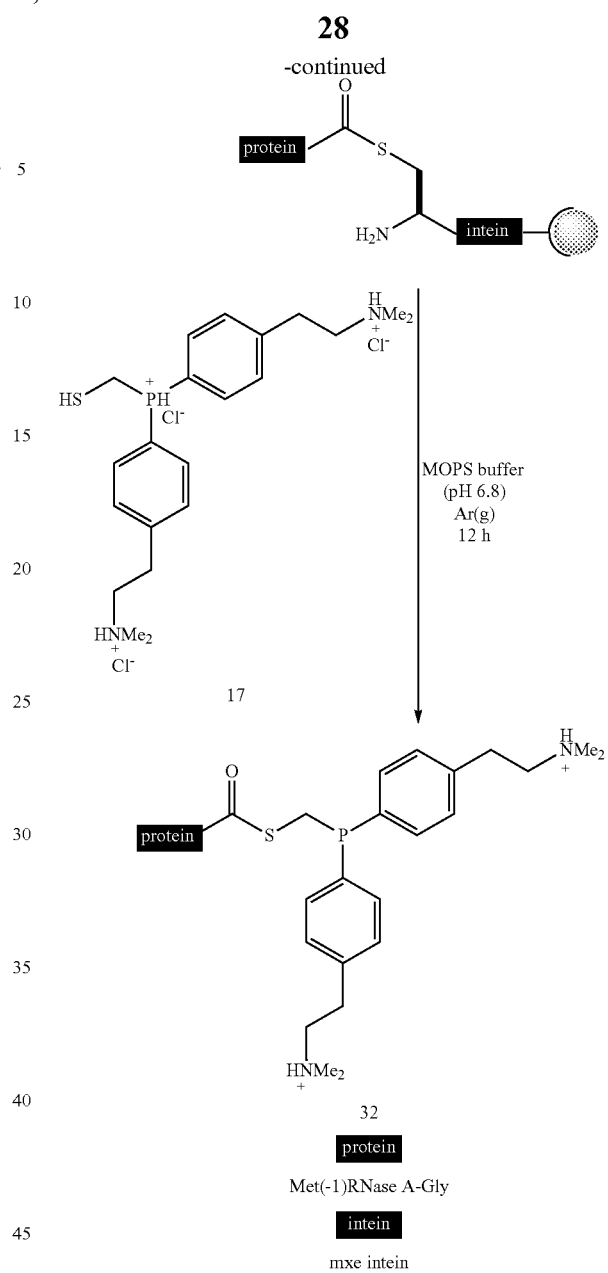

A water-soluble phosphinothiol has been developed that enables efficient traceless Staudinger ligations. The use of dimethylamino groups on the phosphinothiol apparently serves not only to facilitate its water solubility but also to discourage protonation of the nitrogen in the iminophosphorane intermediate, which enables S→N acyl transfer to compete with hydrolysis. As a proof-of-principle for its utility in the integration of Staudinger ligation and expressed protein ligation, the water soluble phosphinothiol and recombinant DNA technology were used to generate a protein with a C-terminal phosphinothioester, which is poised for undergoing Staudinger ligation.

Reagent chemicals were obtained from commercial suppliers, and reagent grade solvents were used without further purification. Procedures were performed at room temperature (~23° C.) unless indicated otherwise. Reactions were monitored by thin-layer chromatography with visualization by ultraviolet light or staining with KMnO4, ninhydrin, PMA, or I₂. Compound purification was carried out with flash chromatography on silica gel, which had a mesh of 230-400 (ASTM) and a pore size of 60 Å. The removal of solvents and other volatile materials "under reduced pressure" refers to the use of a rotary evaporator at water-aspirator pressure (<20 Torr) and a water bath of <40° C.

NMR spectra were acquired at ambient temperature with a Bruker DMX-400 Avance spectrometer ($^1$H, 400 MHz; $^{13}$C, 100.6 MHz; $^{31}$P, 161 MHz) or Bruker Avance DMX-500 spectrometer ($^1$H, 500 MHz; $^{13}$C, 125.7 MHz; $^{31}$P, 202 MHz) at the National Magnetic Resonance Facility at Madison (NMRFAM) or a Varian Inova 500 ($^1$H, 500 MHz; $^{13}$C, 125.7 MHz; $^{31}$P, 202 MHz) spectrometer at the University of Wisconsin Nuclear Magnetic Resonance Facility. Carbon-13 and phosphorus-31 spectra were protondecoupled, and phosphorus-31 spectra were referenced against an external standard of deuterated phosphoric acid (0 ppm). Mass spectrometry was performed with a Micromass LCT (electrospray ionization, ESI) in the Mass Spectrometry Facility in the Department of Chemistry or a Voyager DE-Pro mass spectrometer (matrix-assisted laser desorption-time-of-flight, MALDI-TOF) in the Biophysics Instrumentation Facility.

Phosphine Oxide 5. 4-Iodo-t-butyl benzoate (6.98 g, 22.9 mmol) was dissolved in dry THF (45 mL) and cooled to −20° C. with an isopropanol/dry ice bath. Freshly prepared isopropyl magnesium bromide (1.0 M solution in THF, 25 mL, 25 mmol) was added to this solution dropwise. (Johnson, E. C. B.; Kent, S. B. H. *J. Am. Chem. Soc.* 2006, 128, 6640-6646.) After being stirred for 1.5 h at −20° C., the reaction mixture containing Grignard reagent 4 was added dropwise slowly to a cooled solution of chloromethylphosphonic dichloride (1.57 g, 11.5 mmol) in THF (45 mL) at −20° C. The resulting solution was allowed to warm to room temperature overnight. After the solution was quenched with 2 mL of water, the solvent was removed under reduced pressure. The resulting oil was dissolved in $CH_2Cl_2$, and this solution was washed with brine. The combined organic extracts were dried over anhydrous $MgSO_4$(s) and filtered, and the filtrate was concentrated to yield an orange oil that was purified by flash chromatography (silica gel, 2%/v MeOH in $CH_2Cl_2$) to give phosphine oxide 5 as a white solid in 3% yield. $^1$H MR (CDCl$_3$, 400 MHz) δ 8.15-8.11 (m, 4H), 7.92-7.85 (m, 4H), 4.12 (d, J) 6.7 Hz, 2H), 1.61 (s, 18H) ppm; $^{13}$C NMR CDCl$_3$, 125 MHz) δ 164.71, 136.20, 133.09, 131.71 (d, J) 10.8 Hz), 29.79 (d, J) 13.2 Hz), 82.31, 37.48 (d, J) 74.4 Hz), 28.33 ppm; $^{31}$P NMR (CDCl$_3$, 161 MHz) δ 27.88 ppm; MS (ESI) m/z 473.1273 MNa+[$C_{23}H_{28}ClO_5PNa+$]) 473.1261).

Phosphine Oxide 6. Potassium thioacetate (432 mg, 3.78 mmol) as added to a solution of phosphine oxide 5 (1.42 g, 3.15 mmol) in anhydrous DMF (25 mL) under Ar(g). The reaction mixture was stirred overnight, and the solvent was removed under reduced pressure. The residue was dissolved in ethyl acetate (15 mL), and the resulting solution as washed with water and brine. The combined organic extracts were dried over anhydrous $MgSO_4$(s) and filtered, and the solvent was removed under reduced pressure. The residue was purified by flash chromatography (silica gel, 50% v/v ethyl acetate in hexane) to give phosphine oxide 6 as a light amber solid in 98% yield. $^1$H NMR (CDCl$_3$, 00 MHz) δ 8.09-8.07 (m, 4H), 7.84-7.80 (m, 4H), 3.80 (d, J) 8.3 z, 2H), 2.28 (s, 3H), 1.59 (s, 18H) ppm; 13C NMR (CDCl$_3$, 125 MHz) 193.07, 164.84, 135.88, 134.82, 131.25 (d, J) 9.3 Hz), 129.26 (d,) 11.8 Hz), 82.24, 30.35, 28.37, 27.24 (d, J) 71.3 Hz) ppm; 31 P MR (CDCl$_3$, 161 MHz) δ 28.36 ppm; MS (ESI) m/z 513.1487 (MNa$^+$ $C_{25}H_{31}O_6PSNa^+$]) 513.1477).

Phosphinothioester 7. Phosphine oxide 6 (1.52 g, 3.09 mmol) was dissolved in anhydrous chloroform (25 mL) under Ar(g). Trichlorosilane 4.7 mL, 46.3 mmol) was added to this solution, and the resulting solution was stirred under Ar(g) for 72 h. The solvent was removed under reduced pressure. (Caution! Excess trichlorosilane in the removed solvent was quenched by the slow addition of saturated sodium bicarbonate in a well-ventilated hood.) The residue was purified by lash chromatography (silica gel, 50% v/v ethyl acetate in hexanes) to give phosphinothioester 7 as a pale yellow oil in 38% yield. $^1$H NMR CDCl$_3$, 400 MHz) δ 7.97-7.95 (m, 4H), 7.46-7.43 (m, 4H), 3.53 (d,) 3.6 Hz, 2H), 2.30 (s, 3H), 1.59 (s, 18H) ppm; $^{13}$C NMR (CDCl$_3$, 25 MHz) δ 194.12, 165.21, 141.78 (d, J) 17.8 Hz), 132.77, 132.72 d, J) 18.7 Hz), 129.42 (d, J) 5.6 Hz), 81.77, 30.32, 25.30 (d, J) 24.7 Hz), 20.12 ppm; $^{31}$P NMR (CDCl$_3$, 161 MHz) δ14.19 ppm; MS (ESI) m/z 497.1508 (MNa+[$C_{25}H_{34}BO_5PSNa+$]) 97.1528).

Phosphinothioester 8. Phosphinothioester 7 (100 mg, 0.21 mmol) as dissolved in 1:3 trifluoroacetic acid/dichloromethane (2.5 mL) under Ar(g), and the resulting solution was stirred for 4 h or until the reaction was judged to be complete by TLC. The solvent was removed under reduced pressure as an azeotrope with toluene to give phosphinothioester 8 as an off-white solid in quantitative yield. $^1$H NMR (DMSO-d6, 400 MHz) δ 7.94-7.92 (m, 4H), 7.56-7.52 (m, 4H), 3.67 (d, J) 3.1 Hz, 2H), 2.30 (s, 3H) ppm; $^{13}$C NMR (DMSO-d6, 125 MHz) δ193.66, 166.48, 141.54 (d, J) 17.6 Hz), 132.26 (d, J) 18.6 Hz), 130.95, 128.84 (d, J) 7.0 Hz), 29.92, 23.49 (d, J) 21.4 Hz) ppm; $^{31}$P NMR (DMSO-d6, 161 MHz) δ −13.52 ppm; MS (ESI) m/z 361.0293 (MH−[$C_{17}H_{15}O_5PSH−$]) 361.0300).

Phosphinothiol 3. Phosphinothioester 8 (100 mg, 0.21 mmol) was dissolved in degassed MeOH (1 mL), and degassed 2 N NaOH (1.5 mL) was added to this solution under Ar(g). The resulting solution was stirred for 1.5 h. The solvent was removed under reduced pressure, and the residue was acidified with 4 N HCl and extracted into EtOAc (3-5 mL). The combined organic extracts were dried over anhydrous MgSO4(s) and filtered, and the solvent was removed under reduced pressure to give phosphinothiol 3 as a pale yellow oil in 76% yield. $^1$H NMR (DMSO-d6, 400 MHz) δ 7.93-7.90 (m, 4H), 7.56-7.52 (m, 4H), 3.30 (d, J) 5.7 Hz, 2H) ppm; $^{13}$C NMR (DMSO-d6, 125 MHz) δ 166.97, 142.53 (d, J) 17.5 Hz), 132.74 (d, J) 18.0 Hz), 131.26, 129.25 (d, J) 5.1 Hz), 18.55 (d, J) 13.1 Hz) ppm; $^{31}$P NMR (DMSO-d6, 161 MHz) δ −8.48 ppm; MS (ESI) m/z 319.0181 (MH−[C15H13O4PSH−]) 319.0194).

Phosphine Oxide 10. Phosphine oxide 5 (2.0 g, 4.44 mmol) was dissolved in $CH_2Cl_2$ (35 mL), and TFA (8.75 mL) was added to this solution. The resulting solution was stirred for 4 h. The solvent was removed under reduced pressure to give phosphine oxide 10 as an off-white solid in quantitative yield. $^1$H NMR (CD$_3$OD, 400 MHz) δ 8.22-8.20=(m, 4H), 8.00-7.95 (m, 4H), 4.53 (d, J) 5.3 Hz, 2H) ppm; $^{13}$C NMR (CD$_3$OD, 125 MHz) δ 168.48, 136.35, 135.38, 132.77 (d, J) 8.4 Hz), 131.18 (d, J) 12.9 Hz), 38.19 (d, J) 73.8 Hz) ppm; $^{31}$P NMR (CD$_3$OD, 161 MHz) δ 31.60 ppm; MS (ESI) m/z 337.0020 (MNa+[$C_{25}H_{34}BO_5PSNa+$]) 337.0033).

Phosphine Oxide 11. Phosphine oxide 10 (2.54 g, 7.5 mmol) was dissolved in anhydrous $CH_2Cl_2$ (65 mL) and anhydrous DMF (5 mL) under Ar(g). Thionyl chloride (3.28 mL, 45 mmol) was added dropwise to this solution, and the resulting solution was stirred for 3 h. The solvent and all traces of excess thionyl chloride were removed under reduced pressure. In a separate flask, glycine t-butyl ester-HCl (4.88 g, 29.1 mmol) was dissolved in anhydrous $CH_2Cl_2$ (65 mL), and N,N diisoprolylethylamine (DIEA, 10.0 mL, 58.2 mmol) was added to this solution. The resulting solution was cooled to 0° C. with an ice bath. The incipient acid chloride was added dropwise slowly and with stirring, and the reaction mixture was allowed to warm to room temperature and stirred for 4 h. The reaction mixture was washed with 1 N HCl (35 mL) and brine, dried over anhydrous $MgSO_4(s)$, and filtered. The solvent was removed under reduced pressure, and the residue was purified by flash chromatography (silica gel, 4% v/v MeOH in $CH_2Cl_2$) to give phosphine oxide 11 as a white solid in 66% yield. $^1H$ NMR ($CDCl_3$, 400 MHz) δ 9.05-9.02 (m, 2H), 8.01-7.95 (m, 8H), 4.72 (d, J) 5.3 Hz, 2H), 3.91 (d, J) 6.1 Hz, 4H), 1.42 (s, 18H) ppm; $^{13}C$ NMR ($CDCl_3$, 125 MHz) δ 169.23, 166.42, 138.31, 132.99, 131.99, 127.80, 82.84, 42.72, 37.39 (d, J) 75.1 Hz), 28.25 ppm; $^{31}P$ NMR ($CDCl_3$, 161 MHz) ä 27.94 ppm; MS (ESI) m/z 587.1675 (MNa+[$C_{27}H_{34}ClN_2O_7PNa+$]) 587.1690).

Phosphine Oxide 12. Potassium thioacetate (677 mg, 5.93 mmol) was added to a solution of phosphine oxide 11 (2.79 g, 4.94 mmol) in anhydrous DMF (45 mL) under Ar(g). The resulting solution was stirred overnight, after which the solvent was removed under reduced pressure. The residue was dissolved in ethyl acetate (25 mL), and the resulting solution was washed with water and brine. The combined organic extracts were dried over anhydrous $MgSO_4(s)$ and filtered, and the solvent was removed under reduced pressure. The residue was purified by flash chromatography (silica gel, 5% v/v MeOH in $CH_2Cl_2$) to give phosphine oxide 12 as a yellow oil in 85% yield. $^1H$ NMR ($CDCl_3$, 400 MHz) δ 7.90-7.79 (m, 4H), 7.71-7.65 (m, 4H), 4.12 (d, J) 5.0 Hz, 4H), 3.75 (d, J) 8.1 Hz, 2H), 2.25 (s, 3H), 1.41 (s, 18H) ppm; $^{13}C$ NMR ($CDCl_3$, 125 MHz) δ 192.69, 169.19, 166.58, 137.90, 134.30, 30.76, 127.68, 82.51, 42.61, 30.16, 28.16, 26.84 ppm; $^{31}P$ NMR ($CDCl_3$, 161 MHz) δ 29.04 ppm; MS (ESI) m/z 627.1923 (MNa+[$C_{29}H_{37}N_2O_8PSNa+$]) 627.1906).

Phosphinothioester 13. Phosphine oxide 12 (2.54 g, 4.2 mmol) was dissolved in anhydrous chloroform (38 mL) under Ar(g). Trichlorosilane (6.35 mL, 62.9 mmol) was added to this solution, and the resulting solution was stirred under Ar(g) for 72 h. The solvent was removed under reduced pressure. (Caution! Excess trichlorosilane in the removed solvent was quenched by the slow addition of saturated sodium bicarbonate in a well-ventilated hood.) The residue was purified by flash chromatography (silica gel, 2% v/v MeOH in $CH_2Cl_2$) to give phosphinothioester 13 as a white solid in 52% yield. $^1H$ NMR ($CDCl_3$, 400 MHz) δ 7.80-7.78 (m, 4H), 7.48-7.44 (m, 4H), 6.73 (bs, 2H), 4.13 (d, J) 5.0 Hz, 4H), 3.53 (d, J) 4.3 Hz, 2H), 2.30 (s, 3H), 1.50 (s, 18H) ppm; $^{13}C$ NMR ($CDCl_3$, 125 MHz) δ 194.39, 169.29, 166.84, 140.94 (d, J) 17.4 Hz), 134.84, 133.10 (d, J) 20.3 Hz), 127.30 (d, J) 6.2 Hz), 82.84, 42.69, 30.50, 20.25, 25.45 (d, J) 24.4 Hz) ppm; $^{31}P$ NMR ($CDCl_3$, 161 MHz) δ -14.42 ppm; MS (ESI) m/z 611.1937 (MNa+[$C_{29}H_{37}N_2O_7PSNa+$]) 611.1957).

Phosphinothioester 14. Phosphinothioester 13 (100 mg, 0.17 mmol) was dissolved in 25% v/v trifluoroacetic acid in dichloromethane (2 mL) under Ar(g), and the resulting solution was stirred for 4 h. The solvent was removed under reduced pressure as an azeotrope with toluene to give di-acid 14 as an off-white solid in quantitative yield. $^1H$ NMR (DMSO-d6, 400 MHz) δ 8.92-8.88 (m, 2H), 7.87-7.85 (m, 4H), 7.55-7.51 (m, 4H), 3.91 (d, J) 5.4 Hz, 4H), 3.66 (d, J) 12.7 Hz, 2H), 2.30 (s, 3H) ppm; $^{13}C$ NMR (DMSO-d6, 125 MHz) δ 194.02, 171.26, 166.05, 140.34 (d, J) 17.2 Hz), 134.51, 132.56 (d, J) 19.3 Hz), 127.39 (d, J) 4.8 Hz), 41.25, 30.26, 24.01 (d, J) 23 Hz) ppm; $^{31}P$ NMR (DMSO-d6, 161 MHz) δ -14.55 ppm.

Phosphinothiol 9. Phosphinothioester 14 (100 mg, 0.21 mmol) was dissolved in degassed MeOH (1 mL), and degassed 2 N NaOH (1.5 mL) was added to this solution under Ar(g). The resulting solution was stirred for 1.5 h. The solvent was removed under reduced pressure, and the residue was acidified with 4 N HCl and extracted into EtOAc (3-5 mL). The combined organic extracts were dried over anhydrous $MgSO_4(s)$ and filtered, and the solvent was removed under reduced pressure to give phosphinothiol 9 as an off-white solid quantitative yield. $^1H$ NMR (DMSO-d6, 400 MHz) δ 8.98 (bs, 2H), 7.97-7.85 (m, 4H), 7.59-7.46 (m, 4H), 3.91 (d, J) 5.6 Hz, 4H), 3.50 (bs, 2H) ppm $^{13}C$ NMR (DMSO-d6, 125 MHz) δ 171.19, 166.05, 134.33, 132.47, 131.09, 127.43, 41.27, 18.78 (d, J) 21.5 Hz) ppm; $^{31}P$ NMR (DMSO-d6, 161 MHz) δ -14.47 ppm.

[$2-^{13}C$]-2-Azido-acetamide (15). [$2-^{13}C$]-2-Azido-acetic acid was synthesized from [$^{13}C^\alpha$]glycine by a procedure described previously. (Dohle, W.; Lindsay, D. M.; Knochel, P. Org. Lett. 2001, 3, 2871-2873) [$2-^{13}C$]-2-Azido-acetic acid (300 mg, 2.94 mmol) was dissolved in $CH_2Cl_2$ (10 mL). 1,1'-Carbonyldiimidazole (477 mg, 2.94 mmol) was added to this solution, and the resulting mixture was stirred for 20 min. Ammonia (25 mL, 0.5 M in dioxane, 14.7 mmol) was then added, and the resulting solution was stirred for 2 h. The solvent was removed under reduced pressure, and the amber residue was purified by flash chromatography (silica gel, 10% v/v MeOH in $CH_2Cl_2$) to give [$2-^{13}C$]-2-azido-acetamide (15) as a white solid in 76% yield. $^1H$ NMR ($CDCl_3$, 400 MHz) δ 6.20 (bs, 1H), 5.40 (bs, 1H), 4.00 (d, J) 143.7 Hz, 2H) ppm; $^{13}C$ NMR ($CDCl_3$, 125 MHz) δ 170.13, 52.55 ppm; MS (ESI) m/z 101.0417 (MH+[$C_2H_4N_4OH+$]) 101.0419). Ac[$^{13}C^\alpha$]GlyNH$_2$ (16). AcSCH$_2$PPh$_2$ (ref 17; 258 mg, 0.62 mmol) and azide 15 (63 mg, 0.62 mmol) were dissolved in THF (6.5 mL). This solution was allowed to stir for 12 h. The white precipitate that formed was isolated by filtration and was judged to be identical to commercial AcGlyNH$_2$ by NMR spectroscopy.

Mesylate 18. Triethylamine (5.2 mL, 37.3 mmol) was added to a solution of 4-bromophenethyl alcohol (5.0 g, 24.9 mmol) in $CH_2Cl_2$ (200 mL), and the resulting solution was cooled to 0° C. with an ice bath. Methanesulfonyl chloride (2.7 mL, 34.8 mmol) was added dropwise to the reaction mixture, and the resulting solution was allowed to warm slowly to room temperature overnight. The solution was washed with 0.1 N HCl and brine, and the combined organic extracts were dried over anhydrous $MgSO_4(s)$ and filtered, and the solvent was removed under reduced pressure. The crude yellow solid was purified by flash chromatography (silica gel, 70% v/v hexanes in $CH_2Cl_2$) to give mesylate 18 as a white solid in 98% yield. $^1H$ NMR ($CDCl_3$, 400 MHz) δ 7.46 (d, J) 8.5 Hz, 2H), 7.12 (d, J) 8.6 Hz, 2H), 4.39 (t, J) 6.9 Hz, 2H), 3.02 (t, J) 6.7 Hz, 2H), 2.89 (s, 3H) ppm; $^{13}C$ NMR ($CDCl_3$, 125 MHz) δ 135.55, 132.52, 130.92, 121.70, 69.83, 37.68, 35.31 ppm.

Dimethylamine 19. Mesylate 18 (6.82 g, 24.4 mmol) was dissolved in anhydrous THF (150 mL) under Ar(g), and dimethylamine (2 M in THF, 50 mL, 100 mmol) was added to this solution. The resulting solution was heated at 45° C. for 16 h. The white solid that formed was removed by filtration, and the solvent was removed under reduced pressure. The residue was purified by flash chromatography (silica gel, 10% v/v MeOH in $CH_2Cl_2$) to give dimethylamine 19 as a pale yellow oil in 66% yield. $^1H$ NMR ($CDCl_3$, 400 MHz) δ 7.40 (d, J) 8.4 Hz, 2H), 7.08 (d, J) 8.0 Hz, 2H), 2.75 (t, J) 7.9 Hz, 2H), 2.53 (t, J) 7.9 Hz, 2H), 2.31 (s, 6H) ppm; $^{13}C$ NMR ($CD_3OD$, 125 MHz) δ 139.35, 132.87, 131.85, 121.40, 61.34, 44.94, 33.23 ppm; MS (ESI) m/z 228.0387 (MNa+[$C_{10}H_{14}BrNNa+$]) 228.0388).

Phosphine Oxide 20. Dimethylamine 19 (7.66 g, 33.6 mmol) was dissolved in anhydrous THF (72 mL) under Ar(g) in a flame-dried round-bottom flask equipped with a reflux condenser. To facilitate generation of the Grignard reagent, a catalytic amount of 12 was added to the solution. Crushed magnesium turnings (971 mg, 40.3 mmol) were then added to this solution, and the resulting solution was heated at reflux for 2 h to generate the Grignard reagent. In a separate flamed-dried flask, diethyl phosphite (1.3 mL, 10.1 mmol) was dissolved in anhydrous THF (30 mL) and cooled to 0° C. with an ice bath. The solution of Grignard reagent was added dropwise to this solution, and the resulting solution was allowed to warm to room temperature and stirred overnight. The reaction mixture was then quenched with water (2 mL), and the solvent was removed under reduced pressure. The residue was dissolved in $CH_2Cl_2$, and the resulting solution was washed with water and brine. The combined organic extracts were dried over anhydrous $MgSO_4(s)$ and filtered, and the solvent was removed under reduced pressure. The residue was purified by flash chromatography (silica gel, 20% v/v MeOH in $CH_2Cl_2$) to give phosphine oxide 20 as a colorless oil in 75% yield. $^1$H NMR (CDCl$_3$, 400 MHz) δ 8.03 (d, J) 1.2 ppm, 1H), 7.64-7.59 (m, 4H), 7.35-7.33 (m, 4H), 2.83 (t, J) 7.5 Hz, 4H), 2.54 (t, J) 8.2 Hz, 4H), 2.29 (s, 12H) ppm; $^{13}$C NMR (CDCl$_3$, 125 MHz) δ 145.72, 131.08 (d, J) 11.5 Hz), 129.41 (J) 12.4 Hz), 128.71, 61.11, 45.64, 34.56 ppm; $^{31}$P NMR (CDCl$_3$, 161 MHz) δ 21.75 ppm; MS (ESI) m/z 345.2090 (MNa+ [$C_{20}H_{29}N_2OPNa+$]) 345.2096).

Phosphine-Borane Complex 21. A solution of phosphine oxide 20 (3.18 g, 9.24 mmol) in anhydrous $CH_2Cl_2$ (25 mL) was added dropwise slowly to a solution of DIBAL (1 M in $CH_2Cl_2$, 46.2 mL, 46 mmol) under Ar(g) in a flame-dried three-neck round-bottom flask. The resulting solution was stirred for 20 min, and then cooled to 0° C. with an ice bath. The solution was then diluted with $CH_2Cl_2$ (20 mL), and a sparge needle of Ar(g) was allowed to blow through the solution for 5 min. A solution of 2 N NaOH (20 mL) was added dropwise slowly to the reaction mixture (Caution! Gas evolution!) followed by a saturated solution of Rochelle's salt (20 mL) to dissipate the emulsion that forms. The resulting biphasic solution was transferred to a separatory funnel, and the organic layer was separated, dried over anhydrous $MgSO_4(s)$, filtered, and concentrated under reduced pressure to 75 mL. The resulting solution was cooled to 0° C. with an ice bath under Ar(g), and borane.dimethyl sulfide complex (10 M, 2.96 mL, 29.6 mmol) was added dropwise. The resulting reaction mixture was allowed to warm slowly to room temperature overnight. The solvent was removed under reduced pressure, and the crude oil was purified by flash chromatography (silica gel, $CH_2Cl_2$) to give phosphine-borane complex 21 as a white solid in 82% yield. $^1$H NMR (CDCl$_3$, 400 MHz) δ 7.62-7.57 (m, 4H), 7.31-7.29 (m, 4H), 6.30 (d, J) 378.8 Hz, 1H), 3.13-3.09 (m, 4H), 2.95-2.91 (m, 4H), 2.67 (s, 12H), 2.30-0.70 (m, 9H) ppm; $^{13}$C NMR (CDCl$_3$, 125 MHz) δ 142.42, 133.54 (d, J) 10.7 Hz), 129.79 (d, J) 10.0 Hz), 124.66 (d, J) 58.7 Hz), 65.83, 52.12, 31.53 ppm; $^{31}$P NMR (CDCl$_3$, 161 MHz) δ 0.00 ppm; MS (ESI) m/z 343.2474 (MH+−2BH$_3$[$C_{20}H_{32}BN_2PH+$]) 343.2474).

Phosphine-Borane Complex 22. Phosphine-borane complex 21 (2.32 g, 6.27 mmol) was dissolved in 1:1 THF/$CH_2Cl_2$ (60 mL). Formaldehyde (37% v/v in $H_2O$; 3.83 mL) was added to this solution, followed by potassium hydroxide (358 mg, 6.39 mmol). The resulting biphasic solution was stirred overnight at room temperature, after which the organic solvent was removed under reduced pressure. The residue was dissolved in ethyl acetate (30 mL), and the organic layer was dried over anhydrous $MgSO_4(s)$, filtered, and concentrated under reduced pressure. The residue was purified by flash chromatography (silica gel, 5% v/v ethyl acetate in $CH_2Cl_2$) to give phosphine-borane complex 22 as a white solid in 80% yield. $^1$H NMR (CDCl$_3$, 400 MHz) δ 7.69-7.64 (m, 4H), 7.34-7.32 (m, 4H), 4.42 (d, J) 6.5 Hz, 2H), 3.15-3.11 (m, 4H), 2.97-2.93 (m, 4H), 2.67 (s, 12H), 2.20-0.50 (m, 9H) ppm; $^{13}$C NMR (CDCl$_3$, 125 MHz) δ 142.46, 133.38 (d, J) 8.7 Hz), 129.72 (d, J) 10.6 Hz), 125.16 (d, J) 56.1 Hz), 65.90, 60.60 (d, J) 42.1 Hz), 52.18, 31.11 ppm; $^{31}$P NMR (CDCl$_3$, 161 MHz) δ 16.92 ppm; MS (ESI) m/z 423.3047 (MNa+ [$C_{21}H_4OB_3N_2OPNa+$]) 423.3055).

Phosphine-Borane Complex 23. Triethylamine (650 μL, 4.67 mmol) was added to a solution of phosphine-borane complex 22 (1.25 g, 3.11 mmol) in $CH_2Cl_2$ (30 mL), and this solution was cooled to 0° C. with an ice bath. Methanesulfonyl chloride (337 μL, 4.36 mmol) was added dropwise, and the resulting solution was allowed to warm slowly to room temperature overnight. The solution was washed with 0.1 N HCl and brine, and the combined organic extracts were dried over anhydrous $MgSO_4(s)$, filtered, and concentrated under reduced pressure. The residue was purified by flash chromatography (silica gel, 2% v/v ethyl acetate in $CH_2Cl_2$) to give phosphine-borane complex 23 as a white solid in 95% yield. $^1$H NMR (CDCl$_3$, 400 MHz) δ 7.69-7.64 (m, 4H), 7.37-7.27 (m, 4H), 4.87 (d, J) 2.0 Hz, 2H), 3.17-3.13 (m, 4H), 2.98-2.94 (m, 4H), 2.95 (s, 3H), 2.67 (s, 12H), 2.20-0.50 (m, 9H) ppm; $^{13}$C NMR (CDCl$_3$, 125 MHz) δ 143.20, 133.51 (d, J) 10.4 Hz), 129.88 (d, J) 10.8 Hz), 123.51 (d, J) 57.8 Hz), 65.76, 64.58 (d, J) 37.4 Hz), 52.19, 37.71, 31.11 ppm; $^{31}$P NMR (CDCl$_3$, 161 MHz) δ 17.82 ppm; MS (ESI) m/z 501.2811 (MNa+[$C_{22}H_{42}B_3N_2O_3$—PSNa+]) 501.2831).

Phosphine-Borane Complex 24. Potassium thioacetate (404 mg, 3.54 mmol) was added to a solution of phosphine-borane complex 23 (41 g, 2.95 mmol) in anhydrous DMF (29 mL) under Ar(g). The resulting solution was stirred overnight at room temperature, after which the solvent was removed under reduced pressure. The residue was dissolved in ethyl acetate (20 mL), and the resulting solution was washed with water and brine. The combined organic extracts were dried over anhydrous $MgSO_4(s)$, filtered, and concentrated under reduced pressure. The residue was purified by flash chromatography (silica gel, 2% v/v ethyl acetate and 28% hexanes in $CH_2Cl_2$) to give phosphine-borane complex 24 as a white solid in 60% yield. $^1$H NMR (CDCl$_3$, 400 MHz) δ 7.65-7.60 (m, 4H), 7.33-7.30 (m, 4H), 3.68 (d, J) 7.0 Hz, 2H), 3.14-3.10 (m, 4H), 2.97-2.93 (m, 4H), 2.67 (s, 12H), 2.27 (s, 3H), 2.20-0.60 (m, 9H) ppm; $^{13}$C NMR (CDCl$_3$, 125 MHz) δ 193.32, 142.50, 133.00 (d, J) 10.5 Hz), 129.55 (d, J) 12.3 Hz), 126.03 (d, J) 56.2 Hz), 65.75, 54.09, 30.98, 30.27, 23.88 (d, J) 35.6 Hz) ppm; $^{31}$P NMR (CDCl$_3$, 161 MHz) δ 18.69 ppm; MS (ESI) m/z 481.2929 (MNa+[$C_{23}H_{42}B_3N_2OPSNa+$]) 481.2932).

Phosphinothioester 25. Phosphine-borane complex 24 (250 mg, 0.55 mmol) was dissolved in toluene (5 mL) under Ar(g). DABCO (190 mg, 1.69 mmol) was added, and the resulting solution was heated to 40° C. for 4 h. The solvent was removed under reduced pressure, and the residue was purified by flash chromatography (silica gel, 20% v/v MeOH in $CH_2Cl_2$) to give phosphinothioester 25 as a colorless oil in 86% yield. $^1$H NMR (CDCl$_3$, 400 MHz) δ 7.36-7.33 (m, 4H), 7.20-7.18 (m, 4H), 3.47 (d, J) 3.5 Hz, 2H), 2.79-2.75 (m, 4H), 2.55-2.51 (m, 4H), 2.29 (s, 15H) ppm; $^{13}$C NMR (CDCl$_3$, 125 MHz) δ 194.89, 141.76, 134.25 (d, J) 12.9 Hz), 132.95 (d, J) 19.5 Hz), 129.03 (d, J) 6.1 Hz), 61.36, 45.61, 34.29, 30.46, 26.13 (d, J) 21.1 Hz) ppm; $^{31}$P NMR (CDCl$_3$, 161 MHz) δ −16.84 ppm; MS (ESI) m/z 417.2135 (MH+ [$C_{23}H_{33}N_2OPSH+$]) 417.2129).

Phosphinothiol 17. Phosphinothioester 25 (323 mg, 0.78 mmol) was dissolved in degassed MeOH (8 mL), and NaOH (31 mg) was added to this solution under Ar(g). The resulting solution was stirred at room temperature for 1.5 h. The solvent was removed under reduced pressure, and the residue was acidified with 4 N HCl in dioxane and filtered to give phosphinothiol 17 as a white solid in quantitative yield. $^1$H NMR (DMSO-d6, 400 MHz) δ 11.05 (bs, 1H), 7.40 (t, J) 7.3 Hz, 4H), 7.30 (t, J) 8.2 Hz, 4H), 4.25 (bs, 2H), 3.26-3.22 (m, 4H), 3.20-3.18 (m, 2H), 3.05-3.01 (m, 4H), 2.77 (s, 12H), 1.20 (t, J) 7.0 Hz, 1H) ppm; $^{13}$C NMR (DMSO-d6, 125 MHz) δ 138.12, 135.50, 132.93, 128.97, 56.83, 41.87, 45.22, 29.47 ppm; $^{31}$P NMR (DMSO-d6, 161 MHz) δ −10.60 ppm; MS (ESI) m/z 375.2039 (MH+[$C_{21}H_{31}N_2PSH+$]) 375.2024).

Phosphinothioester 26. N-Acetyl glycine (95.3 mg, 0.81 mmol) was dissolved in anhydrous DMF (6 mL) under Ar(g). Hydroxybenzotriazole (105 mg, 0.78 mmol) was then added to the solution, followed by N,N'-diisopropyl-carbodiimide (DIC, 121 μL, 0.78 mmol). After the reaction mixture was allowed to stir for 20 min, a solution of phosphinothiol 17 (293 mg, 0.78 mmol) was added, followed by DIEA (564 μL, 3.24 mmol). The resulting solution was stirred for 4 h at room temperature under Ar(g). The solvent was removed under reduced pressure, and the resulting crude oil was purified by flash chromatography (silica gel, 20% v/v MeOH in $CH_2Cl_2$) to give phosphinothioester 26 as a colorless oil in 75% yield. $^1$H NMR (CDCl$_3$, 400 Hz) δ 7.35-7.31 (m, 4H), 7.20-7.18 (m, 4H), 6.04 (s, 1H), 4.16 (d, J) 5.4 Hz, 2H), 3.49 (d, J) 3.9 Hz, 2H), 2.81-2.77 (m, 4H), 2.59-2.55 (m, 4H), 2.32 (s, 12H), 2.03 (s, 3H) ppm; $^{13}$C NMR (CDCl$_3$, 125 MHz) δ 196.45, 170.38, 141.79, 133.99, 132.99, 129.11, 61.29, 49.25, 45.58, 34.18, 25.60, 23.14 ppm; $^{31}$P NMR (CDCl$_3$, 161 MHz) δ −16.04 ppm; MS (ESI) m/z 474.2335 (MH+[$C_{25}H_{36}N_3O_2PSH+$]) 474.2344).

AcGly[$^{13}$Cr]GlyNH$_2$ (27). AcGlySCH2PPh2 (Soellner M. B. et al. (2003) J. Am. Chem. Soc. 125:11790-11791; 207 mg, 0.62 mmol) and [2-$^{13}$C]-2-azido-acetamide (15) (63 mg, 0.62 mmol) were dissolved in THF (6.5 mL). The resulting solution was allowed to stir for 12 h. The white precipitate that formed was isolated by filtration to give AcGly[$^{13}$C$^α$]GlyNH2 (27) as a white solid in 61% yield. $^1$H NMR (DMSO-d6, 400 MHz) δ 8.17 (bs, 1H), 8.07 (bs, 1H), 7.21 (bs, 1H), 7.08 (bs, 1H), 3.67 (d, J) 5.7 Hz, 2H), 3.61 (dd, J) 138.6 Hz, 5.9 Hz, 1H), 1.85 (s, 3H) ppm; $^{13}$C NMR (DMSO-d6, 125 MHz) δ 171.19, 170.68, 169.90, 169.29, 50.52, 41.83, 22.50 ppm; MS (ESI) m/z 197.0728 (MNa+ [$C_6H_{11}N_3O_3Na+$]) 197.0732).

Phosphinothioester 28. N-Acetyl alanine (20.6 mg, 0.16 mmol) was dissolved in anhydrous DMF (2 mL) under Ar(g). Hydroxybenzotriazole (20.3 mg, 0.15 mmol) was then added to the solution, followed by N,N'-diisopropyl-carbodiimide (DIC, 23.5 μL, 0.15 mmol). After the reaction mixture was allowed to stir for 20 min, a solution of phosphinothiol 17 (62.4 mg, 0.15 mmol) was added, followed by DIEA (104 μL, 0.6 mmol). The resulting solution was stirred for 4 h at room temperature under Ar(g). The solvent was removed under reduced pressure, and the resulting crude oil was purified by flash chromatography (silica gel, 20% v/v MeOH in $CH_2Cl_2$) to give phosphinothioester 28 as a colorless oil in 78% yield. $^1$H NMR (CDCl$_3$, 400 Hz) δ 7.33 (t, J) 7.6 Hz, 4H), 7.19 (t, J) 7.5 Hz, 4H), 6.10 (d, J) 7.6 Hz, 1H), 4.66 (q, J) 7.6 Hz, 1H), 3.47-3.44 (m, 2H), 2.81-2.77 (m, 4H), 2.57-2.53 (m, 4H), 2.31 (s, 12H), 1.99 (s, 3H), 1.29 (d, J) 7.1 Hz, 3H) ppm; $^{13}$C NMR (CDCl$_3$, 125 MHz) δ 200.05, 169.74, 141.68, 134.26, 133.03 (d, J) 18.4 Hz), 129.11, 61.25, 55.04, 45.51, 34.11, 25.74 (d, J) 23.6 Hz), 23.29, 19.04 ppm; $^{31}$P NMR (CDCl$_3$, 161 MHz) δ −15.93 ppm.

AcAlaGlyNH$_2$ (Unlabeled 29). N-Acetyl-alanyl-pentafluorophenol ester (100 mg, 0.34 mmol) and glycinamide-HCl salt (37 mg, 0.34 mmol) were dissolved in anhydrous THF (3 mL). DIEA (146 μL, 0.84 mmol) was added to this solution, and the resulting solution was allowed to stir for 12 h. The solution was filtered to give AcAlaGlyNH$_2$ (unlabeled 29) as a white solid in 50% yield. AcAla[$^{13}$C$^α$]GlyNH$_2$ (29) was prepared in a similar manner. $^1$H NMR (DMSO-d6, 400 MHz) δ 8.16-8.13 (m, 1H), 7.16 (bs, 1H), 7.08 (bs, 1H), 4.17-4.14 (q, J) 6.1 Hz, 1H), 3.64-3.52 (m, 2H), 1.84 (s, 3H), 1.19 (d, J) 7.0 Hz, 3H) ppm; $^{13}$C NMR (DMSO-d6, 125 MHz) δ 172.65, 171.03, 169.60, 48.71, 41.95, 22.49, 17.65 ppm.

Staudinger Ligations of 14+15, 25+15, 26+15, 28+15, and 30+25. The respective phosphinothioester (0.1 mmol) and azide (10.7 mg, 0.1 mmol) were dissolved in 0.40 M sodium phosphate buffers (0.6 mL) of various pH. The resulting reaction mixtures were stirred for 16 h, and the reaction was monitored with the previously described $^{13}$C NMR assay. (Soellner, M. B.; Tam, A.; Raines, R. T. J. Org. Chem. 2006, 71, 9824-9830.)

Production of Met(−1)RNase A-Gly-mxe Intein-Chitin-Binding Domain. Plasmid pJK01, which directs the expression of the Met(−1)RNase A-Gly-mxe intein-chitin-binding domain fusion protein, 34 was transformed into E. coli BL21 (DE3) cells. Luria-Bertani (LB) medium (5 mL) containing ampicillin (0.10 mg/mL) was inoculated with a single colony, and the resulting culture was grown for 16 h at 37° C. Cells were collected by centrifugation at 2000 g for 2 min and resuspended in LB medium (4 mL). Four 4 L flasks, each containing 1 L of LB medium with ampicillin (0.10 mg/mL), were each inoculated with 1 mL of the resuspended cells. The resulting cultures were grown with shaking at 37° C. until OD=0.5 at 600 nm. Gene expression was then induced by the addition of isopropyl β-Dthiogalactopyranoside (IPTG, to 0.5 mM), and the cultures were grown for an additional 3-4 h at 25° C. Cells were collected by centrifugation and stored at −20° C.

Loading of Fusion Protein onto Chitin. Frozen cells (0.25 g from 0.1 L of E. coli culture) were thawed and suspended in lysis and column buffer (LCB, 5 mL), which was 20 mM 3-(N-morpholino)propanesulfonic acid (MOPS)-NaOH buffer (pH 6.8) containing NaCl (0.5 M), ethylenediaminetetraacetic acid (EDTA; 0.1 mM), and Triton X-100 (0.1% w/w). Cells were lysed by sonication, and the cell lysate was clarified by centrifugation at 15 OOOg for 30 min. Chitin resin (New England Biolabs, Ipswich, Mass.; 1-mL bed volume) was loaded into a column, and equilibrated with degassed LCB (5 mL). The clarified cell lysate was applied slowly to the column of chitin resin. The loaded resin was washed thoroughly with LCB (8 mL), and then LCB containing 0.5 M NaCl (2 mL).

Protein Phosphinothioester 32. The chitin column was washed with degassed cleavage buffer (CB, 5 mL), which was 50 mM MOPS NaOH buffer (pH 6.8) containing NaCl (0.50 M) and EDTA (0.10 mM). solution of CB (2.5 mL) containing phosphinothiol 17 (45 mg, 40 M) was added to the chitin resin, and 2 mL of buffer was allowed to lute by gravity. The column was sealed with a stopper and left under Ar(g) overnight. Protein phosphinothioester 32 was eluted from the column by the addition of 2 mL of a solution of NaCl (0.5 M), and precipitated by the addition of 300 μL of a solution of sodium deoxycholate (1% w/v) followed by 60 μL of a solution of trichloroacetic acid (50% w/v). The precipitate was collected by centrifugation at 5000 g for 5 min, resuspended in acetone to extract small molecules including excess phosphinothiol 17, and subjected to centrifugation again. Analysis of the precipitate by MALDI-TOF mass spectrometry showed the mass of protein phosphinothioester 32 to be m/z=14 225 (expected for Met(−1) RNase A-Gly-SCH$_2$(P($C_6H_4$-p-$CH_2CH_2NMe_2$)$_2$), $C_{603}H_{950}N_{175}O_{194}PS_{14}$, 14 224).

Example 2

The amino groups of phosphinothiol 17a (which become positively charged at appropriate pH) are eight bonds away from the key iminophosphorane nitrogen in the mechanism in Scheme 2. Even at this distance, however, through-space Coulombic effects can affect $pK_a$ values. For example, $CH_3(CH_2)_8NH_3^+$ has a $pK_a$ of 10.65. (Brown, H. C.; McDaniel, D. H.; Häfliger, O. In Determination of Organic Structures by Physical Methods; Braude, E. A., Hachod, F. C., Eds.; Academic Press: New York, 1955; pp 567-662.) The addition of a positive charge, as in $^+H_3N(CH_2)_8NH_3^+$, lowers the $pK_a$ to 10.10. Likewise, $CH_3(CH_2)_5NH_3^+$ and $^+H_3N(CH_2)_5NH_3^+$ have $pK_a$ values of 10.63 and 9.74, respectively. (Brown, H. C.; McDaniel, D. H.; Häfliger, O. In Determination of Organic Structures by Physical Methods; Braude, E. A., Hachod, F. C., Eds.; Academic Press: New York, 1955; pp 567-662.) As noted in Example 1, long-range Coulombic effects were also evident in attempts to mediate the traceless Staudinger ligation in water. Based on these considerations, we considered that favorable Coulombic effects would be enhanced by increasing the proximity of the positive charges.

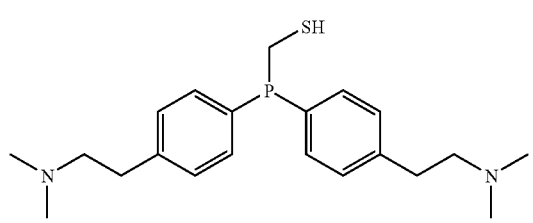

17a

Compounds 33 and 34 were prepared to test our reasoning as phosphinothiols with enhanced Coulombic effects for aqueous traceless Staudinger ligations. In these compounds, the N,N-dimethylamino group is closer to the reaction center by its being in the meta rather than the para position of the aryl ring (33 and 34), and its having a methylene rather than an ethylene linker (34). The N,N-dimethylaminoethyl substituent in the meta position is situated seven bonds away from the key iminophosphorane nitrogen, compared to the eight-bond distance of 17a. The meta N,N-dimethylaminomethyl substituent in phosphinothiol 34 is even closer, at a distance of six bonds. Ortho substituents are less preferred because they could add steric encumbrance to the reaction center, and the protonated N,N-dimethylamino group at the ortho position could act as an efficient intramolecular catalyst for deleterious protonation of the iminophosphorane nitrogen.

We also reasoned that the efficacy of the reagent in mediating the traceless Staudinger ligation in water would be enhanced by additional cationic charges. The amplified Coulombic effects could have a more pronounced effect on the protonation state of the iminophosphorane nitrogen. Phosphinothiol 35, which has four rather than two meta N,N-dimethylaminomethyl groups, was thus another target for synthesis and analysis.

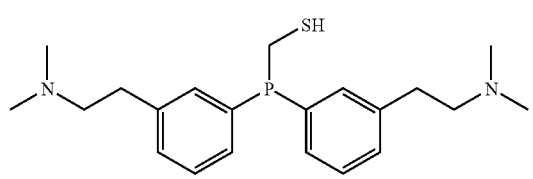

33a

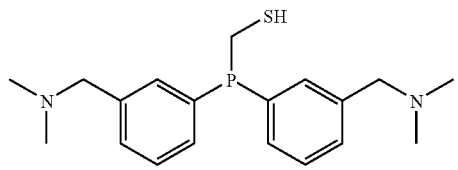

34a

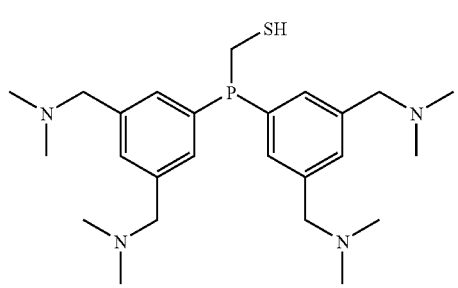

35a

Synthesis of Phosphinothiols 33-35

In phosphinothiols 17a, and 33-35, tertiary amino groups, rather than primary or secondary ones, were chosen to obviate intramolecular S→N acyl transfer in ensuing thioesters. Due to the presence of nitrogen, phosphorus, and sulfur in the phosphinothiol, several orthogonal protection/deprotection steps were necessary to effect the synthesis. Accordingly, the route to 17a consisted of nine linear steps (See Example 1). The purification of most intermediates was possible by chromatography using simple silica plugs, as the reactions were efficient and essentially 'spot-to-spot' conversions. Moreover, each reaction in the route was readily scalable. Nonetheless, the time required to generate fully-deprotected 17a from commercial starting materials was approximately one week.

Phosphinothiols 33-35 were synthesized by analogous synthetic routes (Scheme 7). Although (3-bromobenzyl)dimethylamine (49) was available from commercial sources, bromide 46 was accessible from 3-bromophenethyl alcohol through the displacement of its mesylate in 45 with dimethylamine. Bromide 48 was synthesized from the bromination of 5-bromo-m-xylene with N-bromosuccinimide and catalytic AIBN to give 47, followed by benzylic displacement with dimethylamine. (Vandekuil, L. A.; Luitjes, H.; Grove, D. M.; Zwikker, J. W.; Vanderlinden, J. G. M.; Roelofsen, A. M.; Jenneskens, L. W.; Drenth, W.; Vankoten, G. Organometallics 1994, 13, 468-477.) Double Grignard addition of the respective aryl bromides with diethylphosphite gave the bis-adducts 50-52. Bromide 48 must be dried stringently under high vacuum, and the addition of a few drops of 1,2-dibromoethane was also advantageous for facilitating Grignard initiation. Reduction with DIBAl-H and subsequent protection with borane gave phosphine-borane complexes 53-55. The protected phosphinothioester intermediates 57-59 were synthesized in a convergent manner utilizing the easily-prepared bromide 56, (Farrington, G. K.; Kumar, A.; Wedler, F. C. Org. Prep. Proced. Int. 1989, 21, 390-392) which had been employed in the convergent synthesis of (diphenylphosphino)methanethiol. (Soellner, M. B.; Nilsson, B. L.; Raines, R. T. J. Org. Chem. 2002, 67, 4993-4996.)

Phosphine-borane complexes 57-59 are stable to prolonged storage without decomposition. Removal of the borane groups with DABCO, deprotection of the thiol in basic methanol, and subsequent acidification with 4 N HCl/dioxane gave the chloride salts of phosphinothiols 33-35, which are easy-to-handle, odor-free white solids that are soluble at >1 M in 0.4 M sodium-phosphate buffer (pH 7.8).

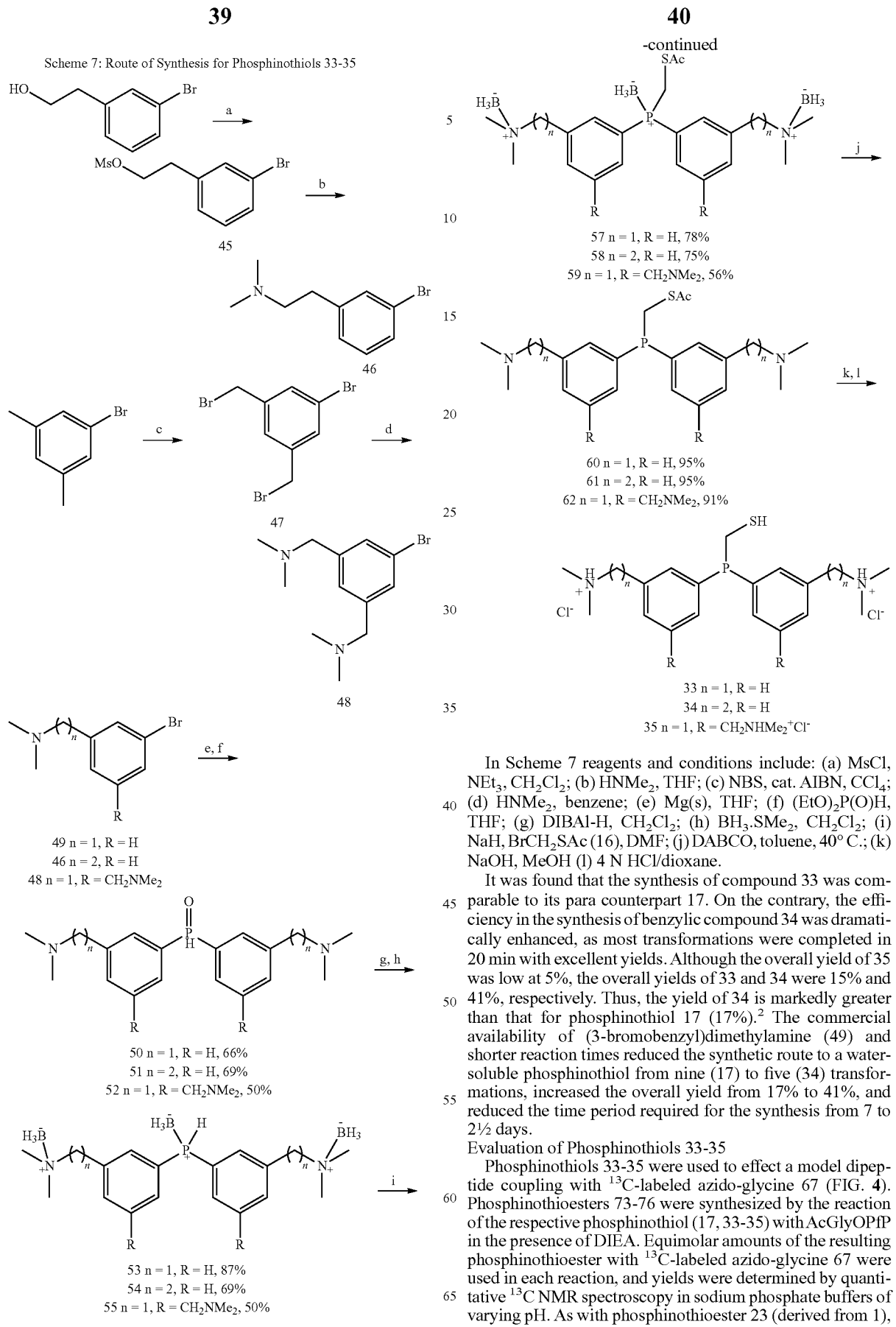

Scheme 7: Route of Synthesis for Phosphinothiols 33-35

In Scheme 7 reagents and conditions include: (a) MsCl, NEt₃, CH₂Cl₂; (b) HNMe₂, THF; (c) NBS, cat. AIBN, CCl₄; (d) HNMe₂, benzene; (e) Mg(s), THF; (f) (EtO)₂P(O)H, THF; (g) DIBAl-H, CH₂Cl₂; (h) BH₃·SMe₂, CH₂Cl₂; (i) NaH, BrCH₂SAc (16), DMF; (j) DABCO, toluene, 40° C.; (k) NaOH, MeOH (l) 4 N HCl/dioxane.

It was found that the synthesis of compound 33 was comparable to its para counterpart 17. On the contrary, the efficiency in the synthesis of benzylic compound 34 was dramatically enhanced, as most transformations were completed in 20 min with excellent yields. Although the overall yield of 35 was low at 5%, the overall yields of 33 and 34 were 15% and 41%, respectively. Thus, the yield of 34 is markedly greater than that for phosphinothiol 17 (17%).[2] The commercial availability of (3-bromobenzyl)dimethylamine (49) and shorter reaction times reduced the synthetic route to a water-soluble phosphinothiol from nine (17) to five (34) transformations, increased the overall yield from 17% to 41%, and reduced the time period required for the synthesis from 7 to 2½ days.

Evaluation of Phosphinothiols 33-35

Figure 4:
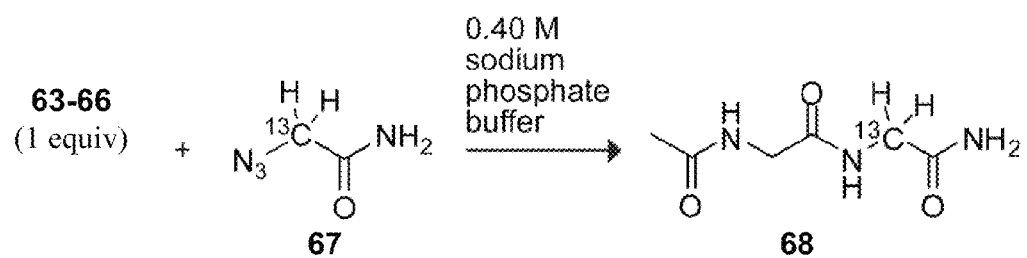
FIG. 4 illustrates the comparison of amide yield in the traceless Staudinger ligations mediated by phosphinothiols 17a and 33a-35a in an aqueous buffer. Phosphinothioesters 63-66 were synthesized by the reaction of the respective phosphinothiol with AcGlyOPfP. Dependence of amide yield (68) on the solution pH. Reactions were performed with equimolar amounts of phosphinothioesters and azide 67 (60 mM) in 0.40M sodium phosphate buffers of varying pH. Data are mean values (SE=±2%) from two experiments, and yields were determined by $^{13}$C NMR spectroscopy.
Figure 4:
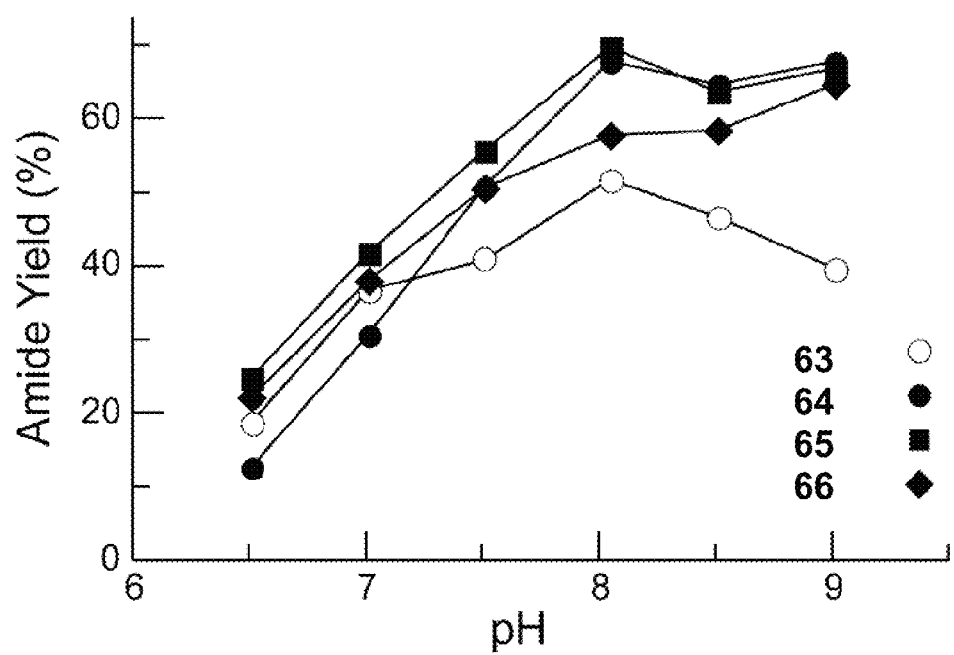

Phosphinothiols 33-35 were used to effect a model dipeptide coupling with $^{13}$C-labeled azido-glycine 67 (FIG. 4). Phosphinothioesters 73-76 were synthesized by the reaction of the respective phosphinothiol (17, 33-35) with AcGlyOPfP in the presence of DIEA. Equimolar amounts of the resulting phosphinothioester with $^{13}$C-labeled azido-glycine 67 were used in each reaction, and yields were determined by quantitative $^{13}$C NMR spectroscopy in sodium phosphate buffers of varying pH. As with phosphinothioester 23 (derived from 1), phosphinothioesters 64-66 provided amide 68 with yields dependent on the pH of the reaction mixture, peaking at pH 8.0. At each pH, however, the ligation yield with 65 was superior to that with phosphinothiol 63, 64, and 66.

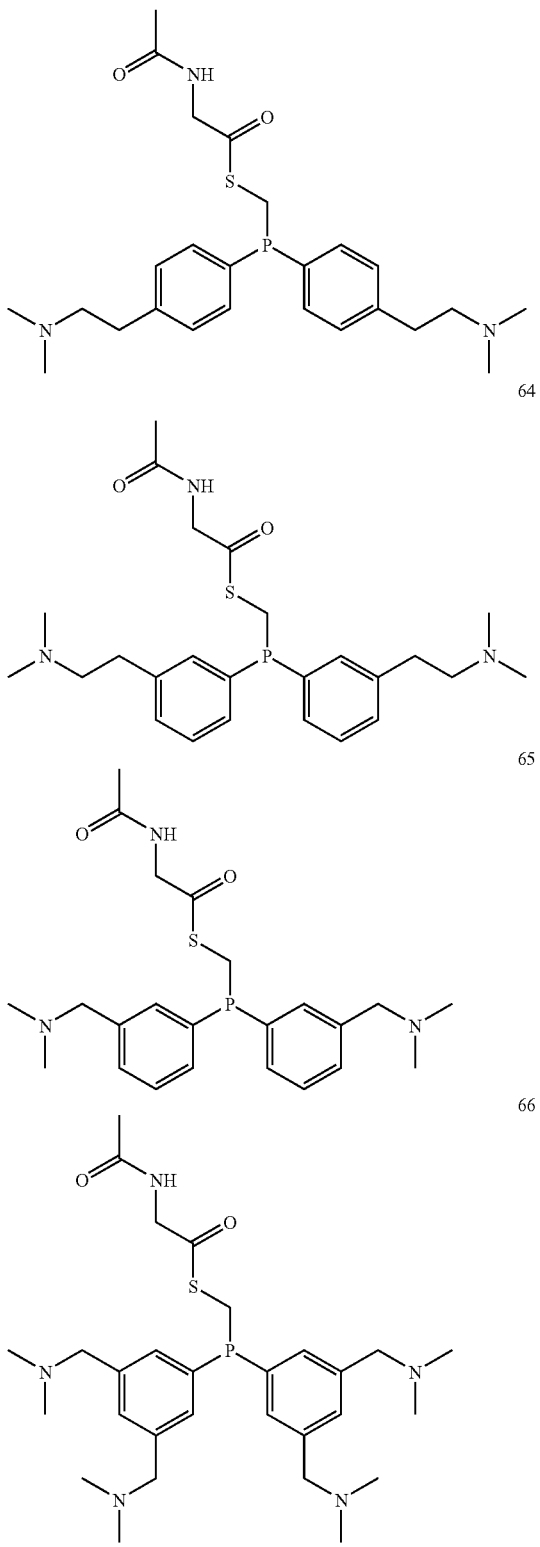

Interestingly, the additional cationic charges present in the molecule, as in 66, did not improve yields further. We reason that there are competing through-bond effects that promote amine formation, which is the only byproduct of this reaction. Unprotonated N,N-dimethylaminomethyl groups are slightly electron donating substituents and would increase electron density on the phosphorus of the iminophosphorane, rendering the nitrogen more susceptible to protonation. Such an inductive effect is apparent in the phosphorous pKa values of (p-OMe-$C_6H_4$)$_3$P (4.57), $Ph_3P$ (2.73), and (p-F—$C_6H_4$)$_3$P (1.97) in water. (Moore, S. J.; Marzilli, L. G. Inorg. Chem. 1998, 37, 5329-810 5335.)

The pKa values of phosphinothiols 33-35 were determined to quantitate the impact of Coulombic effects. Using $^{31}$P NMR spectroscopy, it was found that the phosphorus atoms of all positively-charged phosphinothiols remained largely unprotonated at pH ≧1.0 in water. Thus, the phosphorous pKa value of the cationic phosphinothiols appears to be below the limit of experimental detection. $EtPPh_2$, which is a neutral mimic of $HSCH_2PPh_2$, has a phosphorous pKa of 4.90. (Moore, S. J.; Marzilli, L. G. Inorg. Chem. 1998, 37, 5329-810 5335.) That value is much larger than the phosphorous pKa of phosphinothiols 33-35, consistent with the present hypothesis that through-space Coulombic effects lower the pKa of neighboring atoms, and in particular discourage protonation of the key iminophosphorane intermediate.

Careful consideration of the proximity of cationic groups to the key iminophosphorane intermediate permitted the development of improved phosphinothiol reagents for mediating the traceless Staudinger ligation in water. With its positively-charged N,N-dimethylamino groups closer to the iminophosphorane nitrogen, phosphinothiol 34 proved to be superior to our previous reagent (17), approaching yields of 70% near pH 8.0. The synthesis of 34 is efficient and high-yielding, facilitating its widespread use in peptide and protein chemistry. An attempt to amplify the Coulombic effects with additional positive charges proved to be unsuccessful, presumably because of deleterious inductive effects. These results show that an effective use of Coulombic interactions can be used to tune pKa values, which are an important consideration in aqueous traceless Staudinger ligations. Studies are ongoing in our laboratory to use such water-soluble phosphinothiols in the semisynthesis of proteins.

Experimental

General. Reagent chemicals were obtained from commercial suppliers, and reagent grade solvents were used without further purification. Procedures were performed at room temperature (<23° C.) unless indicated otherwise. Reactions were monitored by thin-layer chromatography with visualization by ultraviolet light or staining with $KMnO_4$, ninhydrin, PMA, or $I_2$. Compound purification was carried out with flash chromatography on a silica gel, which had a mesh of 230-400 (ASTM) and a pore size of 60 A°. The removal of solvents and other volatile materials "under reduced pressure" refers to the use of a rotary evaporator at water-aspirator pressure (<20 torr) and a water bath of <40° C.

Instrumentation. NMR spectra were acquired at ambient temperature with a Bruker AC-300 spectrometer ($^1$H, 300 MHz; $^{13}$C, 75 MHz; $^{31}$P, 121 MHz) at the University of Wisconsin Chemistry Department Nuclear Magnetic Resonance Facility or a Bruker DMX-400 Avance spectrometer ($^1$H, 400 MHz; $^{13}$C, 100.6 MHz; $^{31}$P, 161 MHz) or Bruker Avance DMX-500 spectrometer ($^1$H, 500 MHz; $^{13}$C, 125.7 MHz; $^{31}$P, 202 MHz) at the National Magnetic Resonance Facility at Madison (NMRFAM) or a Varian Inova 500 ($^1$H, 500 MHz; $^{13}$C, 125.7 MHz; $^{31}$P, 202 MHz) spectrometer at the University of Wisconsin Nuclear Magnetic Resonance Facility. Carbon-13 and phosphorus-31 spectra were proton-decoupled, and phosphorus-31 spectra were referenced against an external standard of deuterated phosphoric acid (0 ppm). Mass spectrometry was performed with a Micromass-LCT (electrospray ionization, ESI) in the Mass Spectrometry Facility in the Department of Chemistry.

Synthesis m-Br—$C_6H_4CH_2CH_2OMs$ (45) Triethylamine (5.2 mL, 37.3 mmol) was added to a solution of 4-bromophenethyl alcohol (5.0 g, 24.9 mmol) in $CH_2Cl_2$ (200 mL), and the resulting solution was cooled to 0° C. with an ice bath. Methanesulfonyl chloride (2.7 mL, 34.8 mmol) was added dropwise to the reaction mixture, and the resulting solution was allowed to warm slowly to room temperature overnight. The solution was washed with 0.1 N HCl and brine, and the combined organic extracts were dried over anhydrous $MgSO_4$(s) and filtered, and the solvent was removed under reduced pressure. The crude yellow solid was purified by flash chromatography (silica gel, 70% v/v hexanes in $CH_2Cl_2$) to give mesylate 45 as a white solid in 98% yield. $^1$H NMR (CDCl$_3$, 400 MHz) δ 7.42-7.40 (m, 2H), 7.21-7.16 (m, 2H), 4.41 (t, J=6.9 Hz, 2H), 3.03 (t, J=6.7 Hz, 2H), 2.90 (s, 3H) ppm; observed $^{13}$C NMR (CDCl$_3$, 100.6 MHz) δ 138.87, 132.25, 130.51, 127.87, 123.92, 69.79, 37.67, 35.46 ppm; MS (ESI) m/z 300.9519 (MNa+[$C_9H_{11}BrO_3SNa+$]=300.9595).

m-Br—$C_6H_4CH_2CH_2NMe_2$ (46) Mesylate 45 (6.68 g, 290 23.9 mmol) was dissolved in anhydrous THF (60 mL) under Ar(g), and dimethylamine (2 M in THF, 47 mL, 94 mmol) was added to this solution. The resulting solution was heated at 45° C. for 30 h. The white solid that formed was removed by filtration, and the solvent was removed under reduced pressure. The residue was purified by flash chromatography (silica gel, 10% v/v MeOH in $CH_2Cl_2$) to give dimethylamine 6 as a yellow oil in 63% yield. $^1$H NMR (CDCl$_3$, 400 MHz) δ 7.30-7.26 (m, 2H), 7.21-7.17 (m, 2H), 2.80-2.75 (m, 2H), 2.55-2.51 (m, 2H), 2.30 (s, 6H) ppm; observed $^{13}$C NMR (CDCl$_3$, 100.6 MHz) δ 140.64, 128.87, 128.87, 128.61, 126.28, 61.86, 45.73, 34.65 ppm; MS (ESI) m/z 228.0387 (MNa+[$C_{10}H_{14}BrNNa+$]=228.0388).

1-Br-3,5-bis($CH_2Br$)$C_6H_3$ (47). Bromide 47 was synthesized according to reports published previously where spectral data were reported. (Vandekuil, L. A.; Luitjes, H.; Grove, D. M.; Zwikker, J. W.; Vanderlinden, J. G. M.; Roelofsen, A. M.; Jennesskens, L. W.; Drenth, W.; Vankoten, G. Organometallics 1994, 13, 468-477.)

1-Br-3,5-bis($CH_2NMe_2$)$C_6H_3$ (48). Bromide 48 was synthesized according to reports published previously where spectral data were reported. (Vandekuil, L. A.; Luitjes, H.; Grove, D. M.; Zwikker, J. W.; Vanderlinden, J. G. M.; Roelofsen, A. M.; Jennesskens, L. W.; Drenth, W.; Vankoten, G. Organometallics 1994, 13, 468-477.)

HP(O)($C_6H_4$-m-$CH_2NMe_2$)$_2$ (50). Dimethylamine 49 (1.31 g, 6.13 mmol) was dissolved in anhydrous THF (15 mL) under Ar(g) in a flame-dried round-bottomed flask equipped with a reflux condenser. To facilitate generation of the Grignard reagent, a catalytic amount of 12 was added to the solution. Crushed magnesium turnings (223 mg, 9.2 mmol) were then added to this solution, and the resulting solution was heated at reflux for 2 hr to generate the Grignard reagent. In a separate flamed-dried flask, diethyl phosphite (237 μL, 1.84 mmol) was dissolved in anhydrous THF (1.0 mL), and cooled to 0° C. with an ice bath. The solution of Grignard reagent was added dropwise to this solution, and the resulting solution was allowed to warm to room temperature and stirred overnight. The reaction mixture was then quenched with water (1 mL), and the solvent was removed under reduced pressure. The residue was dissolved in $CH_2Cl_2$, and the resulting solution was washed with water and brine. The combined organic extracts were dried over anhydrous $MgSO_4$(s) and filtered, and the solvent was removed under reduced pressure. The residue was purified by flash chromatography (silica gel, 20% v/v MeOH in $CH_2Cl_2$) to give phosphine oxide 50 as a colorless oil in 66% yield. $^1$H NMR (CDCl$_3$, 400 MHz) δ 8.06 (d, J=1.2 Hz, 1H), 7.69 (s, 1H), 7.66 (s, 1H), 7.58 (t, J=7.5 Hz, 2H), 7.54 (dd, J=8.9, 1.2 Hz 2H), 7.45 (dd, J=7.6, 3.1 Hz 2H), 3.45 (s, 4H), 2.22 (s, 12H) ppm; $^{13}$C NMR (CDCl$_3$, 100.6 MHz) δ 140.22 (d, J=10.7 Hz), 133.45, 132.15, 131.31 (d, J=12.2 Hz), 129.67 (d, J=11.2 Hz), 129.14 (d, J=12.2 Hz), 64.06, 45.58 ppm; $^{31}$P NMR (CDCl$_3$, 161 MHz) δ 22.02 ppm; MS (ESI) m/z 288.0393 (MH+[$C_{18}H_{25}N_2OPH+$]=288.0383).

HP(O)($C_6H_4$-m-$CH_2CH_2NMe_2$)$_2$ (51). Dimethylamine 46 (1.70 g, 7.47 mmol) was dissolved in anhydrous THF (18 mL) under Ar(g) in a flame-dried round-bottomed flask equipped with a reflux condenser. To facilitate generation of the Grignard reagent, a catalytic amount of $I_2$(s) was added to the solution. Crushed magnesium turnings (272 mg, 11.2 mmol) were then added, and the resulting solution was heated at reflux for 2 h to generate the Grignard reagent. In a separate flamed-dried flask, diethylphosphite (289 μL, 2.24 mmol) was dissolved in anhydrous THF (1.5 mL), and cooled to 0° C. with an ice bath. The solution of Grignard reagent was added dropwise to this solution, and the resulting solution was allowed to warm to room temperature and stirred overnight. The reaction mixture was then quenched with water (1 mL), and the solvent was removed under reduced pressure. The residue was dissolved in $CH_2Cl_2$, and the resulting solution was washed with water and brine. The combined organic extracts were dried over anhydrous $MgSO_4$(s) and filtered, and the solvent was removed under reduced pressure. The residue was purified by flash chromatography (silica gel, 20% v/v MeOH in $CH_2Cl_2$) to give phosphine oxide 51 as a colorless oil in 69% yield. $^1$H NMR (CDCl$_3$, 400 MHz) δ 8.03 (d, J=1.2 ppm, 1H), 7.62 (s, 1H), 7.59 (s, 1H), 7.44-7.41 (m, 6H), 2.84-2.80 (m, 4H), 2.55-2.51 (m, 4H), 2.28 (s, 12H) ppm; $^{13}$C NMR (CDCl$_3$, 100.6 MHz) δ 141.62 (d, J=14.0 Hz), 133.21, 370132.09, 131.10 (d, J=11.4 Hz), 129.13 (J=15.4 Hz), 128.53 (d, J=14.0 Hz), 61.26, 45.62, 34.33 ppm; $^{31}$P NMR (CDCl$_3$, 161 MHz) δ 22.14 ppm; MS (ESI) m/z 345.2079 (MNa+[$C_{20}H_{29}N_2OPNa+$]=345.2096).

HP(O)($C_6H_3$-bis-m,m-$CH_2NMe_2$)$_2$ (52) Bromide 48 (2.88 g, 10.6 mmol) was dissolved in anhydrous THF (30 mL) under Ar(g) in a flame-dried round-bottomed flask equipped with a reflux condenser. To facilitate generation of the Grignard reagent, two drops of 1,2-dibromoethane was added to the solution. Crushed magnesium turnings (387 mg, 16.0 mmol) were then added to this solution, and the resulting solution was heated at reflux for 2 h to generate the Grignard reagent. In a separate flamed-dried flask, diethyl phosphate (256 μL, 3.19 mmol) was dissolved in anhydrous THF (15 mL), and cooled to 0° C. with an ice bath. The solution of Grignard reagent was added dropwise to this solution, and the resulting solution was allowed to warm to room temperature and stirred overnight. The reaction mixture was then quenched with water (1 mL), and the solvent was removed under reduced pressure. The residue was dissolved in $CH_2Cl_2$, and the resulting solution was washed with water and brine. The combined organic extracts were dried over anhydrous $MgSO_4$(s) and filtered, and the solvent was removed under reduced pressure. The residue was purified by flash chromatography (silica gel, 20% v/v MeOH in $CH_2Cl_2$ with 1% v/v NEt$_3$) to give phosphine oxide 52 as a yellow oil in 50% yield. $^1$H NMR (CDCl$_3$, 400 MHz) δ 8.09 (d, J=1.2 ppm, 1H), 7.58 (s, 2H), 7.54 (s, 2H), 7.51 (s, 2H), 3.44 (s, 8H), 2.21 (s, 24H) ppm; $^{13}$C NMR (CDCl$_3$, 100.6 MHz) 140.00 (d, J=13.4 Hz), 133.91, 131.36, 129.98 (d, J=11.6 Hz), 63.75, 45.33 ppm; $^{31}$P NMR (CDCl$_3$, 161 MHz) δ 22.48 ppm; MS (ESI) m/z 431.2946 (MH+[C$_{24}$H$_{39}$N$_4$OPH+]=431.2935).

BH$_3$.PH(C$_6$H$_4$-m-CH$_2$NMe$_2$)$_2$ (53). A solution of phosphine oxide 50 383 mg, 1.21 mmol) in anhydrous CH$_2$Cl$_2$ (2.6 mL) was added dropwise slowly to a solution of DIBAl-H (1 M in CH$_2$Cl$_2$, 6.05 mL, 6.05 mmol) under Ar(g) in a flame-dried three-neck round-bottomed flask. The resulting solution was stirred for 20 min, then cooled to 0° C. with an ice bath. The solution was then diluted with CH$_2$Cl$_2$ (10 mL), and a sparge needle of Ar(g) was allowed to blow through the solution for 5 min. A solution of 2N NaOH (5 mL) was added dropwise slowly to the reaction mixture (Caution! Gas evolution!) followed by a saturated solution of Rochelle's salt (5 mL) to dissipate the emulsion that forms. The resulting biphasic solution was transferred to a separatory funnel, and the organic layer was separated, dried over anhydrous MgSO$_4$(s), filtered, and concentrated under reduced pressure to ~12 mL. The resulting solution was cooled to 0° C. with an ice bath under Ar(g), and borane-dimethyl sulfide complex (10 M, 387 µL, 3.87 mmol) was added dropwise. The resulting reaction mixture was allowed to warm slowly to room temperature overnight. The solvent was removed under reduced pressure, and the crude oil was purified by flash chromatography (silica gel, CH$_2$Cl$_2$) to give phosphine-borane complex 53 as a white solid in 87% yield. $^1$H NMR (CDCl$_3$, 400 MHz) δ 7.73-7.70 (m, 4H), 7.55-7.49 (m, 4H), 6.38 (dq, J=381.3 Hz, 7.1 Hz, 1H), 3.95 (s, 4H), 2.53 (s, 6H), 2.52 (s, 6H), 2.15-0.80 (m, 9H) ppm; $^{13}$C NMR (CDCl$_3$, 100.6 MHz) δ 137.01 (d, J=8.4 Hz), 135.91, 133.80 (d, J=8.5 Hz), 132.85 (d, J=10.2 Hz), 129.41 (d, J=56.7 Hz), 126.67 (d, J=55.9 Hz), 67.39, 50.76 (d, J=21.6 Hz) ppm; $^{31}$P NMR (CDCl$_3$, 161 MHz) δ 0.98 ppm; MS (ESI) m/z 360.3095 (MNH$^+_4$ [C$_{18}$H$_{34}$B$_3$N$_2$PNH$^+_4$]=360:3078).

BH$_3$.PH(C$_6$H$_4$-m-CH$_2$CH$_2$NMe$_2$)$_2$ (54). A solution of phosphine oxide 51 (288 mg, 0.84 mmol) in anhydrous CH$_2$Cl$_2$ (1.8 mL) was added dropwise slowly to a solution of DIBAl-H (1 M in CH$_2$Cl$_2$, 4.18 mL, 4.18 mmol) under Ar(g) in a flame-dried three-neck round-bottomed flask. The resulting solution was stirred for 20 min, then cooled to 0° C. with an ice bath. The solution was then diluted with CH$_2$Cl$_2$ (10 mL), and a sparge needle of Ar(g) was allowed to blow through the solution for 5 min. A solution of 2 N NaOH (5 mL) was added dropwise slowly to the reaction mixture (Caution! Gas evolution!) followed by a saturated solution of Rochelle's salt (5 mL) to dissipate the emulsion that forms. The resulting biphasic solution was transferred to a separatory funnel, and the organic layer was separated, dried over anhydrous MgSO$_4$(s), filtered, and concentrated under reduced pressure to ~8 mL. The resulting solution was cooled to 0° C. with an ice bath under Ar(g), and borane.dimethyl sulfide complex (10 M, 268 µL, 2.68 mmol) was added dropwise. The resulting reaction mixture was allowed to warm slowly to room temperature overnight. The solvent was removed under reduced pressure, and the crude oil was purified by flash chromatography (silica gel, CH$_2$Cl$_2$) to give phosphine-borane complex 54 as a white solid in 69% yield. $^1$H NMR (CDCl$_3$, 400 MHz) δ 7.54-7.50 (m, 4H), 7.44-7.37 (m, 4H), 6.30 (dq, J=380.2 Hz, 1H), 3.14-3.09 (m, 4H), 2.97-2.93 (m, 4H), 2.66 (s, 12H), 2.15-0.70 (m, 9H) ppm; $^{13}$C NMR (CDCl$_3$, 100.6 MHz) d 139.50 (d, J=9.8 Hz), 133.20 (d, 470 J=10.4 Hz), 132.48, 131.59 (d, J=8.8 Hz), 129.77 (d, J=56.7 Hz), 126.57 (d, J=58.7 Hz), 65.89, 52.12 (d, J=9.4 Hz), 30.92 ppm; $^{31}$P NMR (CDCl$_3$, 161 MHz) δ 1.64 ppm; MS (ESI) m/z 388.3372 (MNH$^+_4$ [C$_{20}$H$_{36}$B$_3$N$_2$PNH$^+_4$]=388: 3391).

BH$_3$.PH(C$_6$H$_3$-bis-m,m-CH$_2$NMe$_2$)$_2$ (55) A solution of phosphine oxide 52 (200 mg, 0.46 mmol) in anhydrous CH$_2$Cl$_2$ (1.5 mL) was added dropwise slowly to a solution of DIBAl-H (1 M in CH$_2$Cl$_2$, 2.32 mL, 2.32 mmol) under Ar(g) in a flame-dried three-neck 480 round-bottomed flask. The resulting solution was stirred for 20 min, then cooled to 0° C. with an ice bath. The solution was then diluted with v (10 mL), and a sparge needle of Ar(g) was allowed to blow through the solution for 5 min. A solution of 2 N NaOH (3 mL) was added dropwise slowly to the reaction mixture (Caution! Gas evolution!) followed by a saturated solution of Rochelle's salt (5 mL) to dissipate the emulsion that forms. The resulting biphasic solution was transferred to a separatory funnel, and the organic layer was separated, dried over anhydrous MgSO$_4$(s), filtered, and concentrated under reduced pressure to ~5 mL. The resulting solution was cooled to 0° C. with an ice bath under Ar(g), and borane.dimethyl sulfide complex (10 M, 241 µL, 2.40 mmol) was added dropwise. The resulting reaction mixture was allowed to warm slowly to room temperature overnight. The solvent was removed under reduced pressure, and the crude oil was purified by flash chromatography (silica gel, 5% v/v EtOAc and 25% v/v hexanes in CH$_2$Cl$_2$) to give phosphine-borane complex 55 as a white solid in 50% yield. $^1$H NMR (CDCl$_3$, 400 MHz) δ 7.85 (s, 2H), 7.82 (s, 2H), 7.70 (s, 2H), 6.47 (dq, J=0.963 ppm, 7.1 Hz, 1H), 3.98-3.91 (m, 8H), 2.56 (s, 12H), 2.53 (s, 12H), 1.80-0.80 (m, 15H) ppm; $^{13}$C NMR (CDCl$_3$, 100.6 MHz) δ 140.27, 137.53 (d, J=9.8 Hz), 133.05 (d, J=10.0 Hz), 125.69 (d, J=56 Hz), 67.12, 51.38 (d, J=50.9 Hz) ppm; $^{31}$P NMR (CDCl$_3$, 161 MHz) δ1.12 ppm; MS (ESI) m/z 507.4447 (MNa+[C$_{24}$H$_{54}$B$_5$N$_4$PNa+]=507.4444).

BH$_3$.AcSCH$_2$P(C$_6$H$_4$-m-CH$_2$NMe$_2$)$_2$ (57) Phosphine-borane complex 53 (81 mg, 0.24 mmol) was dissolved in dry DMF (2.5 mL) under Ar(g) and cooled to 0° C. NaH (5.7 mg, 0.24 mmol) was added slowly, and the mixture was stirred at 0° C. until bubbling ceased. Bromide 56 (40 mg, 0.24 mmol) was then added, and the resulting mixture was allowed to warm to room temperature and stirred for 12 h. Solvent was removed under reduced pressure, and the residue was purified by flash chromatography (silica gel, 2% v/v ethyl acetate and 28% hexanes in CH$_2$Cl$_2$) to give phosphine-borane complex 57 as a white solid in 78% yield. $^1$H NMR (CDCl$_3$, 400 MHz) δ 7.78-7.73 (m, 4H), 7.57-7.49 (m, 4H), 3.95 (d, J=2.4 Hz, 4H), 3.73 (d, J=6.3 Hz, 2H), 2.53 (d, J=6.3 Hz, 12H), 2.25 (s, 3H), 2.20-0.60 (m, 9H) ppm; $^{13}$C NMR (CDCl$_3$, 100.6 MHz) δ 192.88, 136.42 (d, J=9.5 Hz), 135.93, 133.41 (d, J=9.4 Hz), 132.53 (d, J=9.9 Hz), 129.03 (d, J=10.0 Hz), 127.73 (d, J=54.6 Hz), 67.45, 53.65, 30.18, 23.70 (d, J=35.7 Hz) ppm; $^{31}$P NMR (CDCl$_3$, 161 MHz) δ 530 19.97 ppm; MS (ESI) m/z 453.2595 (MNa+[C$_{21}$H$_{38}$B$_3$N$_2$OPSNa+]=453.2614).

BH$_3$.AcSCH$_2$P(C$_6$H$_4$-m-CH$_2$CH$_2$NMe$_2$)$_2$ (58) Phosphine-borane complex 54 (100 mg, 0.27 mmol) was dissolved in dry DMF (3 mL) under Ar(g) and cooled to 0° C. NaH (6.5 mg, 0.27 mmol) was added slowly, and the mixture was stirred at 0° C. until bubbling ceased. Bromide 16 (46 mg, 0.27 mmol) was then added, and the resulting mixture was allowed to warm to room temperature and stirred for 12 h. Solvent was removed under reduced pressure, and the residue was purified by flash chromatography (silica gel, 2% v/v ethyl acetate and 28% hexanes in CH$_2$Cl$_2$) to give phosphine-borane complex 58 as a white solid in 75% yield. $^1$H NMR (CDCl$_3$, 400 MHz) δ 7.56-7.52 (m, 4H), 7.45-7.38 (m, 4H), 3.71 (d, J=6.8 Hz, 2H), 3.13-3.09 (m, 4H), 2.97-2.92 (m, 4H), 2.67 (d, J=2.7 Hz, 12H), 2.28 (s, 3H), 2.40-0.60 (m, 9H) ppm; $^{13}$C NMR (CDCl$_3$, 100.6 MHz) δ 193.34, 139.26 (d, J=9.9 Hz), 132.77 (d, J=11.7 Hz), 132.58, 130.96 (d, 550 J=8.3 Hz), 129.54 (d, J=10.0 Hz), 128.23 (d, J=55.9 Hz), 65.83, 52.05, 30.95, 30.32, 23.81 (d, J=35.3 Hz) ppm; $^{31}$P NMR (CDCl$_3$, 161 MHz) δ 19.65 ppm; MS (ESI) m/z 481.2918 (MNa+ [C$_{23}$H$_{42}$B$_3$N$_2$OPSNa+]=481.2927).

BH$_3$.AcSCH$_2$P(C$_6$H$_3$-bis-m,m-CH$_2$NMe$_2$)$_2$ (59) Phosphine-borane complex 55 (86 mg, 0.18 mmol) was dissolved in dry DMF (2 mL) under Ar(g) and cooled to 0° C. NaH (4.3 mg, 0.18 mmol) was added slowly, and the mixture was stirred at 0° C. until bubbling ceased. Bromide 56 (30 mg, 0.18 mmol) was then added, and the resulting mixture was allowed to warm to room temperature and stirred for 12 h. Solvent was removed under reduced pressure, and the residue was purified by flash chromatography (silica gel, 10% v/v ethyl acetate and 20% v/v hexanes in CH$_2$Cl$_2$) to give phosphine-borane complex 59 as a white solid in 56% yield. $^1$H NMR (CDCl$_3$, 400 MHz) δ 7.91 (d, J=1.1 Hz, 2H), 7.88 (d, J=1.1 Hz, 2H), 7.74 (s, 2H), 3.93 (q, J=13.7 Hz, 8H), 3.73 (d, J=6.3 Hz, 2H), 2.58 (s, 12H), 2.57 (s, 12H), 2.23 (s, 3H), 2.00-1.50 (m, 570 15H) ppm; $^{13}$C NMR (CDCl$_3$, 100.6 MHz) δ 192.70, 140.46, 137.24 (d, J=9.5 Hz), 132.84 (d, J=10.2 Hz), 126.98 (d, J=54.9 Hz), 67.94, 52.04, 51.09, 30.28 24.21 (d, J=34.9 Hz) ppm; $^{31}$P NMR (CDCl$_3$, 161 MHz) δ 18.74 ppm; MS (ESI) m/z 590.4409 (MNa+[C$_{27}$H$_{58}$B$_5$N$_4$OPSNa+] =590.4427).

AcSCH$_2$P(C$_6$H$_4$-m-CH$_2$NMe$_2$)$_2$ (60) Phosphine-borane complex 57 (100 mg, 0.23 mmol) was dissolved in toluene (2 mL) under Ar(g). DABCO (84 mg, 0.74 mmol) was added, and the resulting solution was heated to 40° C. for 4 h. The solvent was removed under reduced pressure, and the residue was purified by flash chromatography (silica gel, 20% v/v MeOH in CH$_2$Cl$_2$) to give phosphinothioester 60 as a colorless oil in 95% yield. $^1$H NMR (CDCl$_3$, 400 MHz) δ 7.38-7.29 (m, 8H), 3.53 (d, J=3.7 Hz, 2H), 3.41 (s, 4H), 2.28 (s, 3H), 2.22 (s, 12H) ppm; $^{13}$C NMR (CDCl$_3$, 100.6 MHz) δ 194.74, 138.88 (d, J=4.7 Hz), 136.91 (d, J=13.4 Hz), 133.83 (t, J=19.2 Hz), 131.56, 130.17 (d, J=29.9 Hz), 128.63 (d, J=32.2 Hz), 64.15, 45.63, 590 30.76, 20.96 (d, J=23.5 Hz) ppm; $^{31}$P NMR (CDCl$_3$, 161 MHz)-15.23 ppm.

AcSCH$_2$P(C$_6$H$_4$-m-CH$_2$CH$_2$NMe$_2$)$_2$ (61) Phosphine-borane complex 58 (38 mg, 0.096 mmol) was dissolved in toluene (1 mL) under Ar(g). DABCO (35 mg, 0.30 mmol) was added, and the resulting solution was heated to 40° C. for 4 h. The solvent was removed under reduced pressure, and the residue was purified by flash chromatography (silica gel, 20% v/v MeOH in CH$_2$Cl$_2$) to give phosphinothioester 61 as a colorless oil in 95% yield. $^1$H NMR (CDCl$_3$, 400 MHz) δ 7.28-7.20 (m, 8H), 3.50 (d, J=3.4 Hz, 2H), 2.80-2.76 (m, 4H), 2.57-2.53 (m, 4H), 2.32 (s, 12H), 2.30 (s, 3H) ppm; $^{13}$C NMR (CDCl$_3$, 100.6 MHz) δ 194.87, 140.54 (d, J=7.7 Hz), 136.96 (d, J=14.2 Hz), 133.25 (d, J=22.8 Hz), 130.48 (d, J=16 Hz), 129.70, 128.78 (d, J=4.9 Hz), 64.26, 46.94, 45.47, 34.25, 25.99 (d, J=23.4 Hz) ppm; $^{31}$P NMR (CDCl$_3$, 161 MHz) δ 14.99 ppm.

AcSCH$_2$P(C$_6$H$_3$-bis-m,m-CH$_2$NMe$_2$)$_2$ (62). Phosphine-borane complex 59 (59 mg, 0.10 mmol) was dissolved in toluene (1.5 mL) under Ar(g). DABCO (60 mg, 0.54 mmol) was added, and the resulting solution was heated to 40° C. for 4 h. The solvent was removed under reduced pressure, and the residue was purified by flash chromatography (silica gel, 20% v/v MeOH in CH$_2$Cl$_2$ with 1% v/v NEt$_3$) to give phosphinothioester 62 as a colorless oil in 91% yield. $^1$H NMR (CDCl$_3$, 400 MHz) d 7.28-7.21 (m, 6H), 3.53 (d, J=3.7 Hz, 2H), 3.39 (m, 8H), 2.27 (s, 3H), 2.21 (s, 620 24H) ppm; $^{13}$C NMR (CDCl$_3$, 100.6 MHz) δ 194.82, 139.07 (d, J=7.4 Hz), 136.88 (d, J=14.6 Hz), 132.48 (d, J=18.8 Hz), 131.01, 64.12, 45.39, 30.43, 26.05 ppm; $^{31}$P NMR (CDCl$_3$, 161 MHz) δ −15.32 ppm.

HSCH$_2$P(C$_6$H$_4$-m-CH$_2$NMe$_2$)$_2$.2HCl (34) Phosphinothioester 60 (35 mg, 0.09 mmol) was dissolved in degassed MeOH (1 mL), and NaOH (3.7 mg) was added to this solution under Ar(g). The resulting solution was stirred at room temperature for 1.5 h. The solvent was removed under reduced pressure, and the residue was acidified with 4 N HCl in dioxane and filtered to give hydrochloride salt of phosphinothiol 3 as a white solid in quantitative yield. $^1$H NMR (CD$_3$OD, 400 Hz) δ 7.81 (d, J=5.9 Hz, 2H), 7.61-7.56 (m, 4H), 7.49 (d, J=7.4 Hz, 2H), 4.37 (s, 4H), 3.27 (d, J=2.6 Hz, 2H), 2.84 (s, 12H) ppm; $^{13}$C NMR (CD$_3$OD, 100.6 MHz) δ 140.34 (d, J=17.4 Hz), 136.25 (d, J=17.2 Hz), 135.45 (d, J=23.1 Hz), 133.02, 132.18, 130.65 (d, J=7.0 Hz), 61.99, 54.95, 43.16 ppm; $^{31}$P NMR (CDCl$_3$, 161 MHz) 640 δ −8.59 ppm.

HSCH$_2$P(C$_6$H$_3$-bis-m,m-CH$_2$NMe$_2$)$_2$.4HCl (35) Phosphinothioester 62 (47 mg, 0.09 mmol) was dissolved in degassed MeOH (1 mL), and NaOH (3.7 mg) was added to this solution under Ar(g). The resulting solution was stirred at room temperature for 1.5 h. The solvent was removed under reduced pressure, and the residue was acidified with 4 N HCl in dioxane and filtered to give hydrochloride salt of phosphinothiol 35 as a white solid in quantitative yield. $^1$H NMR (CDCl$_3$, 400 Hz) δ 7.26-7.24 (m, 6H), 4.05 (d, J=5.2 Hz, 2H), 3.38, (s, 8H), 3.07 (m, 2H), 2.20 (s, 24H) ppm; $^{13}$C NMR (CDCl$_3$, 100.6 MHz) δ 139.20 (d, J=6.3 Hz), 137.12 (d, J=14.4 Hz), 132.48 (d, J=17.0 Hz), 130.99, 64.20, 45.48, 21.14 (d, J=23.3 Hz) ppm; $^{31}$P NMR (CDCl$_3$, 161 MHz) δ −7.71 ppm.

AcGlySCH$_2$P(C$_6$H$_4$-m-CH$_2$CH$_2$NMe$_2$)$_2$ (64) Phosphinothioester 61 (40 mg, 0.10 mmol) was dissolved in degassed MeOH (1 mL), and NaOH (3.8 mg) was 660 added to this solution under Ar(g). The resulting solution was stirred at room temperature for 1.5 h. The solvent was removed under reduced pressure, and the residue was acidified with 4 N HCl in dioxane and filtered to give hydrochloride salt of phosphinothiol 33 as a white solid in quantitative yield. The residue was used without further purification. N-Acetyl glycine pentafluorophenol ester (28.3 mg, 0.1 mmol) was dissolved in anhydrous DMF (1 mL) under Ar(g). The hydrochloride salt of phosphinothiol 33 from above was added, followed by DIEA (67 μL, 0.38 mmol). The resulting solution was stirred for 4 h at room temperature under Ar(g). The solvent was removed under reduced pressure, and the resulting crude oil was purified by flash chromatography (silica gel, 20% v/v MeOH in CH$_2$Cl$_2$) to give phosphinothioester 64 as a colorless oil in 75% yield. $^1$H NMR (CDCl$_3$, 400 Hz) δ 7.30-7.22 (m, 8H), 4.19 (d, J=6.2 Hz, 2H), 3.54 (d, J=3.9 Hz, 2H), 2.80-2.76 (m, 4H), 2.55-2.51 (m, 4H), 2.30 (s, 12H), 2.05 (s, 3H) ppm; $^{13}$C NMR (CDCl$_3$, 680 100.6 MHz) δ 196.48, 170.50, 140.66 (d, J=6.9 Hz), 136.78 (d, J=13.4 Hz), 133.37 (d, J=20.0 Hz), 130.66 (d, J=18.0 Hz), 129.92, 128.93, 61.38, 49.35, 45.6234.43, 25.60 (d, J=24.8 Hz), 23.25 ppm; $^{31}$P NMR (CDCl$_3$, 161 MHz) δ −14.48 ppm.

AcGlySCH$_2$P(C$_6$H$_4$-m-CH$_2$NMe$_2$)$_2$ (65) Phosphinothioester 60 (72 mg, 0.21 mmol) was dissolved in degassed MeOH (2 mL), and NaOH (8.3 mg) was added to this solution under Ar(g). The resulting solution was stirred at room temperature for 1.5 h. The solvent was removed under reduced pressure, and the residue was acidified with 4 N HCl in dioxane and filtered to give the hydrochloride salt of phosphinothiol 34 as a white solid in quantitative yield. The residue was used without further purification. N-Acetyl glycine pentafluorophenol ester (62 mg, 0.22 mmol) was dissolved in anhydrous DMF (2 mL) under Ar(g). A solution of the above phosphinothiol in DMF (1 mL) was added to the mixture. DIEA (144 μL, 0.83 mmol) was added to the resulting solution, and the mixture was stirred for 4 h at room temperature under Ar(g). The solvent was removed under reduced pressure, and the resulting crude oil was purified by flash chromatography (silica gel, 20% v/v MeOH in CH$_2$Cl$_2$) to give phosphinothioester 65 as a colorless oil in 95% yield. $^1$H NMR (CDCl$_3$, 400 Hz) δ 7.40-7.28 (m, 8H), 6.68 (bs, 1H), 4.11 (d, J=6.0 Hz, 2H), 3.53 (d, J=4.4 Hz, 2H), 3.48 (s, 4H), 2.27 (s, 12H), 2.04 (s, 3H) ppm; $^{13}$C NMR (CDCl$_3$, 100.6 MHz) δ 196.63, 170.75, 137.01 (d, J=14.2 Hz), 136.38, 134.18 (d, J=18.8 Hz), 132.65 (d, J=19.8 Hz), 130.93, 128.96 (d, J=6.2 Hz), 63.37, 710 49.15, 44.65, 25.32, 23.11 ppm; $^{31}$P NMR (CDCl$_3$, 161 MHz) δ −14.33 ppm.

AcGlySCH$_2$P(C$_6$H$_3$-bis-m,m-CH$_2$NMe$_2$)$_2$ (66) N-Acetyl glycine pentafluorophenol ester (27.7 mg, 0.1 mmol) was dissolved in anhydrous DMF (1 mL) under Ar(g). The hydrochloride salt of phosphinothiol 35 (41.4 mg, 0.09 mmol) was added, followed by DIEA (129 μL, 0.74 mmol). The resulting solution was stirred for 4 h at room temperature under Ar(g). The solvent was removed under reduced pressure, and the resulting crude oil was purified by flash chromatography (silica gel, 20% v/v MeOH in CH$_2$Cl$_2$ with 1% v/v NEt$_3$) to give phosphinothioester 66 as a mixture with unreacted 35. This mixture was dissolved in CH$_2$Cl$_2$ (2 mL) and 2-chlorotrityl chloride resin (200 mesh) (3 equiv) and TBD-methyl polystyrene resin (5 equiv) was added and gently stirred at RT for 30 min. The resin was filtered and washed with CH$_2$Cl$_2$. The filtrate was concentrated under reduced pressure to give 66 as a colorless oil in 72% yield. $^1$H NMR (CDCl$_3$, 400 Hz) δ 7.27-7.22 (m, 6H), 6.50 (bs, 1H), 4.09 (d, J=5.7 Hz, 2H), 3.54 (d, J=4.6 Hz, 2H), 3.37 (s, 8H), 2.20 (s, 24H), 2.02 (s, 3H) ppm; observed $^{13}$C NMR (CDCl$_3$, 100.6 MHz) δ 196.41, 170.35, 139.19 (d, J=7.5 Hz), 136.51 (d, J=13.6 Hz), 132.51 (d, J=18.2 Hz), 64.22, 53.61, 49.20, 45.51, 25.29 (d, J=26.5 Hz) ppm; $^{31}$P NMR (CDCl$_3$, 161 MHz) δ −13.68 ppm.

Staudinger ligations of 63+67, 64+67, 65+67, and 66+67 The respective phosphinothioester (36 μmol) and azide 67 (3.6 mg, 36 μmol) were dissolved in 0.40 M sodium phosphate buffers (0.6 mL) of various pH. The resulting reaction mixtures were stirred for 16 h and the reaction was monitored with quantitative $^{13}$C NMR spectroscopy. Amide yields were obtained by the integration of all normalized product $^{13}$C NMR signals.

pKa Determination of phosphinothiols Phosphinothioesters 60-62 (10 mg) were each dissolved in sodium phosphate buffer containing 20% v/v D$_2$O. 750 The solution was adjusted with a solution of either 6 N HCl or 2 N NaOH, and chemical shifts at each pH were determined by $^{31}$P NMR spectroscopy. An external standard (D$_3$PO$_4$) was used to calibrate the chemical shifts. A control experiment using tris(2-carboxyethyl)phosphine (TCEP) gave a pKa value of 7.7, which is similar to the reported value of 7.66. (Podlaha, J.; Podlahova, J. Collect. Czech. Chem. Commun. 1973, 38, 1730-1736.)

We claim:

1. A method for forming an amide bond in an aqueous solution which comprises forming a phosphinothioester from a corresponding water soluble phosphinothiol, and thereafter reacting the phosphinothioester with an azide in an aqueous solution to form the amide bond,
wherein the water soluble phosphinothiol has formula:

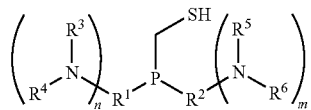

or protonated ions, quaternary ammonium ions or salts thereof wherein:
n and m are 0, 1, or 2 and n+m is 1 or more;
R$^1$ and R$^2$ are linkers that are organic biradicals which are selected from optionally substituted arylenes, optionally substituted heteroarylenes, optionally substituted alkylenes, or optionally substituted cycloalkylenes or combinations thereof;

n and m are 0, 1, or 2 and n+m is 1 or more; and each R$^3$-R$^6$, independently, is selected from guanidine, alkyl, alkenyl, alkynyl, aryl, or heteroaryl all of which are optionally substituted and wherein R$^3$ and R$^4$ or R$^5$ and R$^6$ or both combinations of groups are optionally linked to form a 5-8 member ring which contains N and optionally contains one or more additional heteroatoms;

wherein substitution, when present, is substitution with one or more groups selected from halogen, alkyl, alkenyl, alkynyl, aryl, heteroaryl, heterocycyl, —OH, —OR, —COH, —COR, —COOH, —COOR, or —N(R)$_2$, where each R is independently selected from optionally substituted alkyl, alkenyl, alkynyl, heterocyclic, aryl or heteroaryl groups.

2. The method of claim 1 wherein a peptide is formed.

3. The method of claim 1 wherein a protein is formed.

4. The method of claim 1 wherein the phosphinothioester formed is a phosphinothioester of an amino acid, peptide or protein.

5. The method of claim 1 wherein, R$^3$ and R$^4$, R$^5$ and R$^6$, or both are linked together to form:

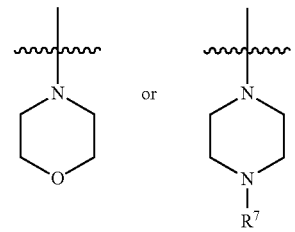

where R$^7$ is hydrogen, alkyl, alkenyl, alkynyl, heterocyclic, aryl or heteroaryl, each of which is optionally substituted.

6. The method of claim 1 wherein the water soluble phosphinothiol has formula:

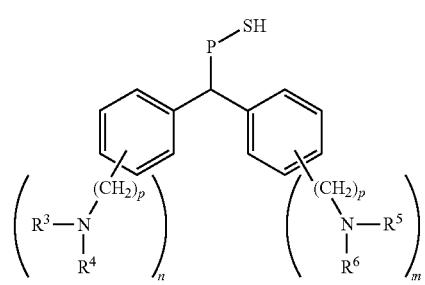

or protonated ions, quaternary ammonium ions or salts thereof, where p is an integer from 1 to 6.

7. The method of claim 1 wherein the water soluble phosphinothiol has formula:

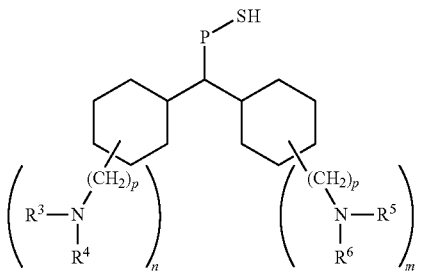

or protonated ions, quaternary ammonium ions and or salts thereof, where p is an integer from 1 to 6.

8. The method of claim 1 wherein the water soluble phosphinothiol has formula:

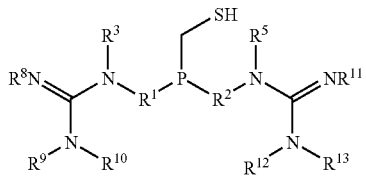

or protonated ions, quaternary ammonium ions or salts thereof wherein:
$R^8$-$R^{13}$, independently, are selected from hydrogen, alkyl, alkenyl, alkynyl, cycloalkyl, aryl, or heteroaryl which are optionally substituted with one or more alkyl, alkenyl, aryl, halides, —OH, —OR, —COH, —COR, —COON, —COOR or —N(R)$_2$.

9. The method of claim 1 wherein the water soluble phosphinothiol is selected from:

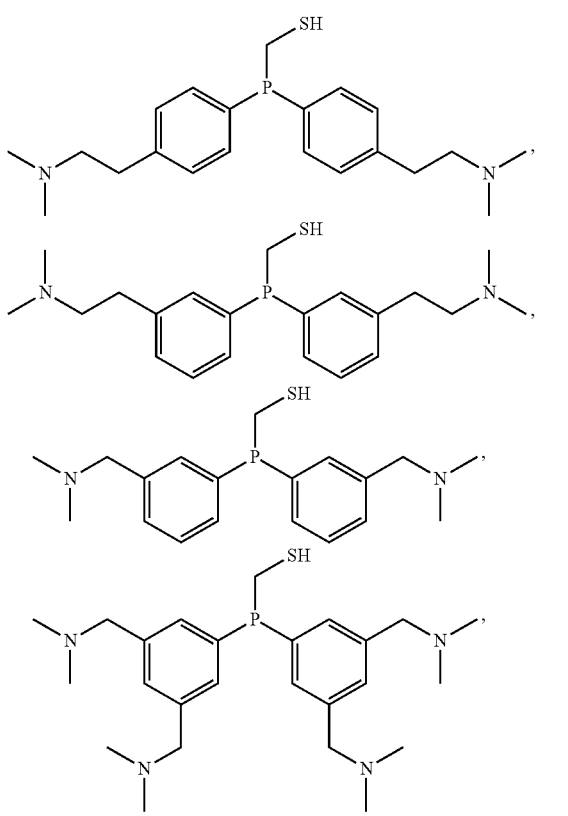

or protonated ions, quaternary ammonium ions or salts thereof.

10. The method of claim 1, wherein one of the phosphinothioester or the azide is covalently linked to a surface.

11. The method of claim 1 wherein the aqueous solution has pH between 6.0 and 8.5.

12. A water soluble phosphinothiol having formula:

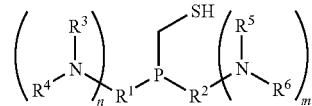

or protonated ions, quaternary ammonium ions or salts thereof wherein:
n and m are 0, 1, or 2 and n+m is 1 or more;
$R^1$ and $R^2$ are linkers that are organic biradicals which are selected from optionally substituted arylenes, optionally substituted heteroarylenes, optionally substituted alkylenes, or optionally substituted cycloalkylenes or combinations thereof;
n and m are 0, 1, or 2 and n+m is 1 or more; and
each $R^3$-$R^6$, independently, is selected from guanidine, alkyl, alkenyl, alkynyl, aryl, or heteroaryl all of which are optionally substituted and wherein $R^3$ and $R^4$ or $R^5$ and $R^6$ or both combinations of groups are optionally linked to form a 5-8 member ring which contains N and optionally contains one or more additional heteroatoms;
wherein substitution, when present, is substitution with one or more groups selected from halogen, alkyl, alkenyl, alkynyl, aryl, heteroaryl, heterocycyl, —OH, —OR, —COH, —COR, —COON, —COOR, or —N(R)$_2$, where each R is independently selected from optionally substituted alkyl, alkenyl, alkynyl, heterocyclic, aryl or heteroaryl groups.

13. The water soluble phosphinothiol of claim 12 wherein, $R^3$ and $R^4$, $R^5$ and $R^6$, or both are linked together to form:

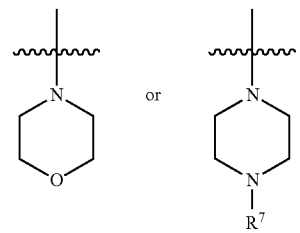

where $R^7$ is hydrogen, alkyl, alkenyl, alkynyl, heterocyclic, aryl or heteroaryl, each of which is optionally substituted.

14. The water soluble phosphinothiol of claim 12 having formula:

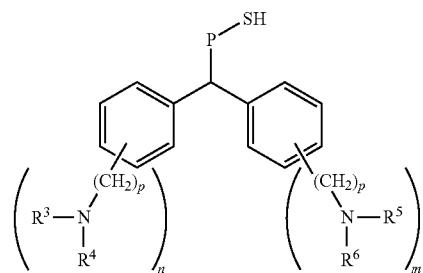

or protonated ions and quaternary ammonium ions or salts thereof, where p is an integer from 1 to 6.

15. The water soluble phosphinothiol of claim 14 which is selected from:

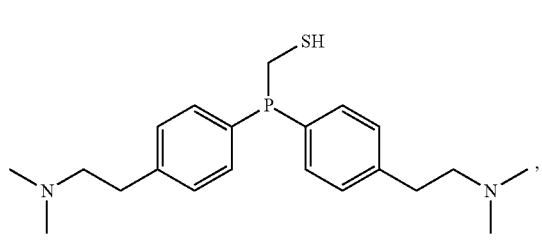

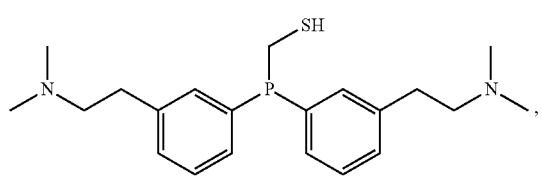

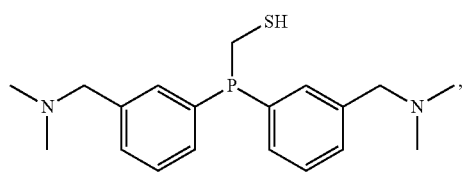

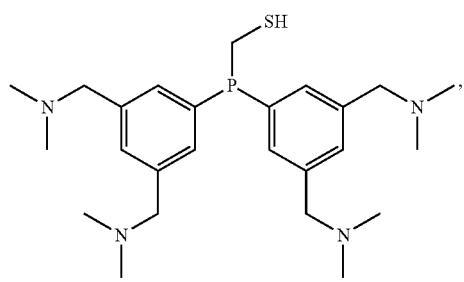

or protonated ions, quaternary ammonium ions or salts thereof.

16. The water soluble phosphinothiol of claim 12 having formula:

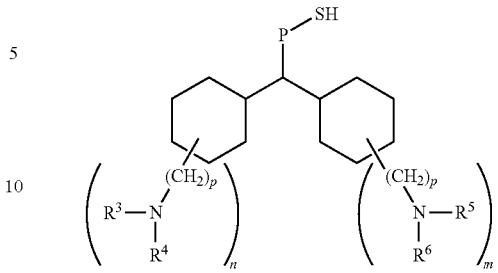

or protonated ions, quaternary ammonium ions or salts thereof, where p is an integer from 1 to 6.

17. The water soluble phosphinothiol of claim 12 having formula:

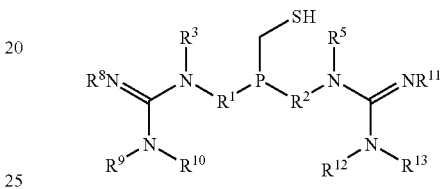

or protonated ions, quaternary ammonium ions or salts thereof wherein:

$R^8$-$R^{13}$, independently, are selected from hydrogen, alkyl, alkenyl, alkynyl, cycloalkyl, aryl, or heteroaryl, which are optionally substituted with one or more alkyl, alkenyl, aryl, halides, —OH, —OR, —COH, —COR, —COOH, —COOR or —N(R)$_2$.

18. A kit for forming an amide bond between an activated carboxylic acid derivative and an azide which comprises one or more of the phosphinothiol reagents of claim 12 and an azide.

19. A kit for synthesis of peptides or proteins which comprises one or more of the phosphinothiol reagents of claim 14.

20. A kit for forming an amide bond between an activated carboxylic acid derivative and an azide which comprises one or more of the phosphinothiol reagents of claim 14 and an azide.

21. A kit for synthesis of peptides or proteins which comprises one or more of the phosphinothiol reagents of claim 12.

* * * * *